United States Patent
Pfeiffer et al.

(10) Patent No.: US 11,705,242 B2
(45) Date of Patent: **\*Jul. 18, 2023**

(54) PROVIDING AN INTERACTIVE EMERGENCY DEPARTMENT DASHBOARD DISPLAY

(71) Applicant: CERNER INNOVATION, INC., Kansas City, KS (US)

(72) Inventors: Neil Pfeiffer, Overland Park, KS (US); Bradley J. Scott, Overland Park, KS (US); E. Rolland Phillips, III, Concord, NC (US); Leslie Ann Lindsey, Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 328 days.

This patent is subject to a terminal disclaimer.

(21) Appl. No.: 16/891,961

(22) Filed: Jun. 3, 2020

(65) Prior Publication Data

US 2020/0294662 A1    Sep. 17, 2020

Related U.S. Application Data

(63) Continuation of application No. 14/587,170, filed on Dec. 31, 2014, now Pat. No. 10,720,238, which is a
(Continued)

(51) Int. Cl.
    *G16H 40/63*    (2018.01)
    *G06F 3/0482*   (2013.01)
    (Continued)

(52) U.S. Cl.
    CPC ........... *G16H 40/63* (2018.01); *G06F 3/0482* (2013.01); *G16H 10/60* (2018.01); *G16H 40/20* (2018.01); *H04L 67/10* (2013.01)

(58) Field of Classification Search
    CPC ........ G16H 40/63; G16H 10/60; G16H 40/20; G06F 3/0482; H04L 67/10
    See application file for complete search history.

(56) References Cited

U.S. PATENT DOCUMENTS

| 5,072,383 A * | 12/1991 | Brimm ................. G16H 70/60 705/2 |
| 2003/0050794 A1 * | 3/2003 | Keck ...................... G16Z 99/00 705/2 |

(Continued)

OTHER PUBLICATIONS

Aronsky et al., "Supporting Patient Care in the Emergency Department with a Computerized Whiteboard System", Journal of the American Medical Informatics Association, vol. 15, No. 2, Mar./Apr. 2008 (Year: 2008).*

(Continued)

*Primary Examiner* — Evangeline Barr
(74) *Attorney, Agent, or Firm* — Kraguljac Law Group, LLC

(57) ABSTRACT

A method for presenting an interactive emergency department (ED) dashboard display for an ED at a user computing device is provided. The method may include presenting a plurality of user interface indicators on the interactive ED dashboard display at the user computing device. Each of the plurality of user interface indicators may correspond to a real-time performance metric for the ED, where the real-time performance metric is based on patient data for a plurality of patients in the ED. A user input may be received at the user computing device. The user input may indicate a selection of one of the plurality of user interface indicators. The method may further include, in response to the user input, presenting on the interactive ED dashboard display the patient data that is associated with the real-time performance metric corresponding to the selected one of the plurality of user interface indicators.

20 Claims, 38 Drawing Sheets

Related U.S. Application Data continuation-in-part of application No. 14/012,678, filed on Aug. 28, 2013, now abandoned.

(51) Int. Cl.
*H04L 67/10* (2022.01)
*G16H 10/60* (2018.01)
*G16H 40/20* (2018.01)

(56) References Cited

U.S. PATENT DOCUMENTS

| | | | |
|---|---|---|---|
| 2004/0163046 A1* | 8/2004 | Chu | H04L 67/75 715/251 |
| 2005/0137929 A1* | 6/2005 | Frazier | G06Q 10/0639 705/7.38 |
| 2005/0209880 A1 | 9/2005 | Drelicharz et al. | |
| 2007/0156456 A1* | 7/2007 | McGillin | G16H 40/67 600/300 |
| 2009/0106051 A1* | 4/2009 | Albro | G06Q 10/06 705/3 |
| 2009/0228330 A1* | 9/2009 | Karras | G16H 40/67 705/7.41 |
| 2010/0094656 A1 | 4/2010 | Conant | |
| 2012/0130730 A1* | 5/2012 | Setlur | G16H 40/20 705/2 |
| 2012/0191465 A1 | 7/2012 | Xue et al. | |
| 2012/0330674 A1 | 12/2012 | Brimm et al. | |

OTHER PUBLICATIONS

"Healthcare Executives, Gain the Power of Situational Awareness with RTLS", Available online at: <http://www.versustech.com/rtls-benefits/healthcare-executives>, Jul. 22, 2013, pp. 1-16.

Aronsky et al., "Supporting Patient Care in the Emergency Department with a Computerized Whiteboard System", Journal of the American Medical Informatics Association, vol. 15 No. 2, Mar./Apr. 2008, pp. 184-194.

\* cited by examiner

PROVIDING AN INTERACTIVE EMERGENCY DEPARTMENT DASHBOARD DISPLAY

RELATED APPLICATION

This patent application is a continuation of U.S. patent application Ser. No. 14/587,170, filed Dec. 31, 2014 and entitled "Providing an Interactive Emergency Department Dashboard Display"; which is a continuation-in-part of, and claims priority to, U.S. patent application Ser. No. 14/012,678, filed Aug. 28, 2013 and entitled "Emergency Department Status Display"; all of which are hereby expressly incorporated by reference in their entireties.

BACKGROUND

Clinicians in an emergency department of a healthcare facility have many responsibilities. Medications must be ordered, laboratory and electrocardiogram results must be analyzed, images must be viewed, patient histories and care plans must be observed, and information must be documented and signed, often for many patients at a time. This requires constant searching and scrolling to identify new items (e.g., lab results or images that have not yet been analyzed or viewed), which affects efficiency and the timely discharge of patients. Exacerbating this problem further, there is no single source that allows all of these responsibilities to be performed. Consequently, clinicians must spend additional time to find these items in various locations and open multiple applications. The result is inefficiency for the emergency department clinician, as well as increased lengths of stay for the affected patients.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for providing an emergency department centralized interactive display. A segmentable summary of patients within an ED allows a clinician to view a specific area within the ED or a summary of patients assigned to the clinician including unassigned patients sorted by acuity and length of stay. A throughput summary for a patient indicates throughput and whether actions are pending for the patient. The throughput may indicate whether the patient is pending arrival, waiting for a clinician, an exam has been completed, orders are pending, orders are completed, the patient is ready for discharge, and/or the patient is pending admission. A patient summary for the patient that includes information collected at triage, links to documentation from previous visits, care plans, a do not resuscitate order, home medications, and/or history. A provider summary provides information regarding providers for the patient and allows the clinician to designate an attending physician to the patient. In various embodiments, a consult summary, an order summary, a vitals summary, a length of stay summary, an acuity summary, and/or a documentation summary are provided, giving the ED clinician an efficient one-stop shop for performing ED duties.

Also described is an interactive ED dashboard display. The ED dashboard display may reflect an overall performance of the ED with respect to various performance metrics. The dashboard may include various user interface indicators that correspond to real-time performance metrics for the ED. A clinician may view the dashboard and quickly determine whether ED operations are running smoothly and identify problem areas to be addressed. In addition to the high-level performance data, the ED dashboard may also provide patient-level detail such that a clinician can determine the particular actions that should be taken with respect to particular patients in order to remedy an identified problem area.

BRIEF DESCRIPTION OF THE DRAWINGS

Embodiments are described in detail below with reference to the attached drawing figures, wherein:

FIGS. 3-30 depict illustrative screen displays, in accordance with exemplary embodiments of the present invention;

FIGS. 32-37 depict illustrative interactive ED dashboard displays, in accordance with an exemplary embodiment of the present invention.

DETAILED DESCRIPTION

Figure 1:
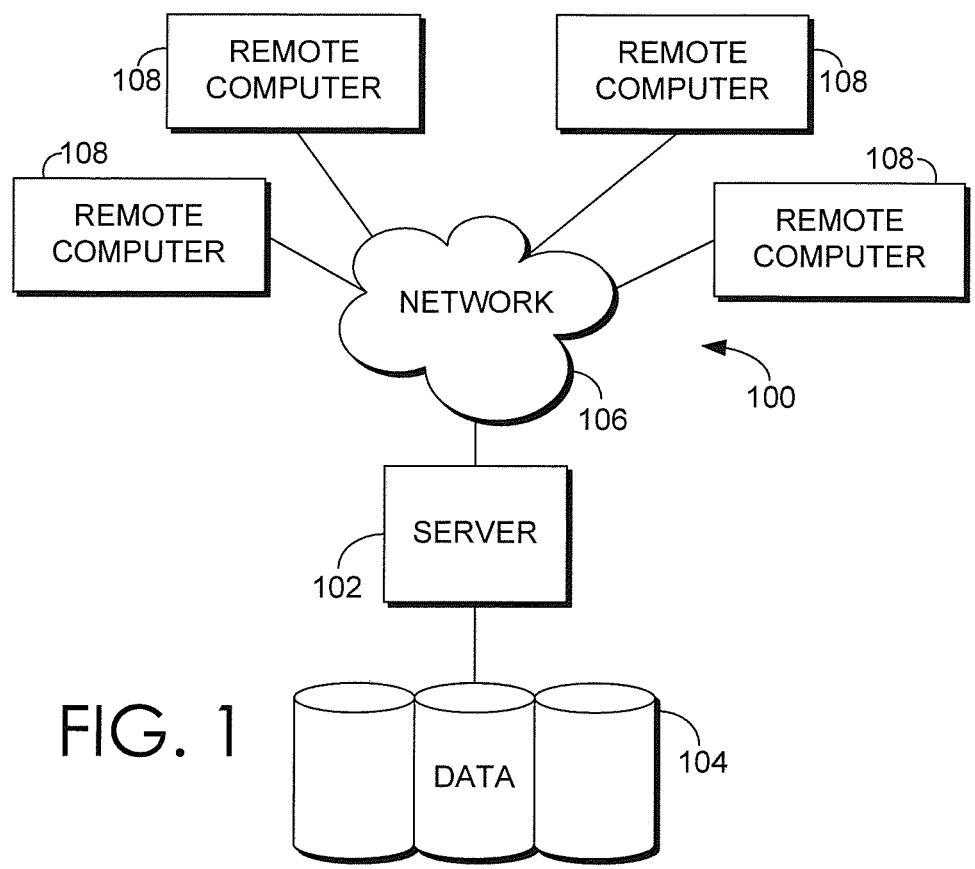
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for, among other things, providing an emergency department ("ED") centralized interactive display. The ED centralized interactive display provides an ED clinician an efficient one-stop shop for performing ED duties. Embodiments are also directed to methods, systems, and computer-readable media for, among other things, providing an interactive ED dashboard display, which may reflect an overall performance of the ED with respect to various performance metrics.

Accordingly, one embodiment of the present invention is directed to one or more computer hardware storage media storing computer-useable instructions that, when used by one or more computing devices, cause the one or more computing devices to perform a method of providing an ED centralized interactive display. The method may include providing a segmentable summary of patients within an ED. The segmentable summary may allow a clinician to view a specific area within the ED or a summary of patients assigned to the clinician including unassigned patients sorted by acuity and length of stay. A throughput summary for a patient may be provided that indicates throughput and whether actions are pending for the patient. The throughput may indicate whether the patient is pending arrival, waiting for a clinician, an exam has been completed, orders are pending, orders are completed, the patient is ready for discharge, and/or the patient is pending admission. A patient summary for the patient may be provided that includes information collected at triage, links to documentation from previous visits, care plans, a do not resuscitate order, home medications, and/or history. A provider summary is provided that provides information regarding providers for the patient and allows the clinician to designate an attending physician to the patient.

Another embodiment of the present invention includes a system for providing an ED centralized interactive display. The system includes one or more processors coupled to a computer storage medium, the computer storage medium having stored thereon a plurality of computer software components executable by the processor. The computer software components may include a patient summary component that provides a patient summary for a patient. The patient summary may include information collected at triage, links to documentation from previous visits, care plans, a do not resuscitate order, home medications, and/or history. A provider summary component may provide a provider summary. The provider summary may provide information regarding providers for the patient and allow the clinician to designate an attending physician to the patient. A vitals summary component may provide a vitals summary that indicates the most recent vitals measurements and further indicates if any vital readings are stale, critical and/or have not been reviewed, or if no vital readings are available. A medications summary component may provide a medications summary that indicates medications that have been ordered or administered to the patient and allows the clinician to place new orders directly from an orders hover window associated with the medications summary and without having to go into a chart associated with the patient. A laboratory summary component may provide a medications summary that indicates medications that have been ordered for or administered to the patient. The medications summary may further allow the clinician to place new orders directly from an orders hover window associated with the medications summary and without having to go into a chart associated with the patient. An electrocardiogram ("EKG") summary component may provide an EKG summary that provides details of EKG orders, a status of the EKG, and/or a link to the EKG results. An images summary component may provide an images summary that provides a status of an order for an image, order details, a link to the image, a status of documentation for the image, and/or a link to provide documentation after the image is read. A length of stay summary component may provide a length of stay summary that indicates a status associated with a length of stay and includes a timer to alert the clinician if a threshold has been exceeded for the patient. A documentation summary component may provide a documentation summary that indicates a status associated with documentation for the patient and enables the clinician to update the documentation. An acuity summary component may provide an acuity summary for the patient that indicates an acuity for the patient.

Yet another embodiment of the present invention is directed to computer storage media having computer-executable instructions embodied thereon that, when executed by one or more computing devices, cause the one or more computing devices to produce a graphical user interface (GUI) for providing an ED centralized interactive display. The GUI may include a segment display area that displays a view of a specific area within the ED or a summary of patients assigned to the clinician including unassigned patients sorted by acuity and length of stay. An acuity display area may display an acuity for the patient. The acuity may be color coded based on severity. A throughput display area may display throughput for a patient and indicate whether actions are pending for the patient. The throughput may indicate whether the patient is waiting for a clinician, an exam has been completed, orders are pending, orders are completed, the patient has been discharged, and/or the patient is pending admission. A patient display area may display information collected at triage, links to documentation from previous visits, care plans, a do not resuscitate order, home medications, and/or history. A provider display area may display information regarding providers for the patient and allows the clinician to designate an attending physician to the patient. The provider display area may include placeholders for specific clinician positions to maintain uniformity for the provider display area for each patient. A consult display area may display whether a consult has been requested and allows the clinician to initiate the consult. An orders/vitals display area may display an order summary that indicates a status associated with orders for the patient and a vitals summary that indicates the most recent vitals measurements, displays alerts to the clinician if any vital readings are stale, displays alerts to the clinician if any vital readings are critical and have not been reviewed, or displays alerts to the clinician if no vital readings are available.

Another embodiment of the present invention includes computer storage media having computer-executable instructions embodied thereon that, when executed by one or more computing devices, cause the one or more computing devices to perform a method for presenting an interactive ED dashboard display for an ED at a user computing device. The method may include presenting a plurality of user interface indicators on the interactive ED dashboard display at the user computing device. Each of the plurality of user interface indicators may correspond to a real-time performance metric for the ED, where the real-time performance metric is based on patient data for a plurality of patients in the ED. A user input may be received at the user computing device. The user input may indicate a selection of one of the plurality of user interface indicators. In response to the user input, the method may include presenting, on the interactive ED dashboard display at the user computing device, the patient data that is associated with the real-time performance metric corresponding to the selected one of the plurality of user interface indicators.

Yet another embodiment of the present invention includes a computer system for providing an interactive ED dashboard display for an ED. The computer system may include one or more processors and one or more computer storage media storing computer-useable instructions that, when used by the one or more processors, cause the one or more processors to perform a number of steps. For example, the one or more processors may present a plurality of user interface indicators corresponding to a plurality of real-time performance metrics for the ED. The plurality of real-time performance metrics may be based on patient data for a plurality of patients in the ED. The one or more processors may receive a user input indicating a selection of one of the plurality of user interface indicators. The selected one of the plurality of user interface indicators may correspond to one of the plurality of real-time performance metrics. Additionally, the one or more processors may present a subset of the patient data that is associated with the one of the plurality of real-time performance metrics.

An additional embodiment of the present invention includes computer storage media having computer-executable instructions embodied thereon that, when executed by one or more computing devices, cause the one or more computing devices to generate a GUI corresponding to an interactive ED dashboard display for an ED at a user computing device. The GUI may include a user interface indicator display area on the interactive ED dashboard display at the user computing device. The user interface indicator display area may display a plurality of user interface indicators, where each of the plurality of user interface indicators corresponds to a real-time performance metric for the ED. The real-time performance metric may be based on patient data for a plurality of patients in the ED. The user interface indicator display area may include a selectable real-time length of stay indicator that indicates a length of stay associated with the plurality of patients in the ED, a selectable real-time acuity indicator that indicates an acuity associated with the plurality of patients in the ED, a selectable real-time critical patient indicator that indicates a first subset of the plurality of patients in the ED that is associated with a critical status, a selectable real-time staffing indicator that indicates staffing assignments for the plurality of patients in the ED, a selectable real-time volume indicator that indicates a patient volume and a resource volume associated with the ED, a selectable real-time waiting room indicator that indicates a wait time associated with a waiting room for the ED, a selectable real-time pending admissions indicator that indicates a second subset of the plurality of patients in the ED that is pending admission, and a selectable real-time order indicator that indicates orders associated with the plurality of patients in the ED.

Turning now to the figures, an exemplary computing environment suitable for use in implementing embodiments of the present invention is described. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes therein, or has access to, a variety of computer-readable media, including non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media include both volatile and nonvolatile, removable and non-removable media implemented in any method or technology for storage of information such as computer-readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency ("RF"), infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, a user might enter commands and information into the control server 102 or convey the commands and information to the control server 102 via one or more of the remote computers 108 through input devices, such as a keyboard, a touch screen, a pointing device (commonly referred to as a mouse), a trackball, or a touch pad. Other input devices may include, without limitation, microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
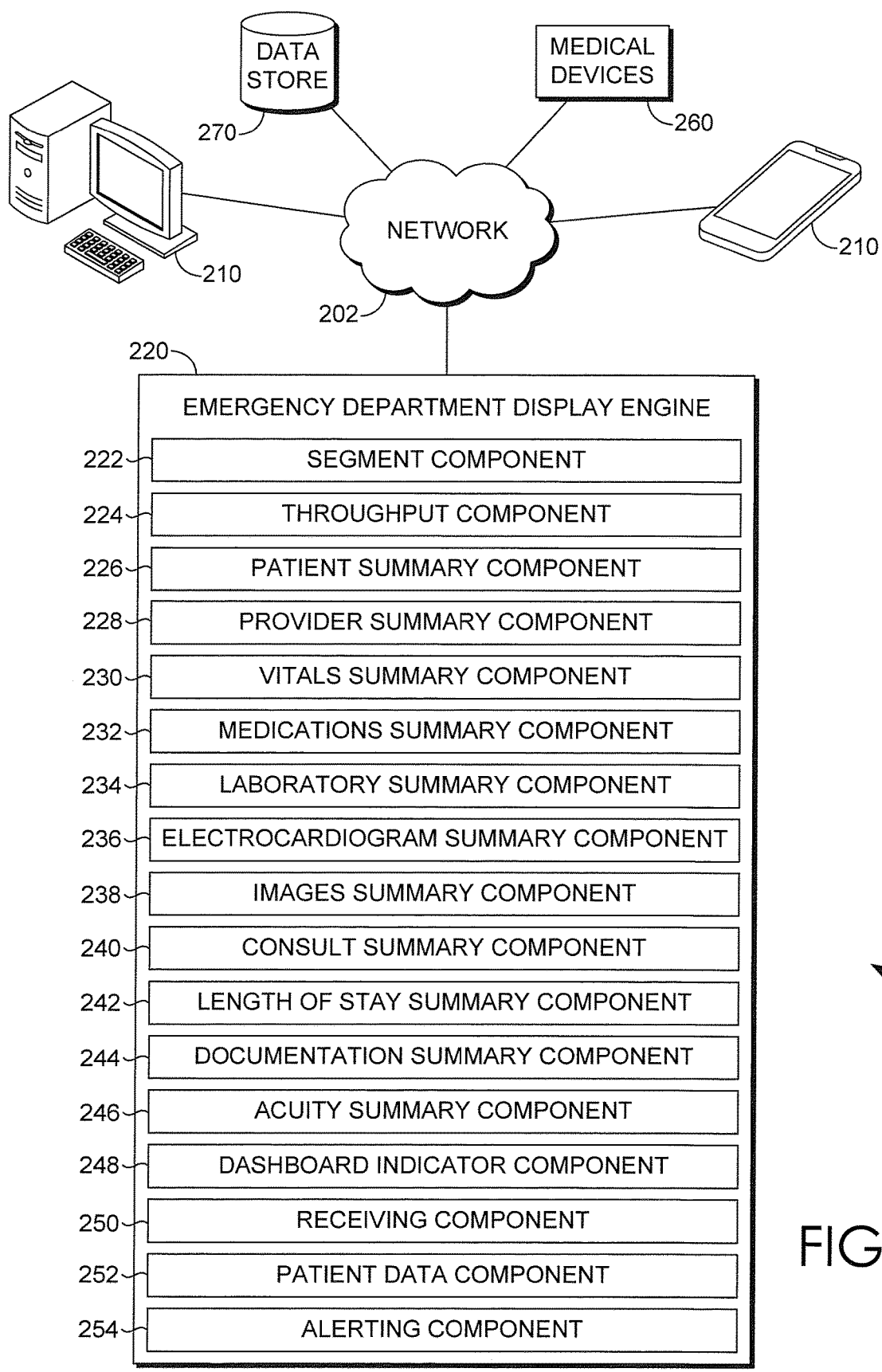
FIG. 2 is a block diagram of an exemplary system for providing an emergency department centralized interactive display, in accordance with exemplary embodiments of the present invention.

Turning now to FIG. 2, an exemplary computing system environment 200 suitable to implement embodiments of the present invention is illustrated. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The exemplary computing system environment 200 may include one or more display devices 210 (e.g., computer, mobile device, and the like), an emergency department display engine ("ED display engine") 220, medical devices 260, and a data store 270, all of which are in communication with one another via a network 202. The network 202 may resemble the network 106 of FIG. 1, and may include, without limitation, one or more secure local area networks (LANs) or wide area networks (WANs). The network 202 may further include a cloud computing network, such as a public cloud, a private cloud, or a dedicated cloud. These cloud computing networks may be referred to as "the cloud." The network 202 may be a secure network associated with a facility such as a healthcare facility. The secure network 202 may require that a user log in and be authenticated in order to send and/or receive information over the network 202.

The ED display engine 220 may include various components/modules. In addition to the components illustrated, the ED display engine 220 may include a processing unit, internal system memory, and a suitable system bus for coupling various system components, including one or more data stores for storing information (e.g., files and metadata associated therewith). The ED display engine 220 may include, or may have access to, a variety of computer-readable media. In some embodiments, one or more of the illustrated components/modules may be implemented as stand-alone applications. In other embodiments, one or more of the illustrated components/modules may be distributed across multiple ED display engines 220. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the ED display engines 220 might reside on a server, cluster of servers, or a computing device remote from one or more of the remaining components. Thus, while the ED display engine 220 is illustrated as a single unit, it will be appreciated that the ED display engine 220 is scalable and may in actuality include a plurality of computing devices in communication with one another. The single unit depictions are meant for clarity, not to limit the scope of embodiments in any form.

The data store 270 is configured to store information for use by, for example, the ED display engine 220. The information stored in association with the data store 270 is configured to be searchable for one or more items of information stored in association therewith. The information stored in association with the data store 270 may comprise information used by various components of the ED display engine 220.

The data store 270 may store electronic medical records (EMRs) of patients associated with one or more healthcare facilities. EMRs may comprise electronic clinical documents such as images, clinical notes, orders, summaries, reports, analyses, information received from medical devices 260, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information.

The data store 270 may further store historical performance data for the ED. For example, performance data providing a snapshot of the ED performance at a particular moment in time may be stored. As will be described below, such historical performance data may be used by the ED dashboard for predictive purposes. Performance thresholds, such as target and critical performance thresholds may also be stored at the data store 270.

The content and volume of such information in the data store 270 are not intended to limit the scope of embodiments of the present invention in any way. Further, though illustrated as a single, independent component, the data store 270 may, in fact, be a plurality of storage devices, for instance, a database cluster.

The display devices 210 may be any type of display device capable of communicating on the network 202 with the ED display engine 220, the data store 270, and/or the medical devices 260. Such devices may include any type of mobile and portable devices, including cellular telephones, personal digital assistants, tablet PCs, smart phones, and the like.

The display of the display device 210 may be configured to display information to the user of the display device 210. The information may include communications initiated by and/or received by the ED display engine 220. Embodiments are not intended to be limited to visual display, but rather may also include audio presentation, combined audio/visual presentation, and the like.

The computing system environment 200 is merely exemplary. It should be understood that this and other arrangements described herein are set forth only as examples. Other arrangements and elements (e.g., machines, interfaces, functions, orders, and groupings of functions) can be used in addition to, or instead of, those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

As shown in FIG. 2, the ED display engine 220 comprises, in various embodiments, a segment component 222, a throughput component 224, a patient summary component 226, a provider summary component 228, a vitals summary component 230, a medications summary component 232, a laboratory summary component 234, an electrocardiogram summary component 236, an images summary component 238, a consult summary component 240, a length of stay summary component 242, a documentation summary component 244, an acuity summary component 246, a dashboard indicator component 248, a receiving component 250, a patient data component 252, and an alerting component 254. In some embodiments, one or more of the components may be implemented as stand-alone applications. It will be understood that the components illustrated in FIG. 2 are exemplary in nature and in number and should not be construed as limiting. Any number of components may be employed to achieve the desired functionality within the scope of embodiments hereof.

In one embodiment, the segment component 222 provides a segmentable summary of patients within an ED. The segmentable summary may allow a clinician to view a specific area within the ED. The segmentable summary may allow a clinician to view a summary of patients assigned to the clinician. The summary may include unassigned patients sorted by acuity and length of stay.

In one embodiment, the throughput component 224 provides a throughput summary for a patient that indicates throughput and whether actions are pending for the patient. The throughput may indicate whether the patient is pending arrival. The throughput may indicate whether the patient is waiting for a clinician. The throughput may indicate whether an exam has been completed. The throughput may indicate whether orders are pending or completed. The throughput may indicate whether the patient is ready for discharge. The throughput may indicate whether the patient is pending admission.

In embodiments, the patient summary component 226 provides a patient summary for a patient. The patient summary includes information collected at triage, links to documentation from previous visits, care plans, a do not resuscitate order, home medications, and/or history. The patient summary component 226 may further provide a chief complaint provided by the patient, as well as any accompanying notes or comments.

The provider summary component 228 may provide a provider summary. In one example, the provider summary provides information regarding providers for the patient. The provider summary may further allow the clinician to designate an attending physician to the patient. To maintain uniformity for the provider summary, provider summary component 228 may provide placeholders for specific clinician positions.

In embodiments, the vitals summary component 230 provides a vitals summary that indicates the most recent vitals measurements. The vitals summary may further indicate if any vital readings are stale, critical and/or have not been reviewed, or if no vital readings are available. The vitals summary component 230 may also allow the clinician to place new orders directly from an orders hover window associated with the vitals summary without having to go into a chart associated with the patient.

The medications summary component 232 may provide a medications summary. The medications summary may indicate medications that have been ordered or administered to the patient. The medications summary may further allow the clinician to place new orders directly from an orders hover window associated with the medications summary without having to go into a chart associated with the patient.

The laboratory summary component 234, in embodiments, provides a laboratory summary. The laboratory summary may indicate whether results are completed, whether the results are overdue, whether the results have been reviewed, and may further allow the clinician to review the results directly from a results hover window associated with the laboratory summary and without having to go into the chart associated with the patient.

The electrocardiogram summary component 236 may provide an EKG summary. The EKG summary may provide details of EKG orders, a status of the EKG, and/or a link to the EKG results. Images summary component 238 may provide an images summary that provides a status of an order for an image, order details, a link to the image, a status of documentation for the image, and/or a link to provide documentation after the image is read.

In one embodiment, consult summary component 240 provides a consult summary that indicates whether a consult has been requested and allows the clinician to perform the consult.

The length of stay summary component 242 may provide a length of stay summary that indicates a status associated with a length of stay and includes a timer to alert the clinician if a threshold has been exceeded for the patient. The status may be the status provided by the throughput component 224. The timer may count upwards or downwards to help the facility track the time required at each status for the patient.

The documentation summary component 244, in embodiments, provides a documentation summary that indicates a status associated with documentation for the patient and enables the clinician to update the documentation. For example, the documentation summary component 244 may indicate that documentation has not been started (e.g., blank), documentation is in progress (e.g., filled), documentation is complete (e.g., filled with check), a multi-contributor document is complete (e.g., filled with green "chat" icon), or a multi-contributor document is not complete (e.g., filled with red "chat" icon). The documentation summary component 244 may further allow a clinician to provide additional documentation, such as by selecting a button or otherwise interacting with the display. This may allow the clinician to provide documentation without opening another application or an EMR associated with the patient.

The acuity summary component 246 may provide an acuity summary for the patient that indicates an acuity for the patient. As used herein, "acuity" may refer to the severity of a patient condition. A numerical acuity rating may be assigned to a patient based on any number of factors that reflect the severity of the patient's condition, such as the clinician staffing needed to care for the patient. In some instances, an acuity of 1 corresponds to the most severe condition, while an acuity of 5 corresponds to the least severe condition. The acuity summary may be color coded based on severity. The acuity summary may further have a numerical indicator providing the clinician additional information regarding the severity. The color coding and the numerical identifier may serve as a visual triage indicator allowing the clinician to quickly identify the patient in the most urgent need of attention. For example, the color may be a lighter shade for a severity of 5, indicating to the clinician that the acuity is not currently severe. A darker color, such as a bright red, may be utilized for a severity of 1, indicating to the clinician that the acuity is very severe.

In addition to the components described above, which may provide, among other things, information for particular patients within the ED, the ED display engine 220 may also include a dashboard indicator component 248, which may provide an interactive ED dashboard display that reflects an overall performance of the ED with respect to various performance metrics. In particular, the dashboard indicator component 248 may provide user interface indicators corresponding to real-time performance metrics for the ED. Such a dashboard may allow a clinician to quickly determine whether ED operations are running smoothly and identify problem areas to be addressed. The various indicators that may be included in the ED dashboard display that is provided by the dashboard indicator component 248 will be discussed with respect to FIGS. 32-37. The patient data that is associated with the real-time performance metrics for the ED may be presented by the patient data component 252. For example, the patient data component 252 may present the various types of patient data discussed above and may filter such data based on a particular performance metric.

The ED display engine 220 may further include a receiving component 250 that receives user input. For example, user input may be provided at a user computing device (e.g., display device 210), such as through the input means discussed with respect to the remote computers 108 of FIG. 1, and an indication of the user input may then be received by the receiving component 250. A user input might indicate a selection of one of the indicators included in the ED dashboard display that is provided by the dashboard indicator component 248.

Finally, the ED display engine 220 may include an alerting component 254. The alerting component 254 may be configured to provide an alert. The alert may include a visual alert, audible alert, and/or other sensory alert. Such alert may be presented at a user computing device, such as the display device 210. The alert may be presented in response to determining that a real-time performance metric has satisfied a performance threshold, such as a critical performance threshold. This will be discussed in more detail below.

Other components not shown in FIG. 2 may also be included in the ED display engine 220. For example, a customization component may allow a user to customize a presentation of user interface indicators on the ED dashboard display.

Turning now to FIGS. 3-37, exemplary screen displays are illustrated in accordance with embodiments of the present invention. These screen displays may be generated by the ED display engine 220 of FIG. 2. The exemplary screen displays may be presented on the display devices 210 of FIG. 2. As described in more detail below, the exemplary screen displays are interactive, and dynamic features associated with the exemplary screen displays may be triggered by user input received at the display devices 210 of FIG. 2. It is understood that each of the illustrative screen displays may be connected logically in order to provide a cohesive interactive user interface. The screen displays may appear in any order and with any number of screen displays, without regard to whether the screen display is described or depicted herein.

FIGS. 3-27 include exemplary ED centralized interactive displays, where the information presented includes data associated with particular patients. For example, these screen displays may provide a streamlined view of a patient and a status of the patient within the ED. In one embodiment, a first portion of screen displays provides information about the patient and why the patient is in the ED. In one embodiment, a second portion of screen displays provides information on physician interventions and a progress associated with the physician interventions. In one embodiment, a third portion of screen displays provides a throughput indicating the position or status of the ED visit and the items that need to be completed for the patient to be discharged or admitted. As mentioned, these various portions of screen displays may be generated by the ED display engine 220 of FIG. 2 and may be presented on the display devices 210 of FIG. 2. The information included in the displays, as well as the data used to generate the information included in the displays, may be stored at the data store 270 of FIG. 2.

FIGS. 28-37 include an exemplary ED dashboard display, which reflects an overall performance of the ED with respect to various performance metrics, as well as patient data associated with those performance metrics. Again, the exemplary ED dashboard displays may be generated by the ED display engine 220 of FIG. 2 and may be presented on the display devices 210 of FIG. 2. Information pertaining to the performance metrics and patient data, as well as any other information relevant to the ED dashboard displays, may be stored at the data store 270 of FIG. 2. As mentioned, FIGS. 3-37 may together comprise an interactive user interface for the ED.

Figure 3:
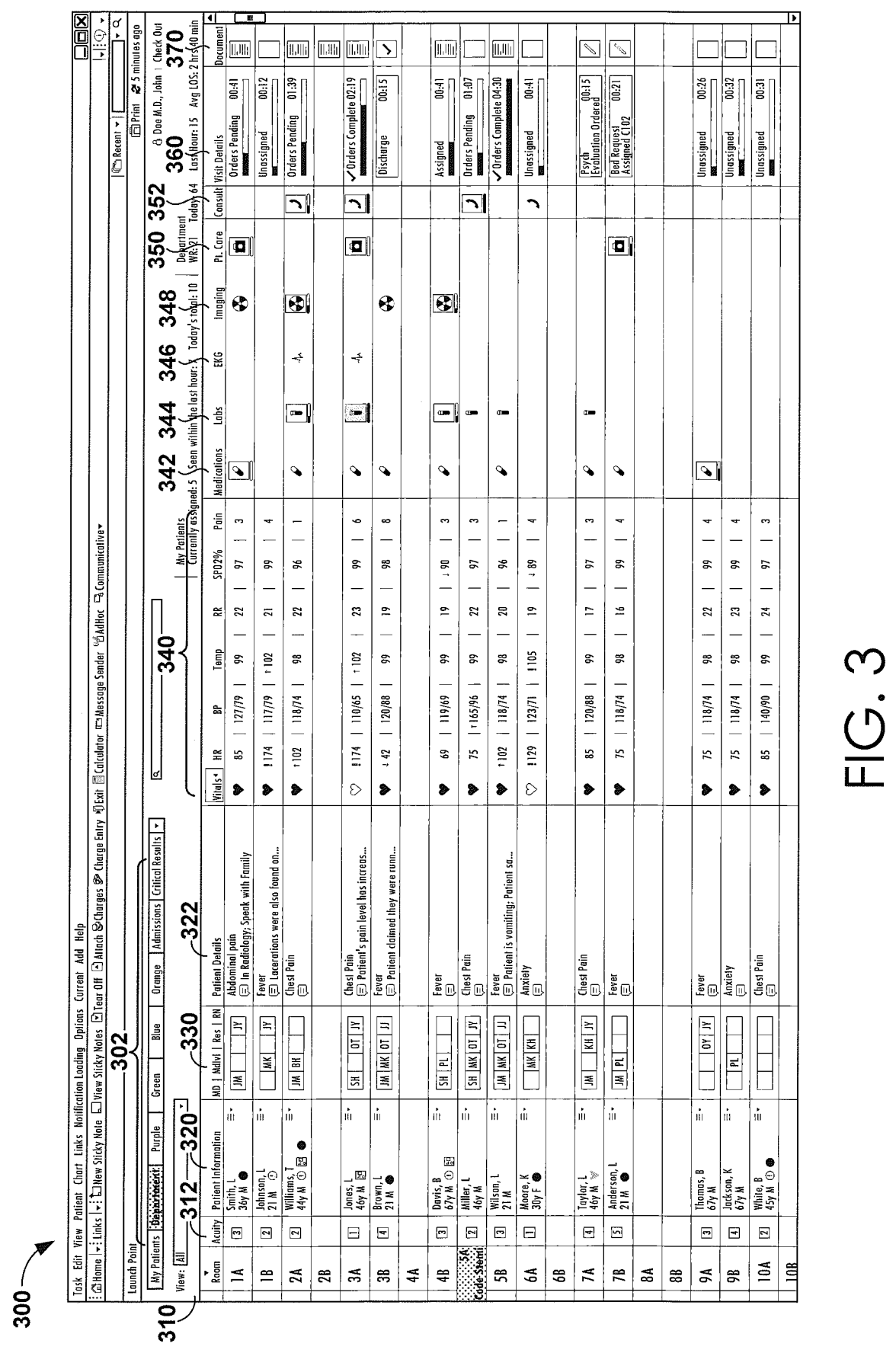

Beginning with FIG. 3, an illustrative screen display 300 of an embodiment of the present invention is shown. A segment display area 302 may display a view of a specific area within the ED or a summary of patients assigned to the clinician including unassigned patients sorted by acuity and length of stay. The segment display area 302 may allow the clinician to control the desired view, such as by selecting the desired area or summary.

A throughput display area 310 may display throughput for a patient and indicate whether actions are pending for the patient. In one embodiment, the throughput indicates whether the patient is pending arrival. In one embodiment, the throughput indicates whether the patient is waiting for a clinician. In another embodiment, the throughput indicates an exam has been completed. In another embodiment, the throughput indicates orders are pending. In another embodiment, the throughput indicates orders are completed. In another embodiment, the throughput indicates the patient is ready for discharge. In another embodiment, the throughput indicates the patient is pending admission. In one embodiment, a light presented within the throughput display area 310 indicates actions are pending for the patient.

An acuity display area 312 may display an acuity for the patient. The acuity may be color coded based on severity. The acuity may further have a numerical indicator providing the clinician additional information regarding the severity. The color coding and the numerical indicator may serve as a visual triage indicator allowing the clinician to quickly identify the patient in the most urgent need of attention. For example, the color may be a lighter shade for a severity of 5, indicating to the clinician that the acuity is not currently severe. A darker color, such as a bright red, may be utilized for a severity of 1, indicating to the clinician that the acuity is very severe. This color scheme is provided only as an example, and it will be appreciated that any color scheme is included within the scope hereof.

Provider display area 320 may display information regarding providers for the patient. Provider display area 320 may further allow a clinician to designate an attending physician to the patient. To maintain uniformity for the provider display area 320, provider display area 320 may include placeholders for specific clinician positions.

Patient display area 330 may display information associated with the patient. The information may include information collected at triage. The information may further include links to documentation from previous visits. The information may further include care plans, a do not resuscitate order, home medications, and/or history. The information and the links may allow a clinician to review pertinent information regarding the patient from the ED centralized interactive display without needing to open another application or open the patient's EMR. The information may further include a chief complaint provided by the patient, as well as any accompanying comments or notes.

An orders/vitals display area 340, 342, 344, 346, 348, 350, 352 may display an order summary and a vitals summary. If a column in the orders/vitals display area 340, 342, 344, 346, 348, 350, 352 is blank, that may indicate nothing has taken place for that particular order type. If an icon appears, in one embodiment, but with no color coding, that may indicate an order has taken place for that particular order type, and it is not yet overdue. If an icon appears, in one embodiment, with a glowing box, that may indicate the order for that particular type is overdue. If an icon appears, in one embodiment, with a grey color coding, that may indicate the order for that particular order type is completed with normal results that have not yet been reviewed. If an icon appears, in one embodiment, with a red color coding, that may indicate the order for that particular order type is completed with critical results that have not yet been reviewed. If an icon appears, in one embodiment, in the vitals column with a grey heart that may indicate the patient has normal vital signs. If an icon appears, in one embodiment, in the vitals column with a red heart that may indicate the patient has critical vital signs. As can be appreciated, any color coding or indication can be utilized to alert a clinician to any condition or status for any of the vitals or orders described herein. Status bars may further visually indicate a progress for all pending orders (i.e., number of items completed against the entire order for each order category) so the clinician can easily identify a percentage of items completed. The status bar may further utilize color coding or shading to indicate if new items that are critical or new items that have been completed and have not yet been reviewed or if a configurable threshold has passed since the order was placed indicating the order is taking too long to process or administer.

The vitals summary 340 may indicate the most recent vitals measurements, display alerts to the clinician if any vital readings are stale, display alerts to the clinician if any vital readings are critical and have not been reviewed, or display alerts to the clinician if no vital readings are available. The order summary may indicate a status associated with orders for the patient.

In one embodiment, the order summary includes a medications summary 342. The medications summary 342 may indicate medications that have been ordered or administered to the patient and allow the clinician to place new orders directly from an orders hover window associated with the medications summary and without having to go into a chart associated with the patient.

In one embodiment, the order summary includes a laboratory summary 344. The laboratory summary 344 may indicate whether results are completed, whether the results are overdue, and whether the results have been reviewed, and may further allow the clinician to review the results directly from a results hover window associated with the laboratory summary and without having to go into the chart associated with the patient.

In one embodiment, the order summary includes an EKG summary 346. The EKG summary 346 may provide details of EKG orders, a status of the EKG, and/or a link to the EKG results.

In one embodiment, the order summary includes an images summary 348 that may indicate a status of an order for an image. The images summary may further provide order details. A link to the image may be provided by the images summary that allows the clinician to open the image from the ED centralized interactive display without having to open another application. The images summary may further indicate a status of documentation for the image. The status may alert the clinician that documentation has been provided or that documentation is still needed. A link to provide documentation after the image is read may also be provided, thereby allowing the clinician to open a documentation window and provide documentation from the ED centralized interactive display without having to open another application.

In one embodiment, the order summary includes a patient care summary 350 that indicates a status of various tasks that have been ordered to care for the patient. These tasks may include tasks provided by any clinician assigned to the patient.

In one embodiment, the order summary includes a consult summary 352 that indicates a consult has been requested. The indication may allow the clinician to recognize when a patient has requested a consult. Further, the consult summary 352 may allow the clinician to initiate the consult, such as by clicking a button or otherwise interacting with the display.

In one embodiment, a length of stay display area 360 displays a status associated with a length of stay. The length of stay display area 360 may include a timer to alert the clinician if a threshold has been exceeded for the patient. The length of stay display area 360 may further be color coded as described herein with respect to other features and display areas of the ED centralized interactive display.

In one embodiment, a documentation display area 370 indicates a status associated with documentation for the patient. For example, the documentation display area 370 may indicate that documentation has not been started (e.g., blank), documentation is in progress (e.g., filled), documentation is complete (e.g., filled with check), a multi-contributor document is complete (e.g., filled with green "chat" icon), or a multi-contributor document is not complete (e.g., filled with red "chat" icon). The documentation display area 370 may further allow a clinician to provide additional documentation, such as by selecting a button or otherwise interacting with the display. This may allow the clinician to provide documentation without opening another application or an EMR associated with the patient.

Figure 4:
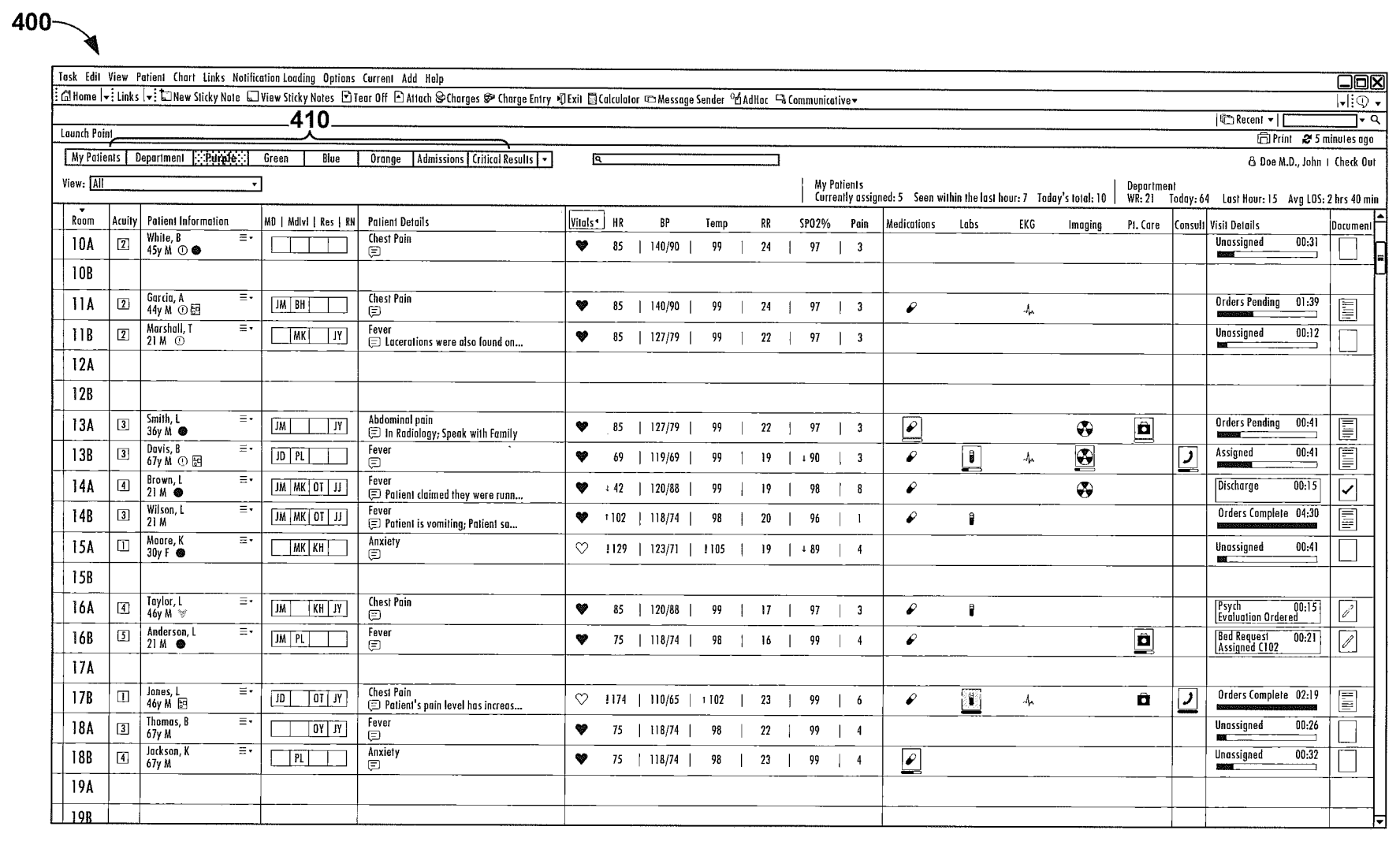

In FIG. 4, an illustrative screen display 400 of an embodiment of the present invention is shown. The segment display area 410 allows the clinician to control the desired view, such as by selecting the desired area or summary. In this example, the clinician can select between "My Patients," "Department," "Purple," "Green," "Blue," "Orange," "Admission," or "Critical Results." Upon selection, the desired view is displayed. As can be appreciated, the views can be configured or customized by each facility or clinician as desired.

Figure 5:
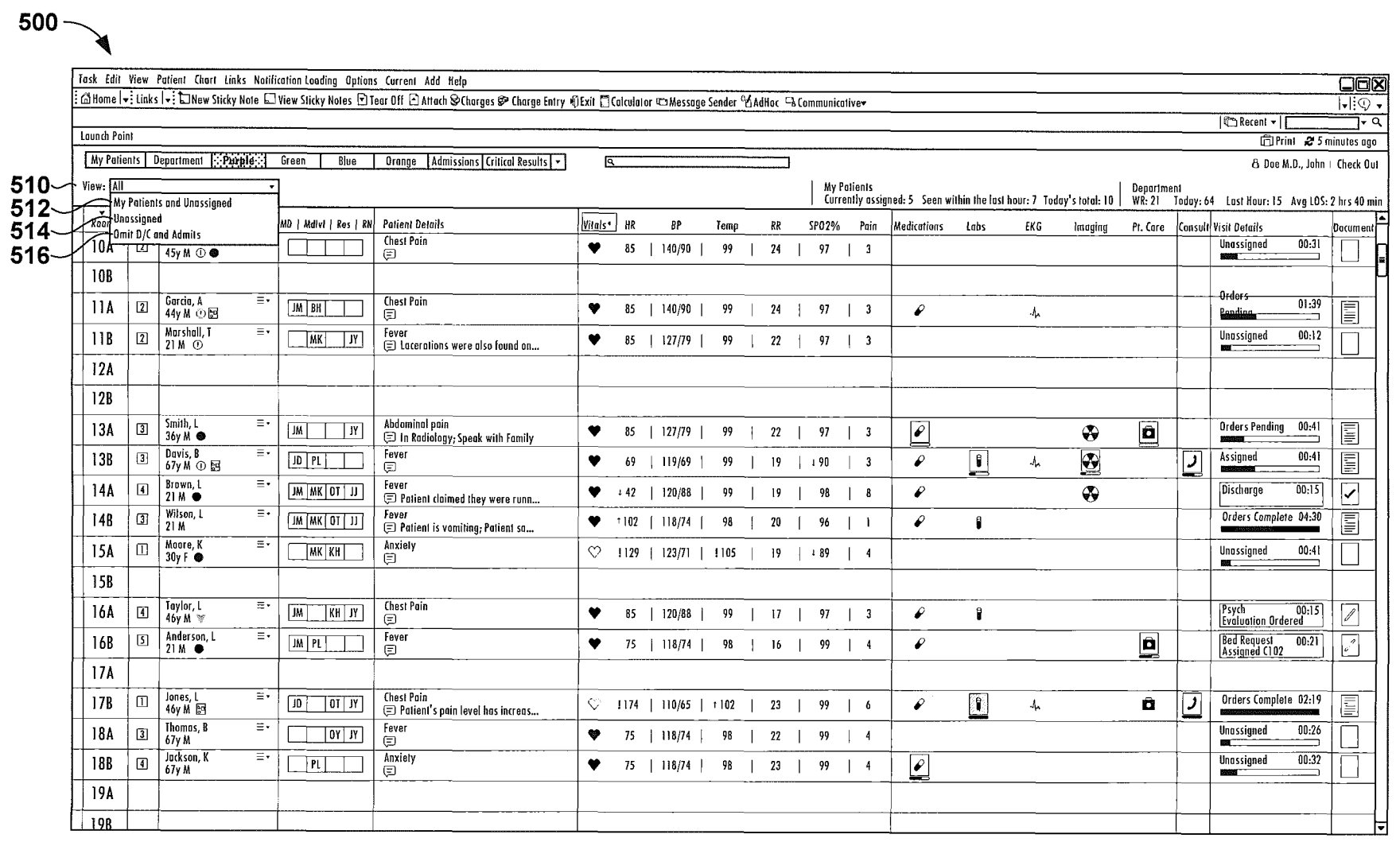

Turning now to FIG. 5, an illustrative screen display 500 of an embodiment of the present invention is shown. As illustrated, the desired view may further be selected by a dropdown menu 510. The dropdown menu 510 may contain more or additional views not available in the segment display area, such as customized views. In this example, the clinician can select "My Patients and Unassigned" 512, "Unassigned" 514, or "Omit D/C and Admits" 516.

Figure 6:
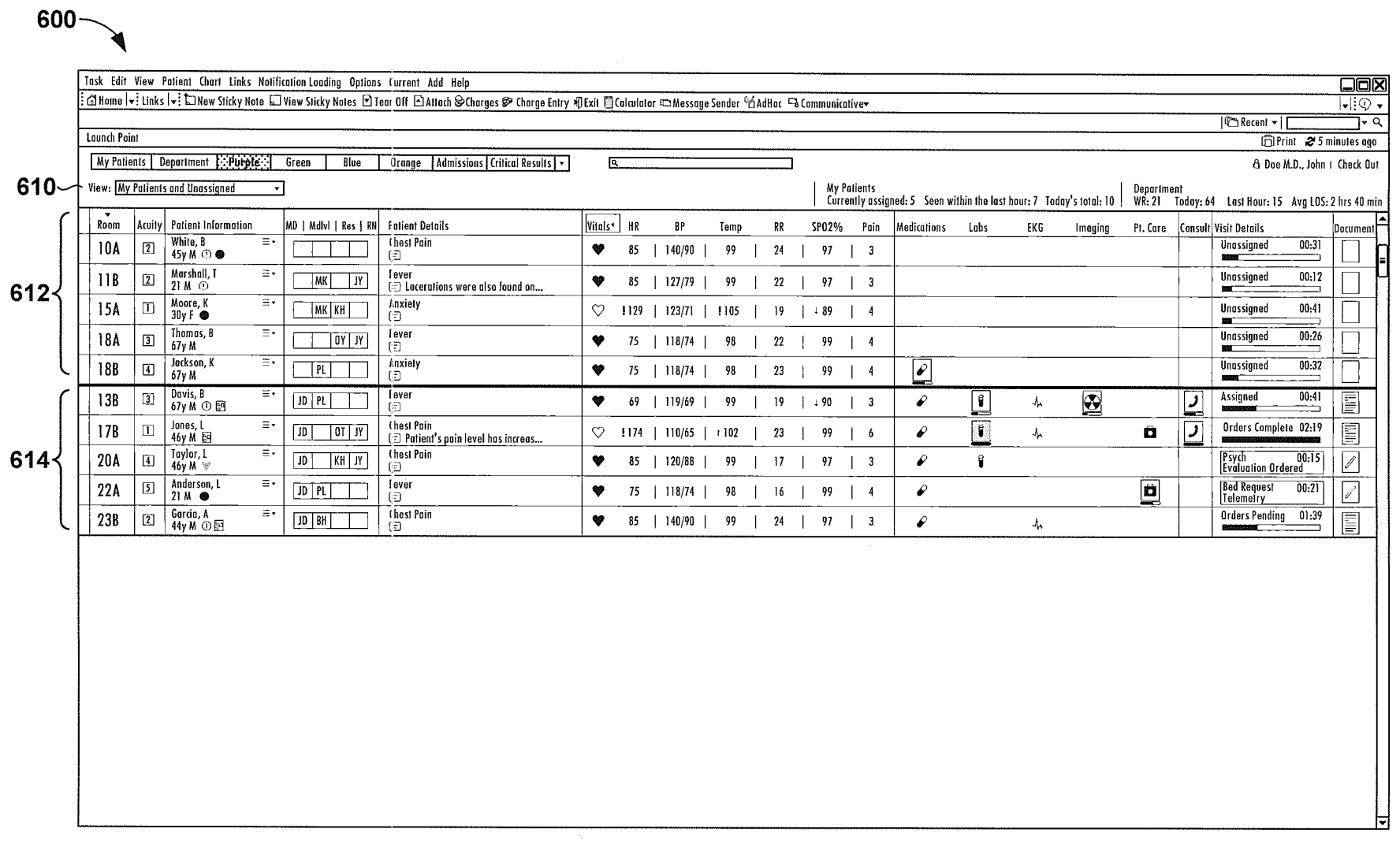

Referring now to FIG. 6, an illustrative screen display 600 of an embodiment of the present invention is shown. Continuing the example illustrated in FIG. 5, when the clinician selects "My Patients and Unassigned" 610, the unassigned patients 612 may be displayed and sorted by acuity and length of stay, so the most acute patient waiting for the longest time appears most prominently (e.g., at the top of the list). The patients 614 already assigned to the clinician may also be displayed.

Figure 7:
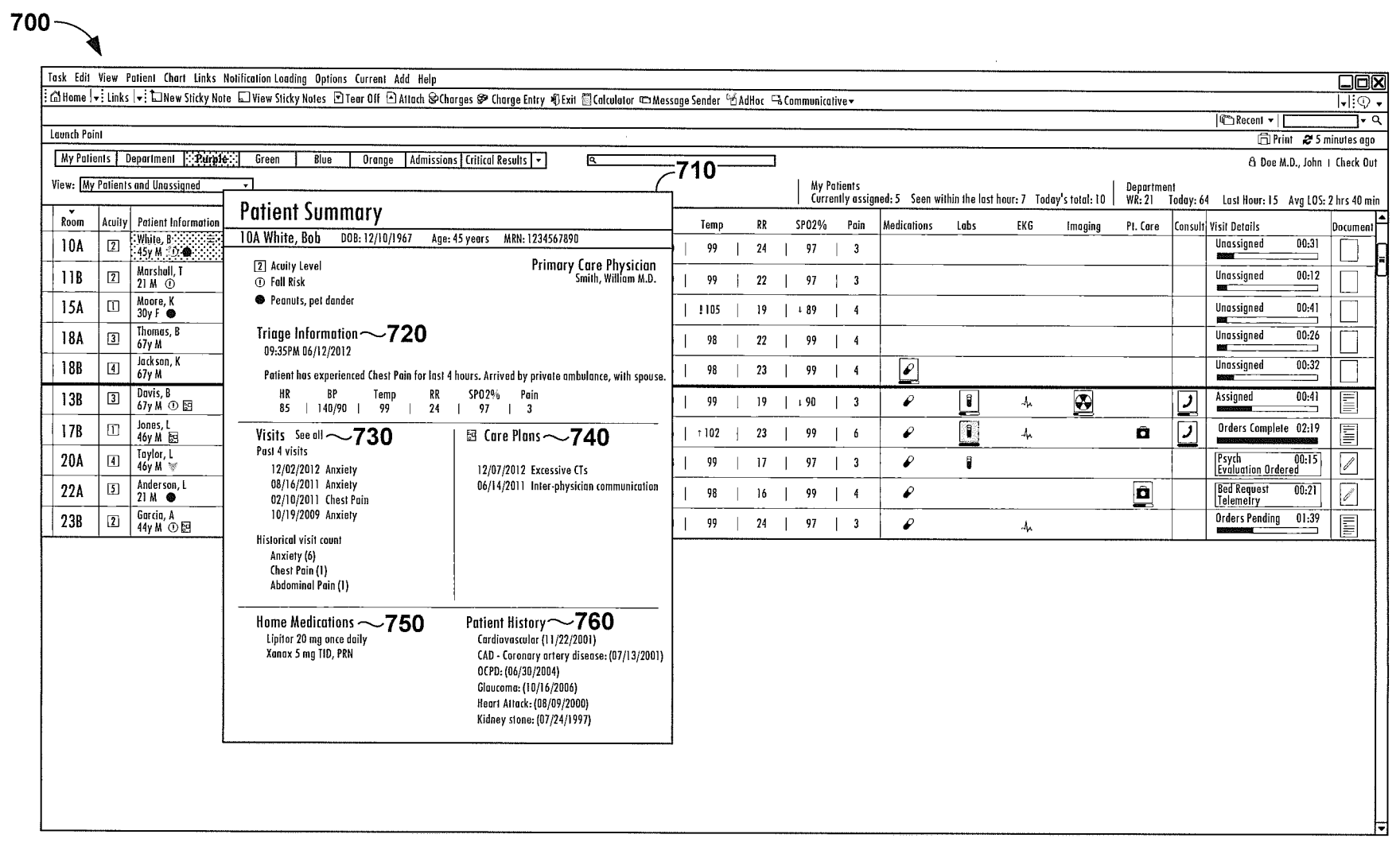

In FIG. 7, an illustrative screen display 700 of an embodiment of the present invention is shown. By interacting with a particular patient's name, the patient display area 710 is provided. The patient display area 710 displays information associated with the patient. The information may include information collected at triage 720. The information may further include links to documentation from previous visits 730. The information may further include care plans 740, a do not resuscitate order (not shown in FIG. 7), home medications 750, and/or history 760. The patient display area 710 may further provide links to documentation from current and past encounters (e.g., care plans/critical notes, physician notes, discharge summaries, etc.). The patient display area 710 is configurable so the desired links may be displayed. The information and the links may allow a clinician to review pertinent information regarding the patient from the ED centralized interactive display without needing to open another application or open the patient's EMR.

Figure 8:
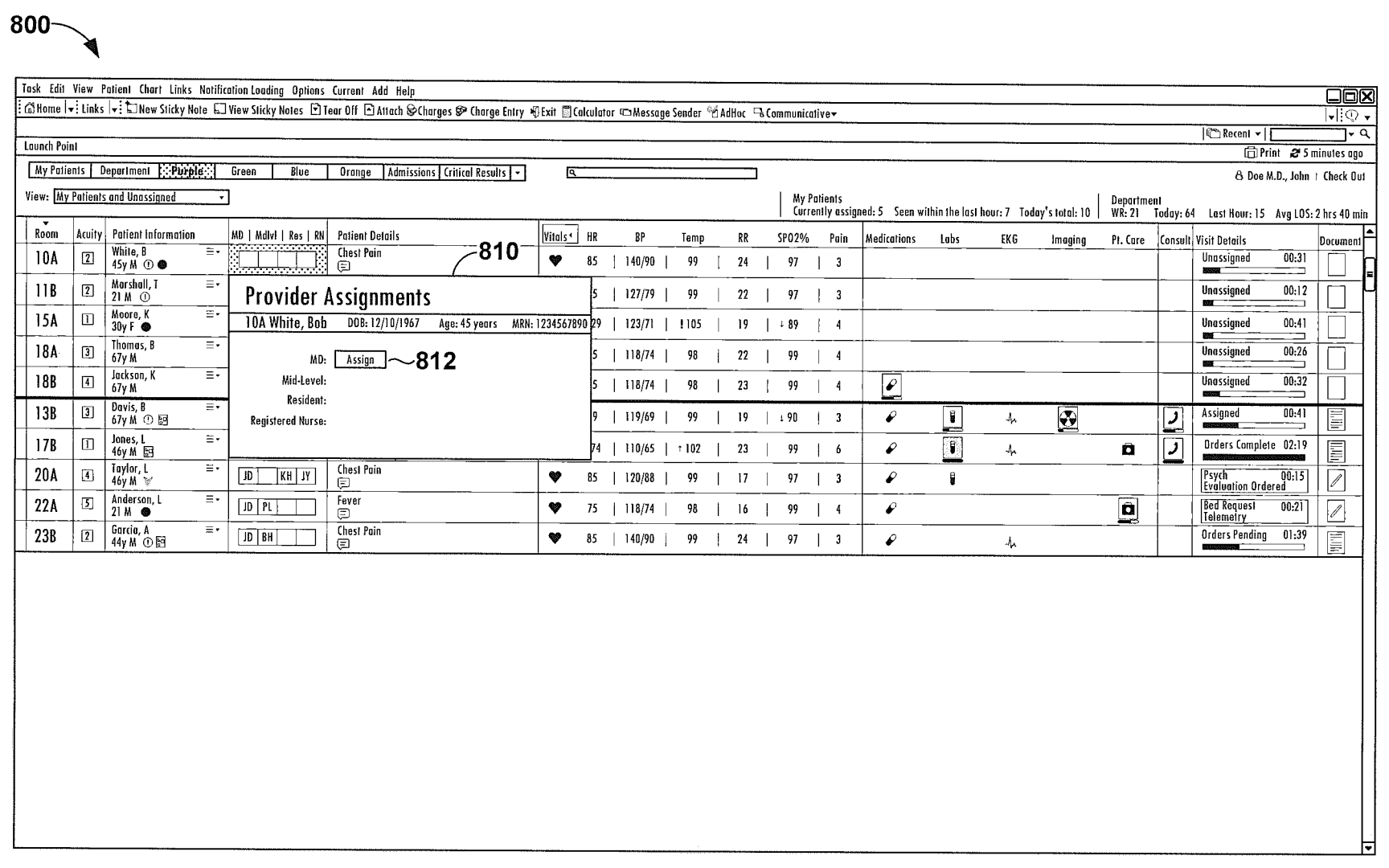

Turning now to FIG. 8, an illustrative screen display 800 of an embodiment of the present invention is shown. By hovering over or interacting with the provider display area for a particular patient, a provider assignment window 810 may be provided, allowing the clinician to designate (e.g., via an assign button 812) an attending physician for the patient.

Figure 9:
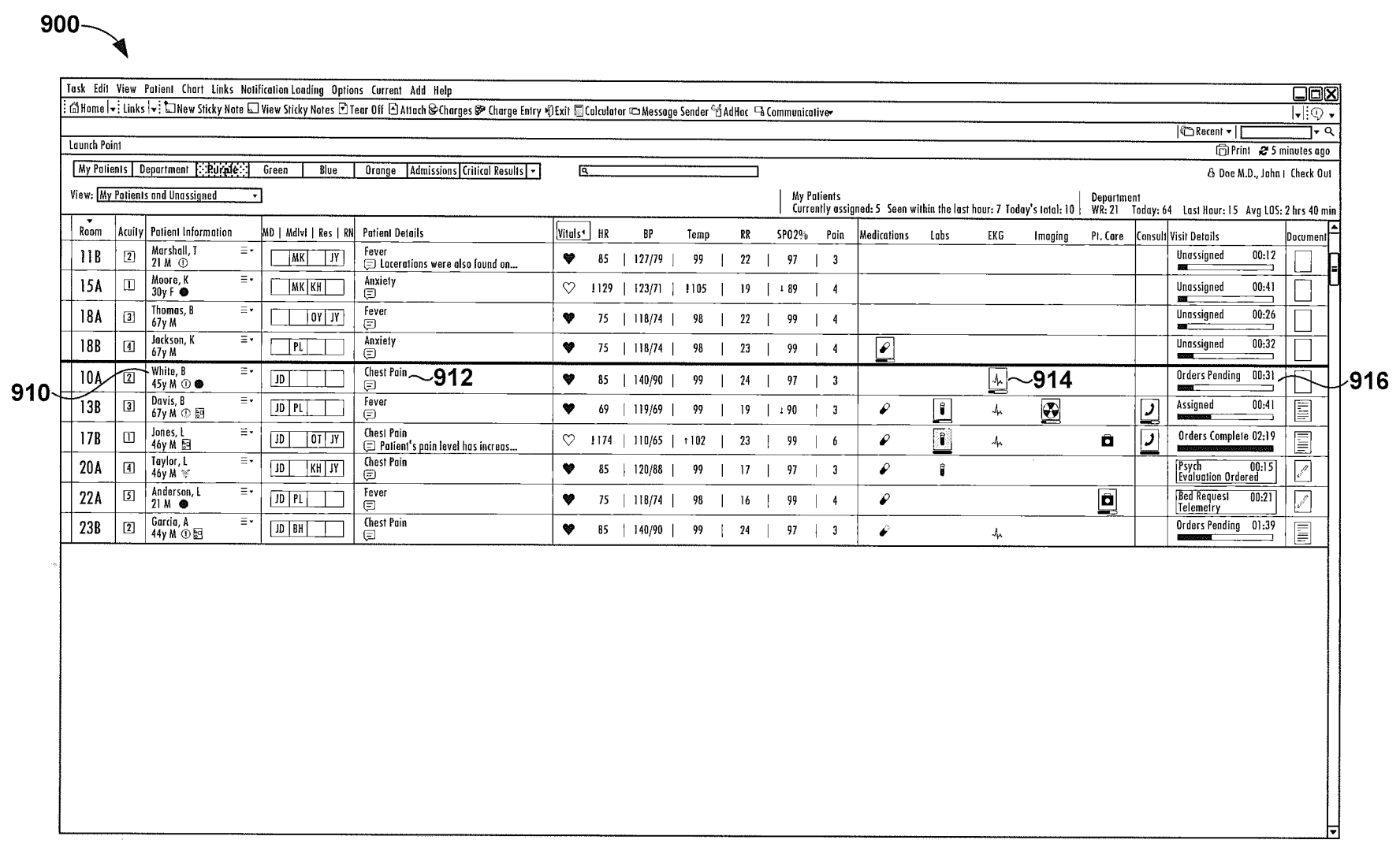

Referring now to FIG. 9, an illustrative screen display 900 of an embodiment of the present invention is shown. Continuing the example from FIG. 8, after the clinician selects to designate herself as the attending physician, the patient, "White, B." 910, may be moved to the clinician's "My Patients" area. The clinician's initials "JD" might now appear in the MD column 922 of the provider display area 920. Because the patient came in with chest pain, as illustrated by the chief complaint 912, an EKG order may be automatically placed, resulting in an EKG icon 914. The length of stay display area 916 may show that orders are pending, the progress of the orders, and the current time lapsed.

Figure 10:
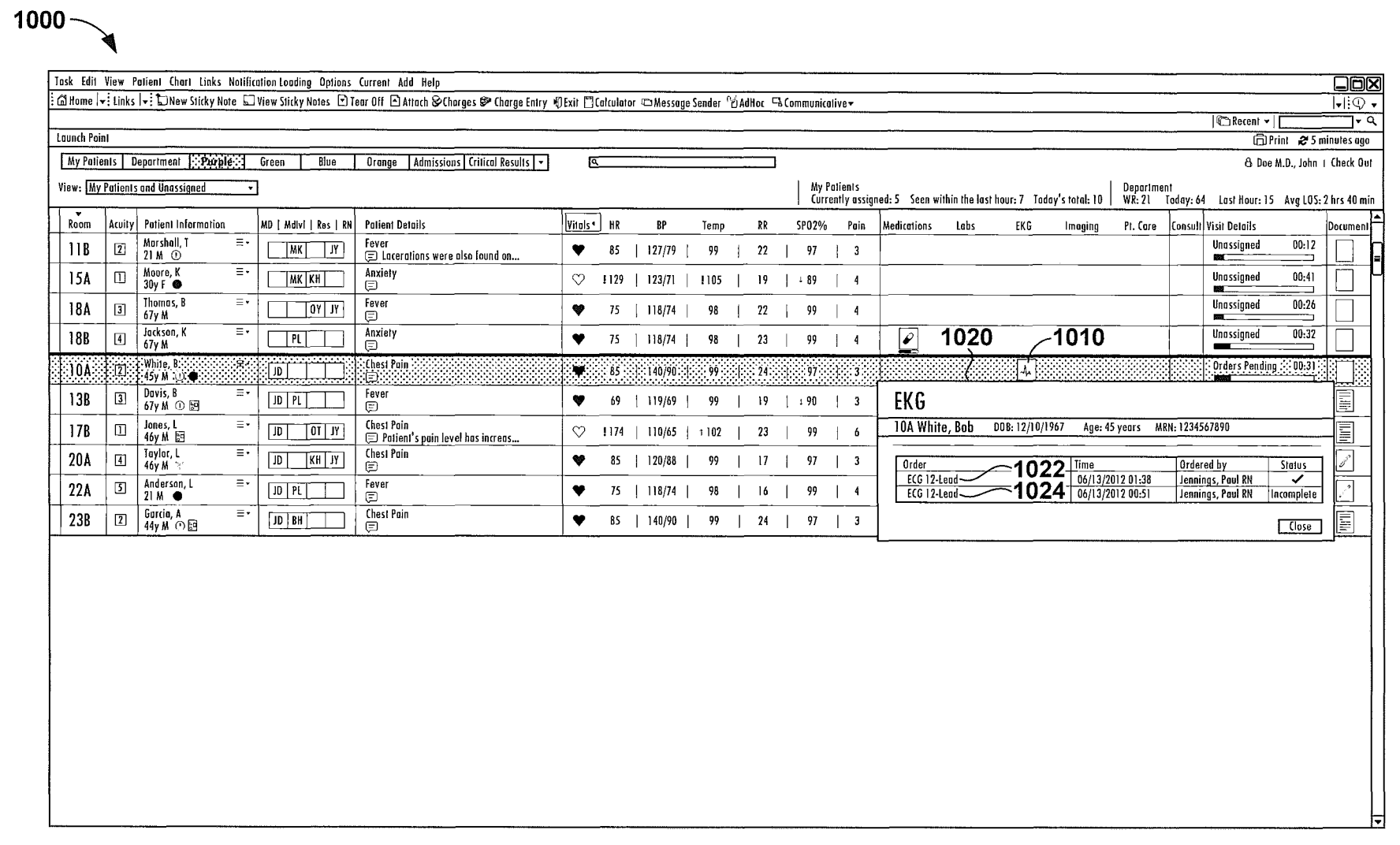
Figure 11:
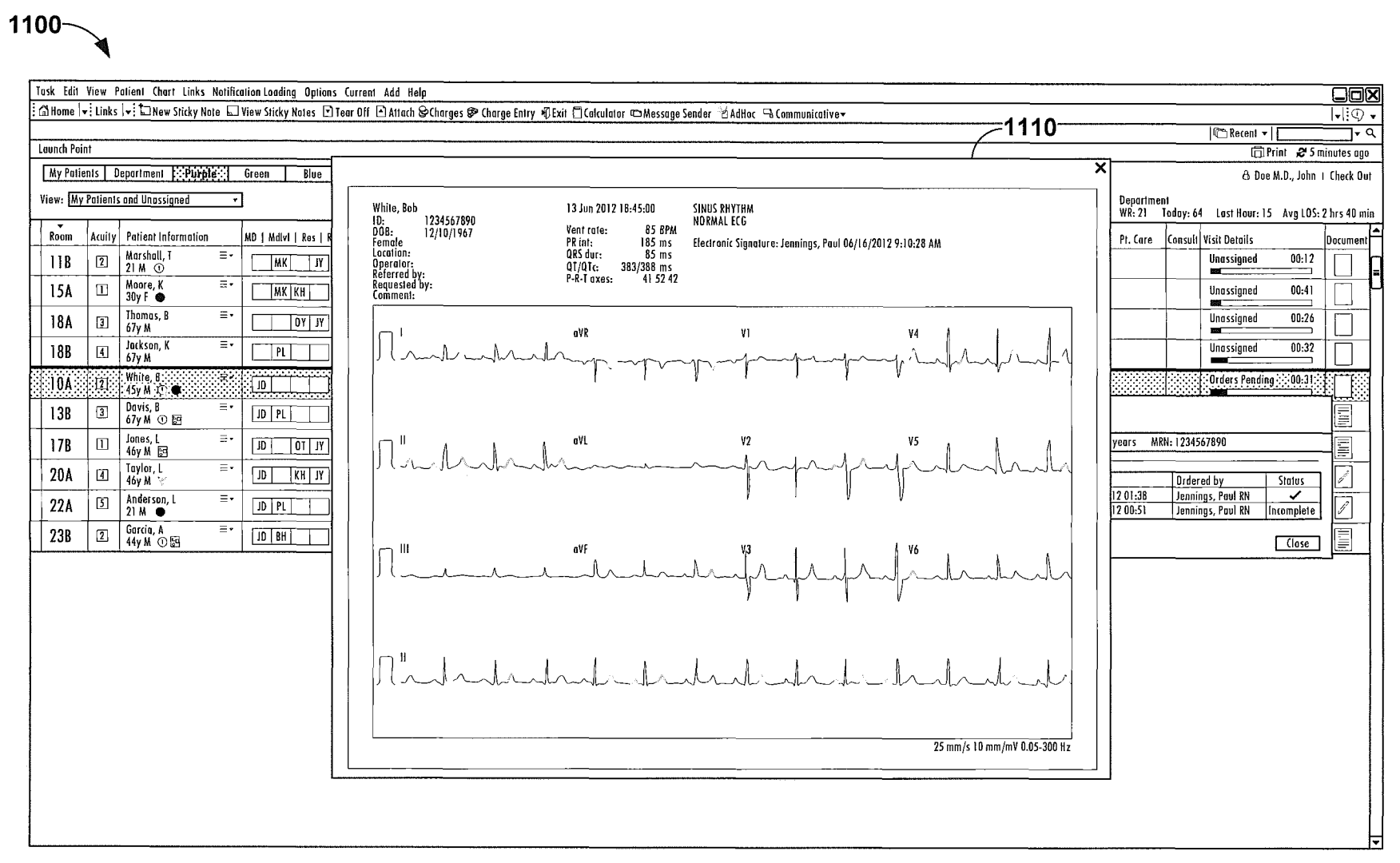

In FIG. 10, an illustrative screen display 1000 of an embodiment of the present invention is shown. In one example, by hovering or interacting with the EKG icon 1010, the EKG summary 1020 appears. The EKG summary may display each EKG order. As illustrated in the status column, the first EKG order 1022 is complete and the second EKG order 1024 is incomplete or pending. Turning now to FIG. 11, an illustrative screen display 1100 of an embodiment of the present invention is shown. In one instance, by selecting a link to the completed EKG order, the EKG results 1110 are provided.

Figure 12:
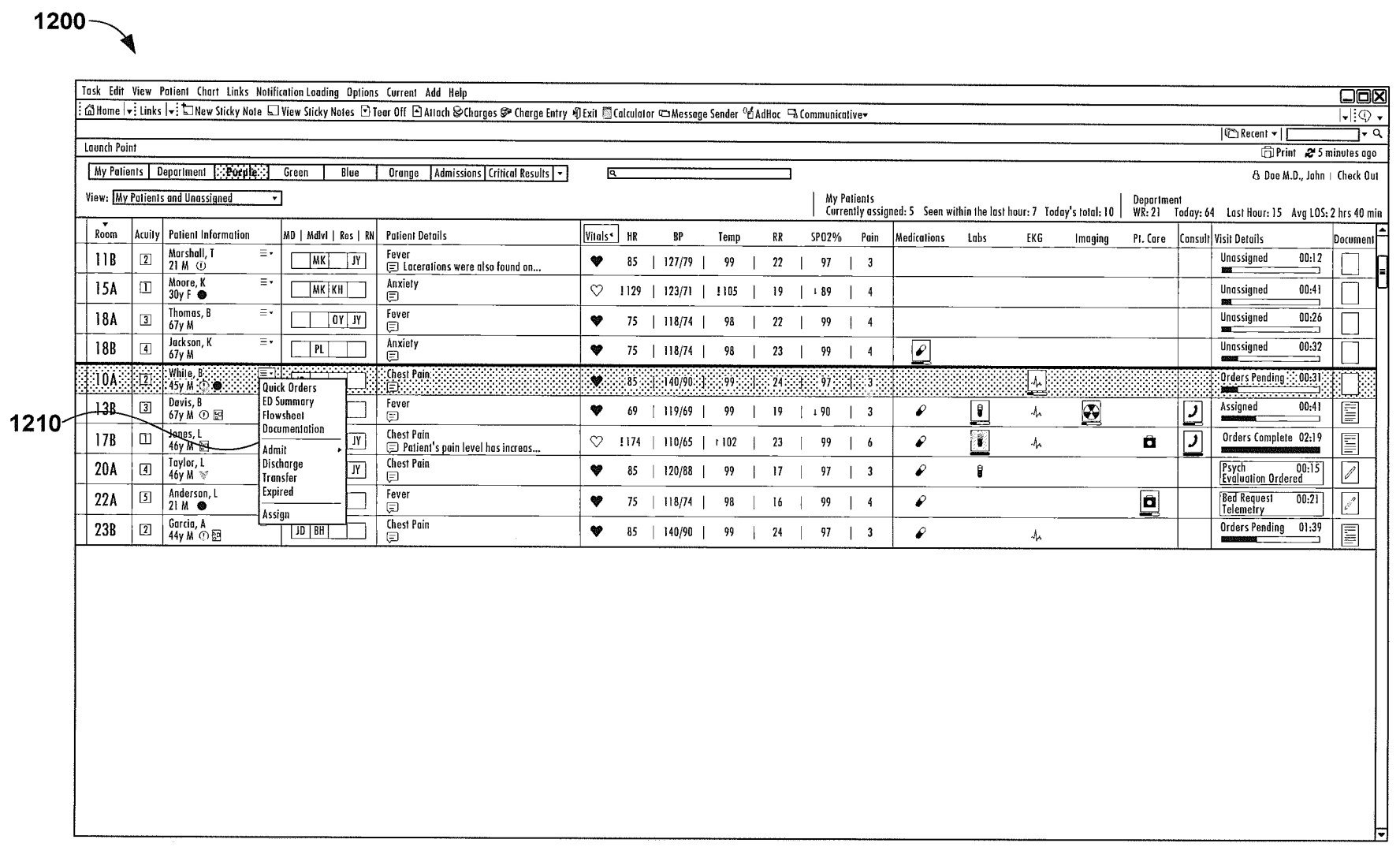

Referring now to FIG. 12, an illustrative screen display 1200 of an embodiment of the present invention is shown. By hovering over or interacting with the patient's name, such as by clicking on a dropdown menu 1210, options may be presented to the clinician. The options may include "Quick Orders," "ED Summary," "Flowsheet," "Documentation," "Admit," "Discharge," "Transfer," "Expired," or "Assign." Other options not shown in FIG. 12 may include prearrival and discharge process. Each of these options may be selected without opening another application.

Figure 13:
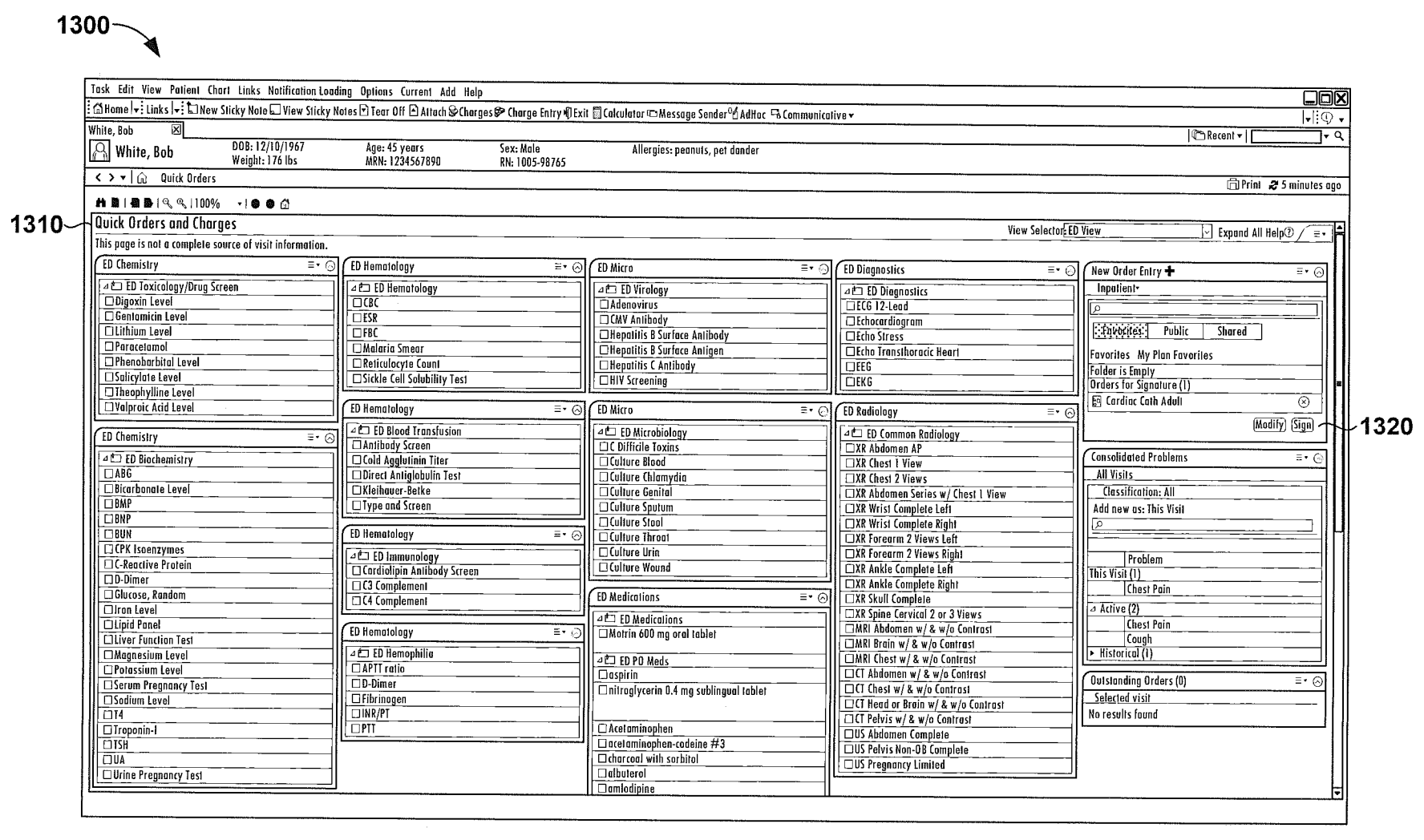

In FIG. 13, an illustrative screen display 1300 of an embodiment of the present invention is shown. In one example, by selecting or interacting with the "Quick Orders" option in FIG. 12, a quick orders display area 1310 is provided. The quick orders display area 1310 may allow the clinician to place single orders or order sets. After selecting all desired orders, the clinician may, for example, sign the orders directly in the quick orders display area 1310, without opening another application or the patient's EMR, such as by selecting or interacting with a sign button 1320.

Figure 14:
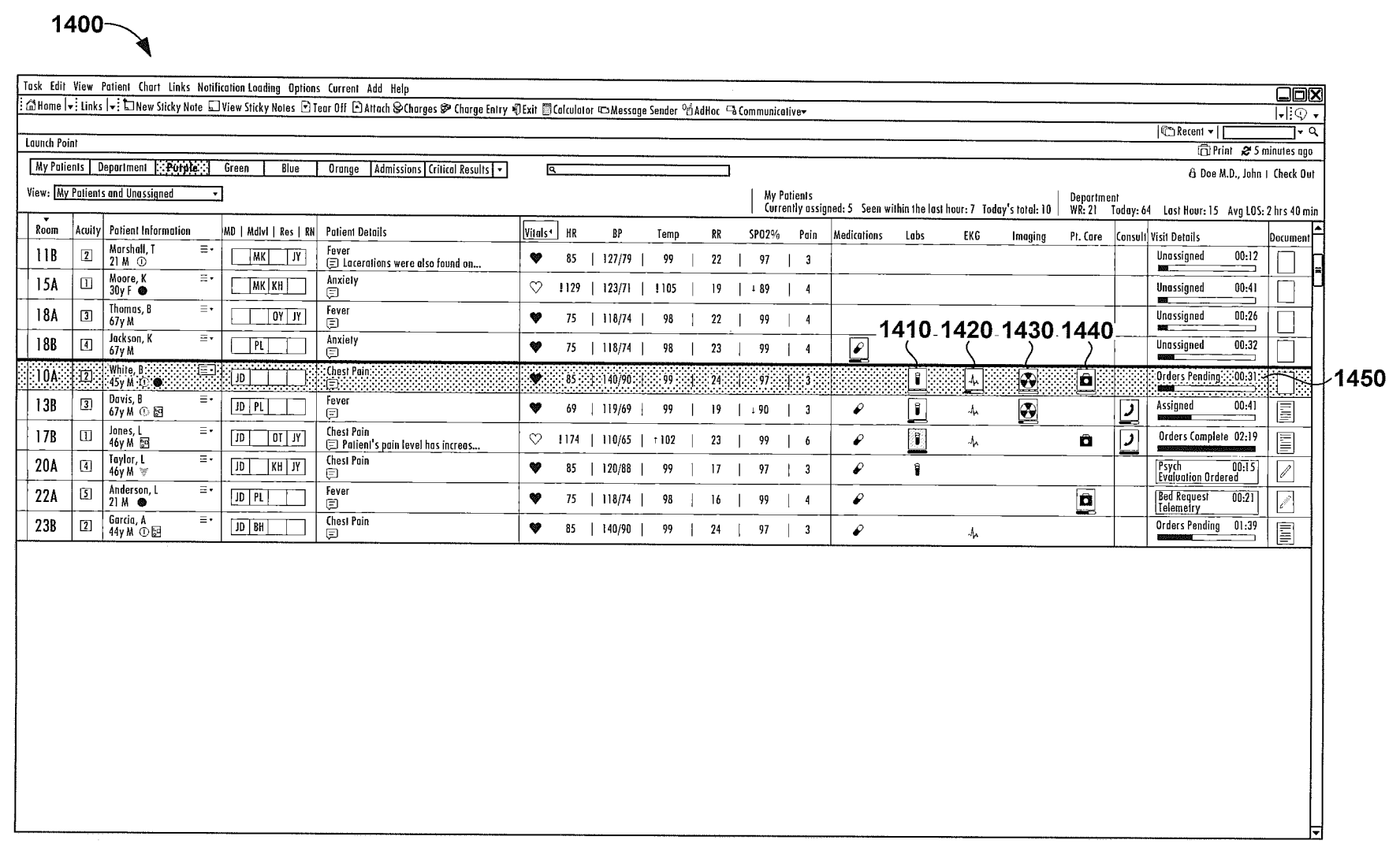

Turning now to FIG. 14, an illustrative screen display 1400 of an embodiment of the present invention is shown. After the desired orders are signed and processed, the ED centralized interactive display may be updated with the appropriate icons. For example, for patient "White, B.," orders have been placed for labs 1410, EKG 1420, imaging 1430, and patient care 1440. The length of stay area 1450 may also be updated with the status "Orders Pending." As already discussed, the length of stay area 1450 may also include a status bar that indicates the progress of a particular status for each patient (i.e., in this case, the progress of the pending orders).

Figure 15:
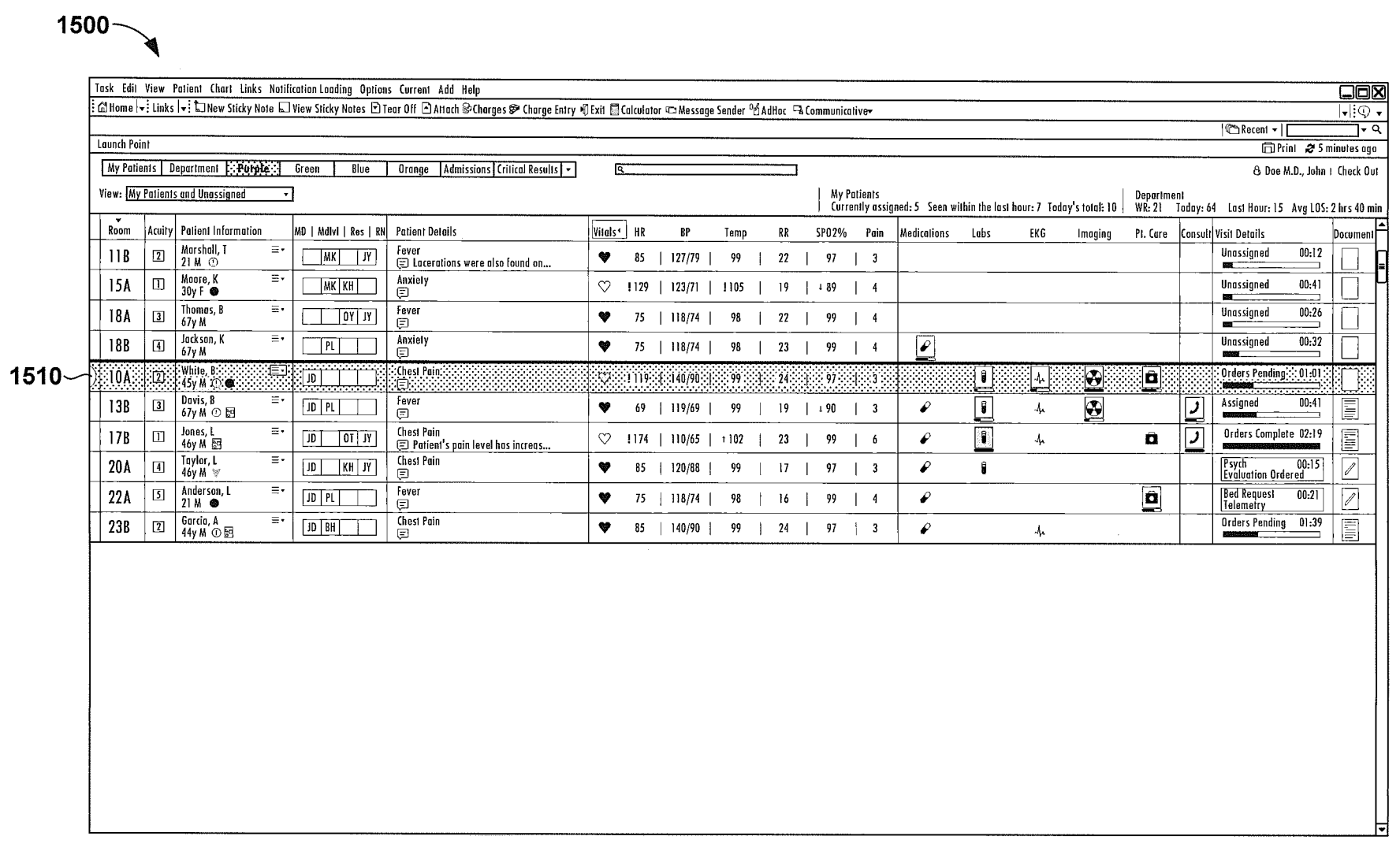

Referring now to FIG. 15, an illustrative screen display 1500 of an embodiment of the present invention is shown. As illustrated, in the throughput display area, a glow or light bulb 1510 may indicate that some type of action is needed by the clinician. The actions might be information that another clinician has flagged within documentation for the clinician's attention, or may be orders that need to be co-signed. By hovering over or clicking on the glow 1510, the clinician may be provided with details associated with the action. The clinician may also take appropriate action from within the same window that provides the details.

Figure 16:
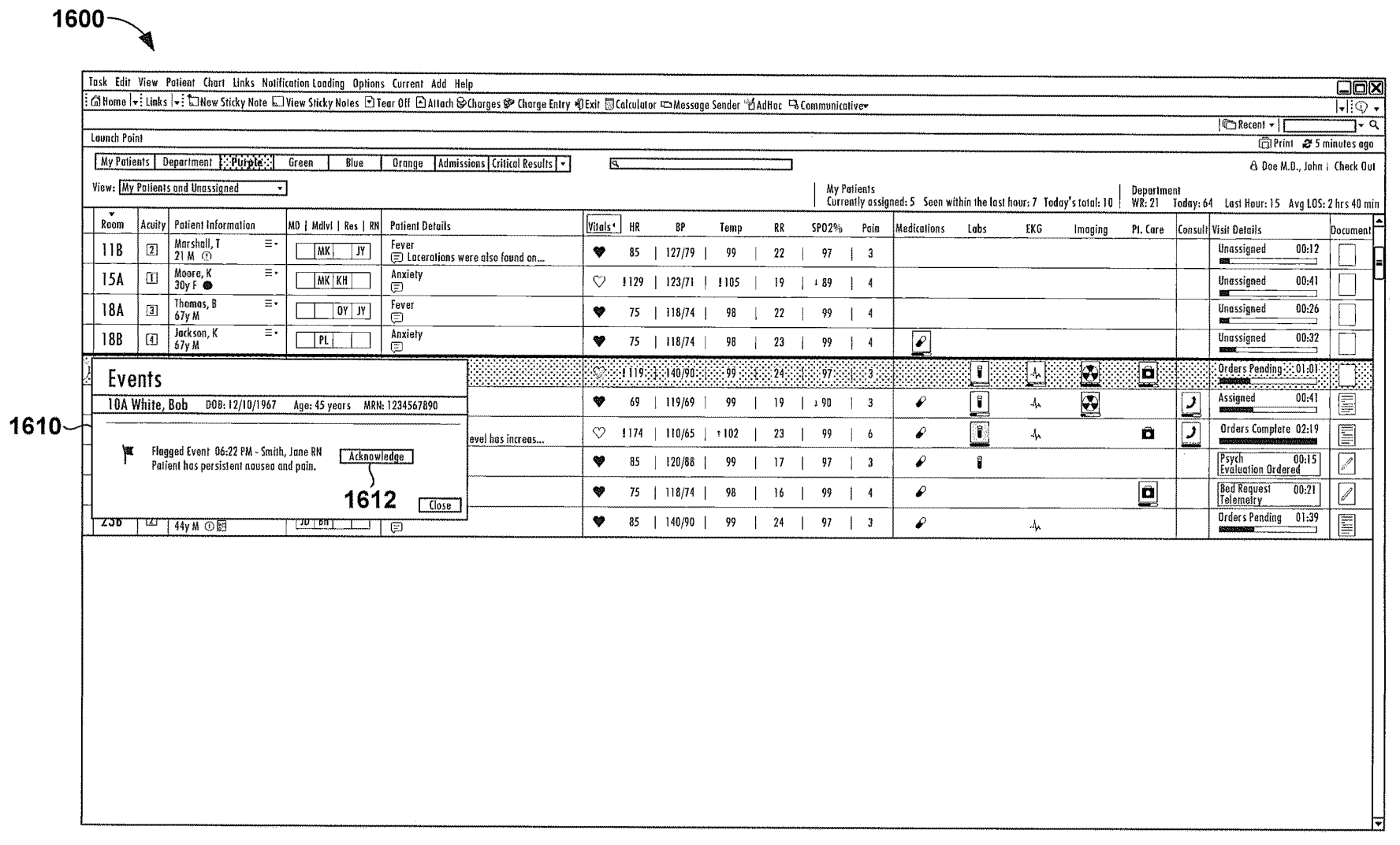

In FIG. 16, an illustrative screen display 1600 of an embodiment of the present invention is shown. In one example, after hovering over or interacting with the glow, details 1610 are provided to the clinician. In this example, a nurse has documented that the patient is experiencing persistent nausea and pain and has flagged this for review by the clinician. Once the clinician has reviewed, the clinician can acknowledge this documentation by, for example, selecting an acknowledge button 1612 from within the same window and without opening another application or the patient's EMR. The details provided may also indicate information associated with the status of the patient, as may also be provided by length of stay display area.

Figure 17:
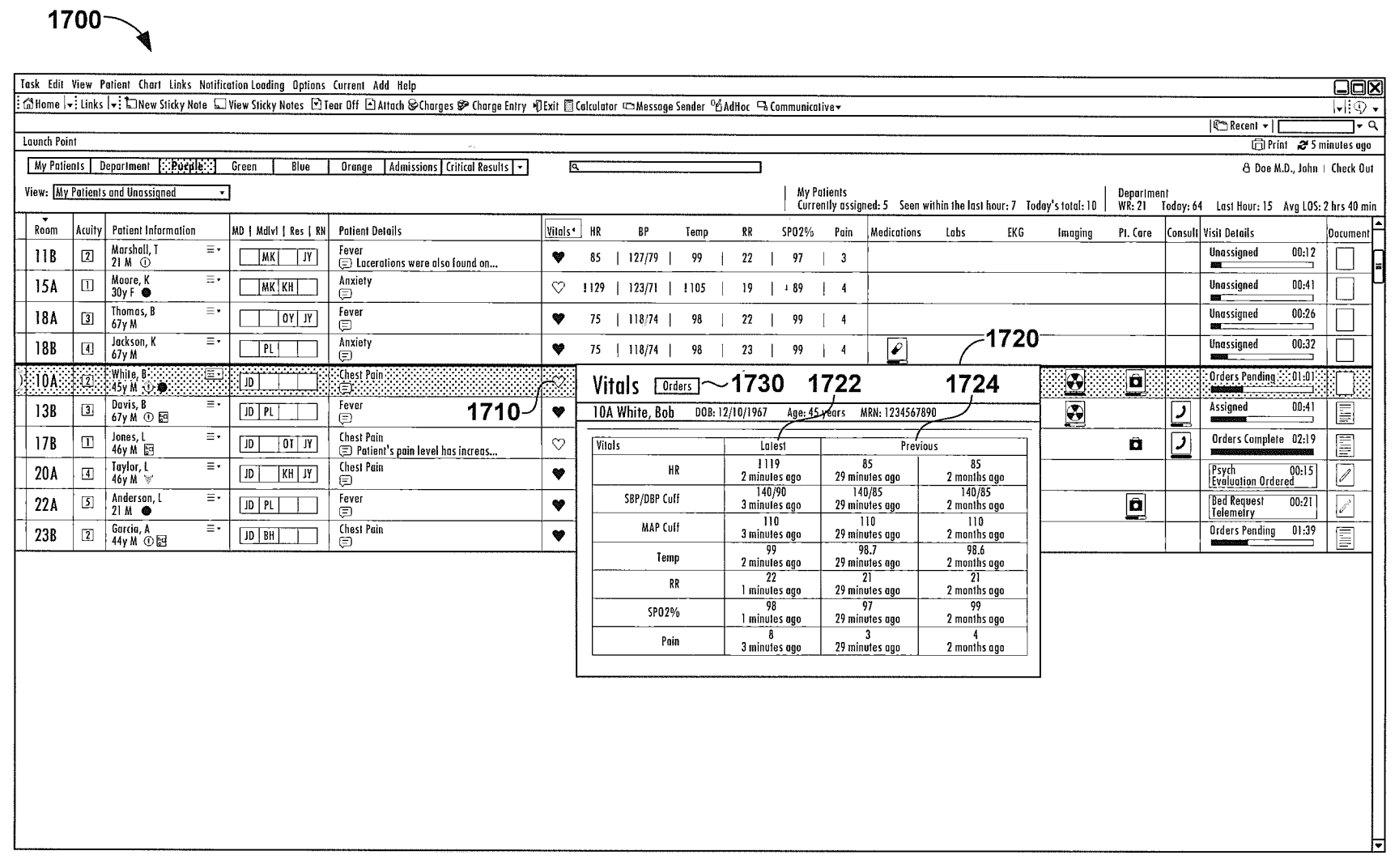

Turning now to FIG. 17, an illustrative screen display 1700 of an embodiment of the present invention is shown. In one example, by hovering over or interacting with the vital signs icon 1710, the vital signs summary 1720 is provided. The vitals summary may provide the latest vital signs results 1722 and the two previous vital signs results 1724. Color indicators may allow critical results to appear more prominently. The clinician may also select an orders button 1730 to launch the quick orders display area.

Figure 18:
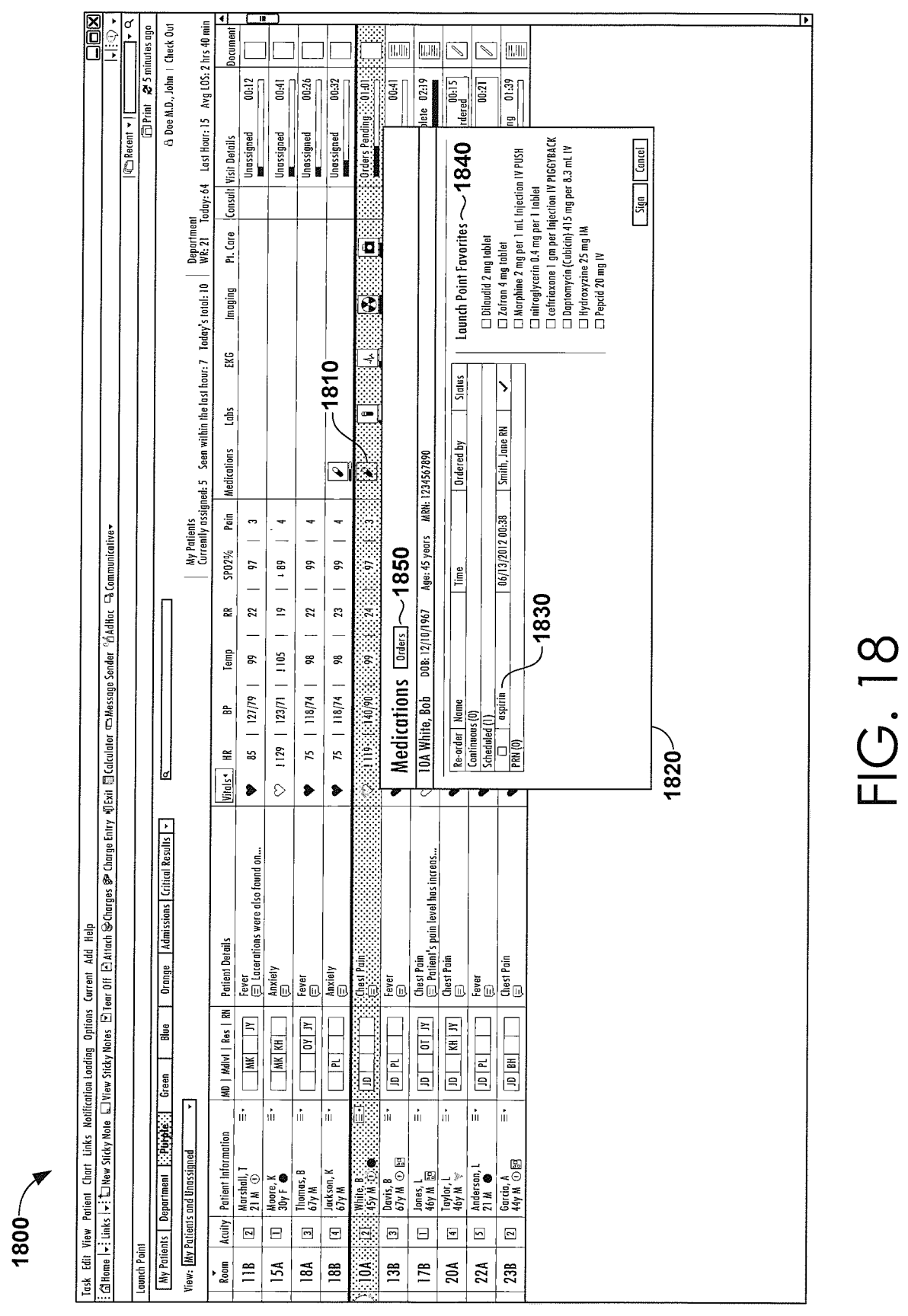

Referring now to FIG. 18, an illustrative screen display 1800 of an embodiment of the present invention is shown. In one example, by hovering over or interacting with the medications icon 1810, the medications summary 1820 is provided. The medications summary may provide information regarding continuous medications, scheduled medications, and PRN medications. In this illustration, aspirin 1830 is a scheduled medication. The status of the medication may also be provided. Further, a checkbox may be provided next to the medication allowing the clinician to quickly re-order the medication. A quick order form 1840 may also be provided to allow the clinician to quickly order medications that may be frequently ordered by that clinician, within that ED, or for a particular condition or diagnosis associated with the patient. The clinician may also select an orders button 1850 to launch the quick orders display area.

Figure 19:
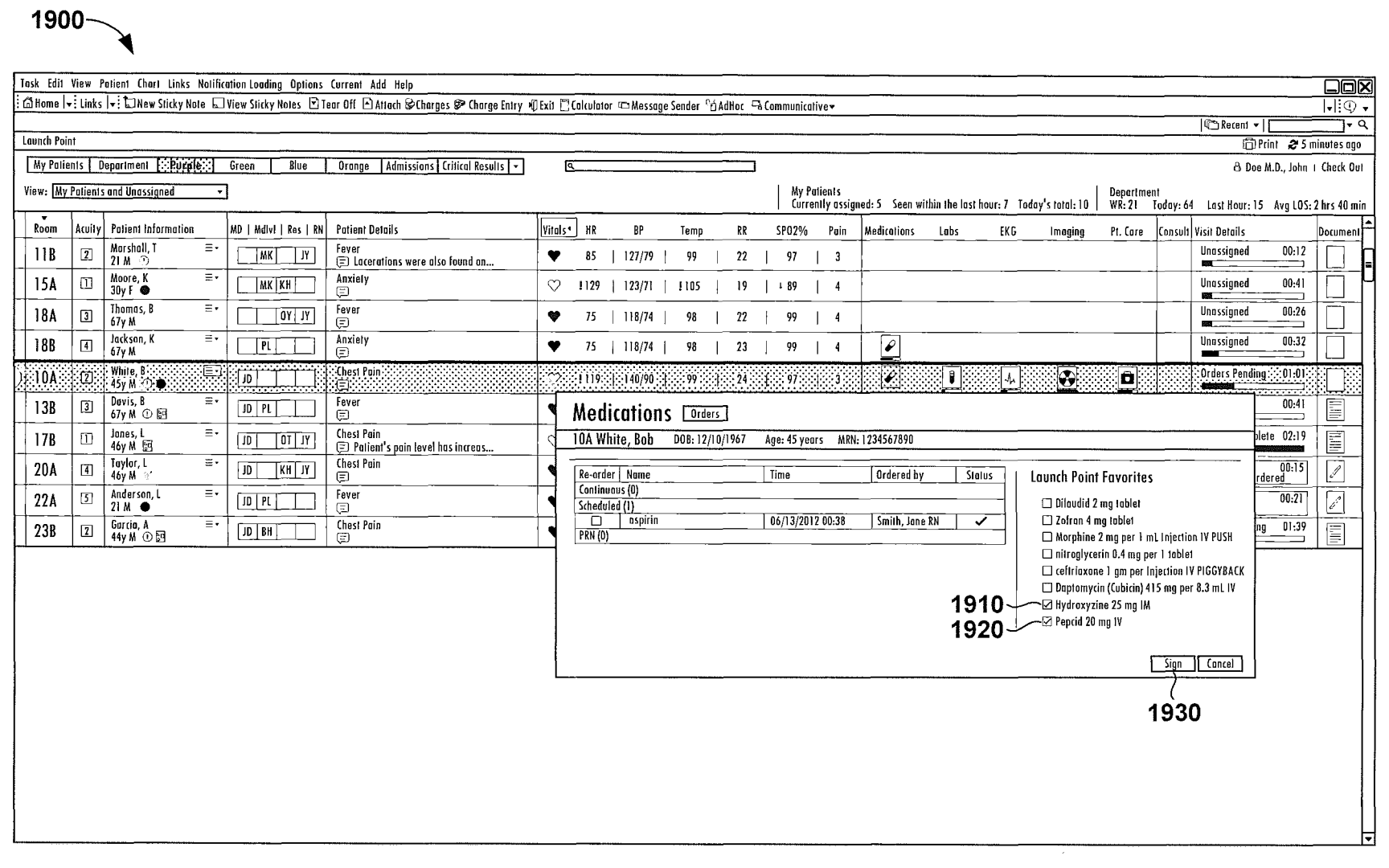

In FIG. 19, an illustrative screen display 1900 of an embodiment of the present invention is shown. In this example, the clinician has placed orders for two frequently ordered medications, Hydroxyzine 1910 and Pepcid 1920. The quick order form may allow the clinician to sign the order directly within the quick order form, without opening another application or the patient's EMR, by selecting the sign button 1930.

Figure 20:
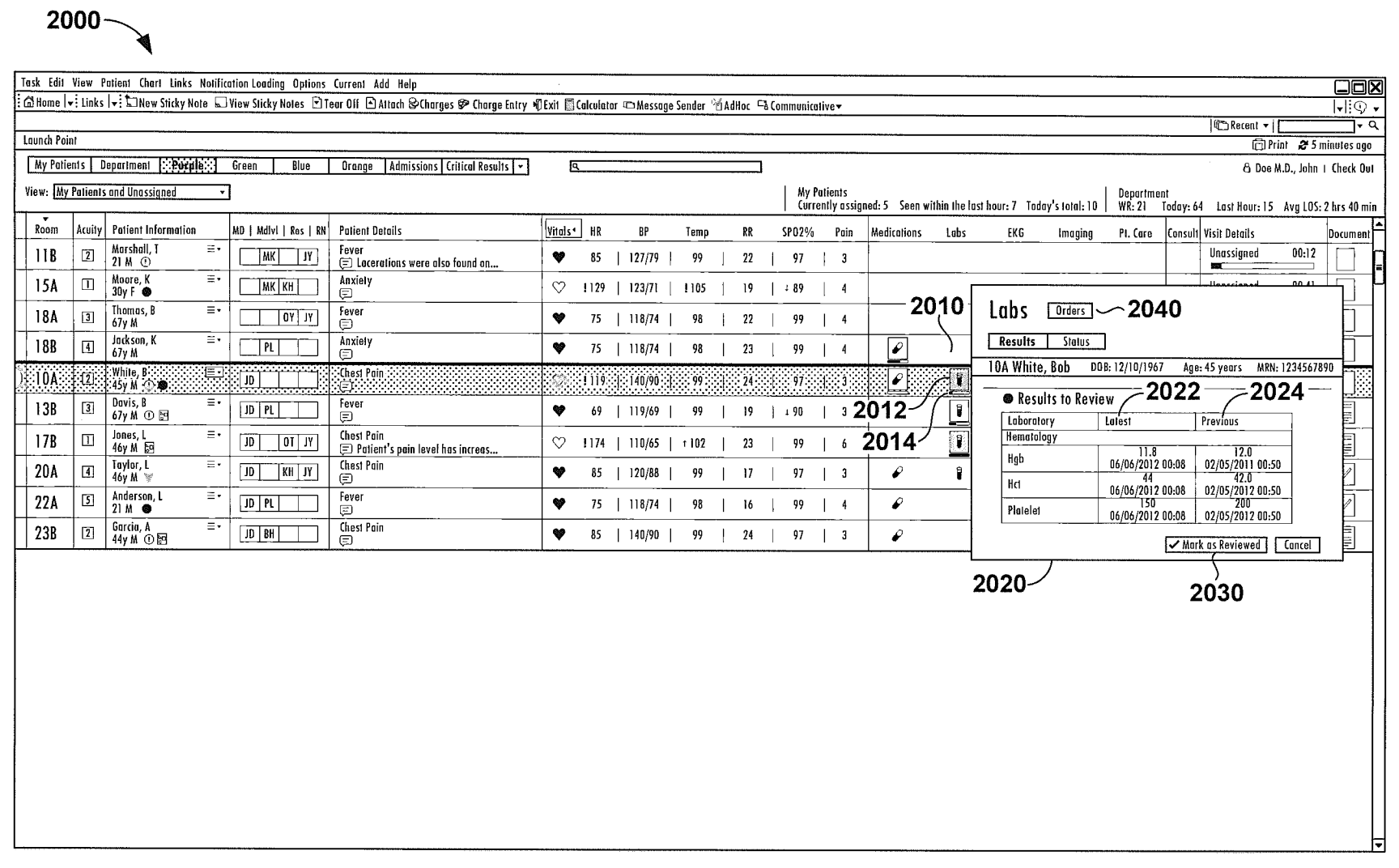

Turning now to FIG. 20, an illustrative screen display 2000 of an embodiment of the present invention is shown. In one example, by hovering over or interacting with the labs icon 2010, the labs summary 2020 is provided. The labs summary 2020 may provide the latest lab results 2022 as well as previous lab results 2024. The appearance 2012 of the labs icon 2010 may be darker or lighter to let the clinician know that results are available that have not been reviewed by the clinician. A status bar 2014 may indicate the status of the lab orders (e.g., complete, not completed, etc.). Color indicators may further indicate the status (e.g., overdue). After reviewing the results, the clinician may select a mark as reviewed 2030 to update the status of a particular lab as reviewed.

Figure 21:
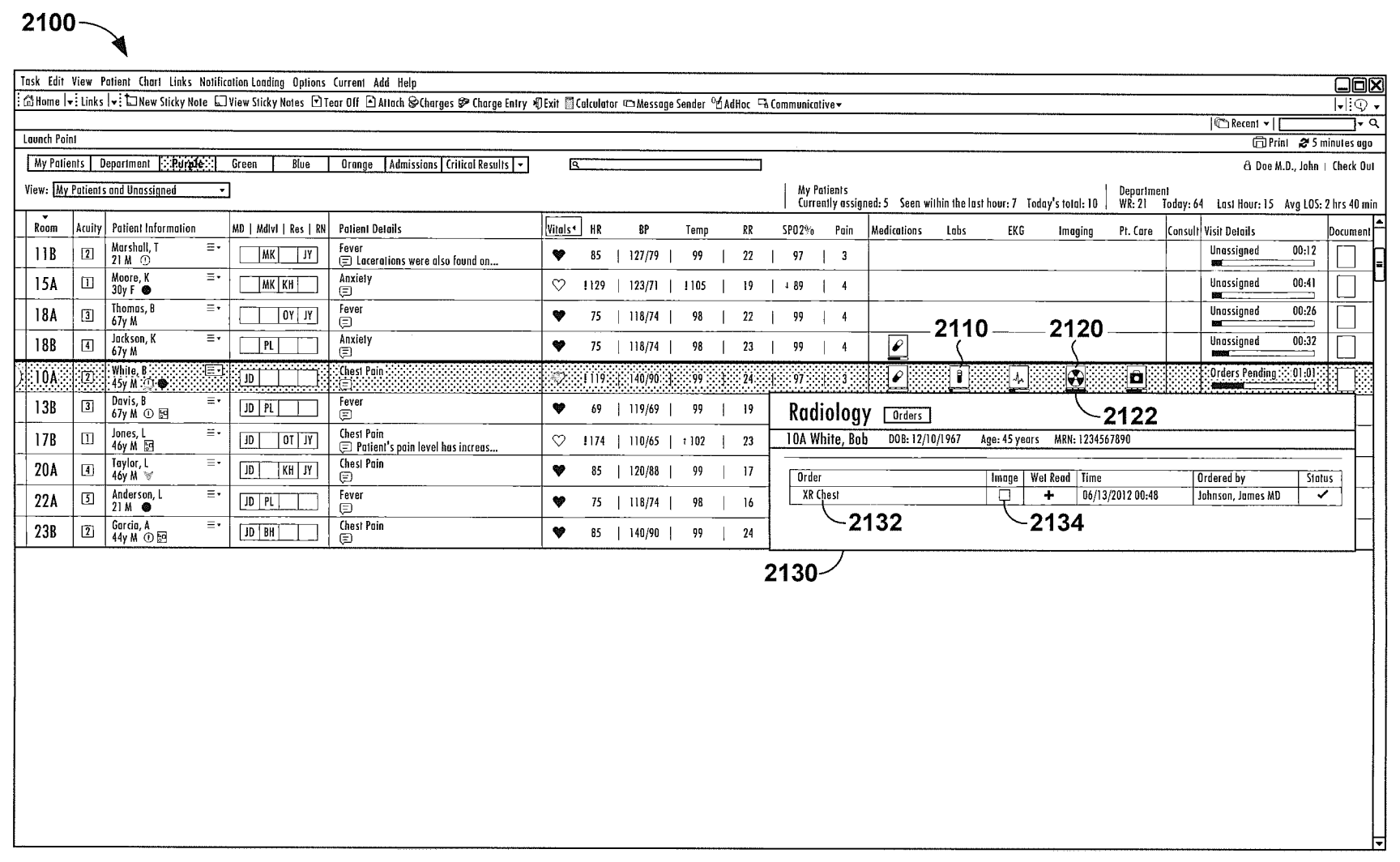

Referring now to FIG. 21, an illustrative screen display 2100 of an embodiment of the present invention is shown. As illustrated, the color of the lab icon 2110 has changed from grey to white, indicating that all available results have been reviewed. In one example, by hovering over or interacting with the images icon 2120, the images summary 2130 is provided. As illustrated, a status bar 2122 below the images icon 2120 may indicate whether an order is complete. The status bar 2122 may be color coded in addition to showing progress associated with the status of the order. The images summary 2130 may provide details of an images order 2132. An image box 2134 can be selected to launch or display the image.

Figure 22:
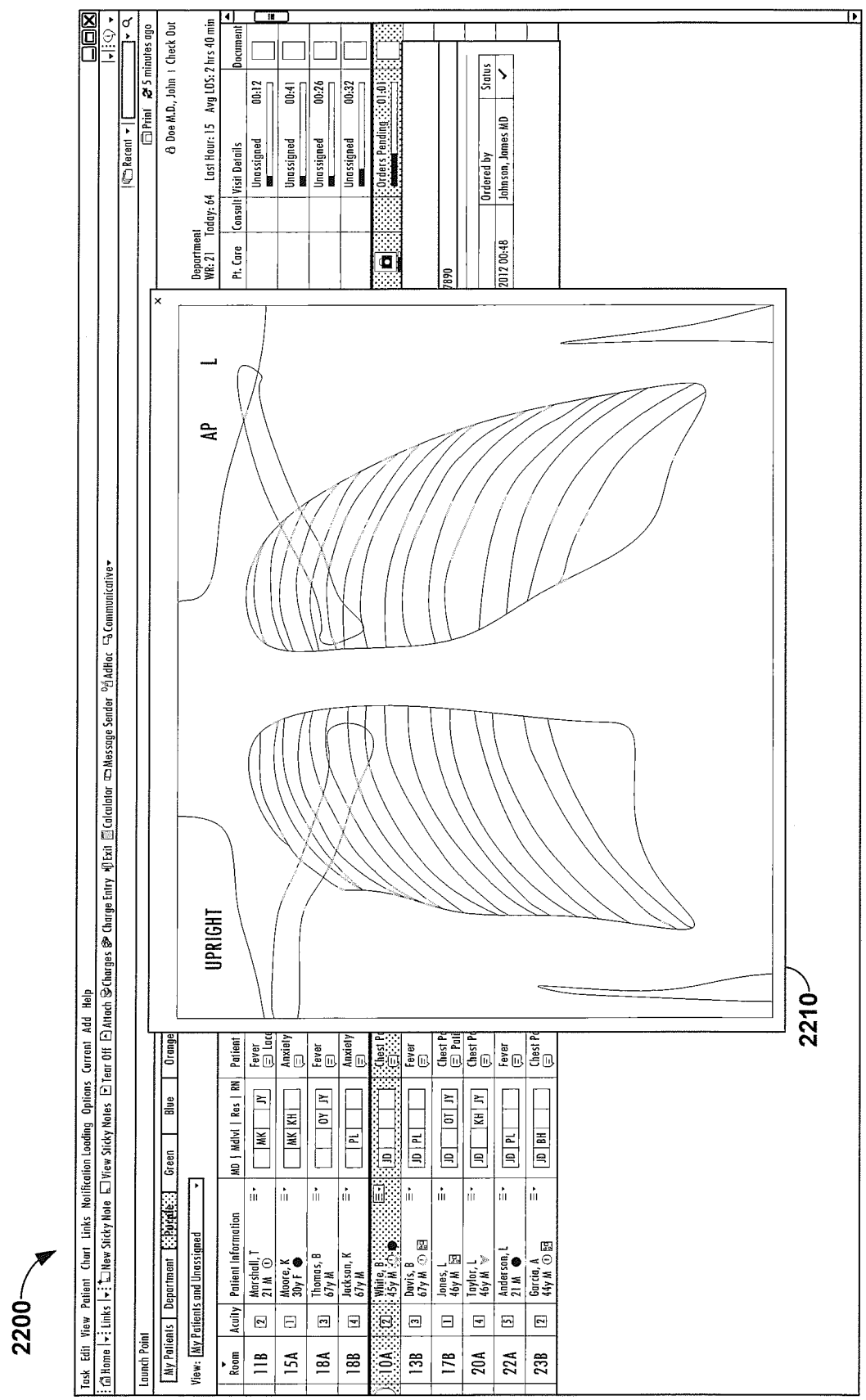

In FIG. 22, an illustrative screen display 2200 of an embodiment of the present invention is shown. As illustrated, the image box in FIG. 21 may be selected and the image 2210 may be launched or displayed. The image may be launched by a separate application or viewing system or may be displayed directly within the ED centralized interactive display (i.e., without opening a separate application).

Figure 23:
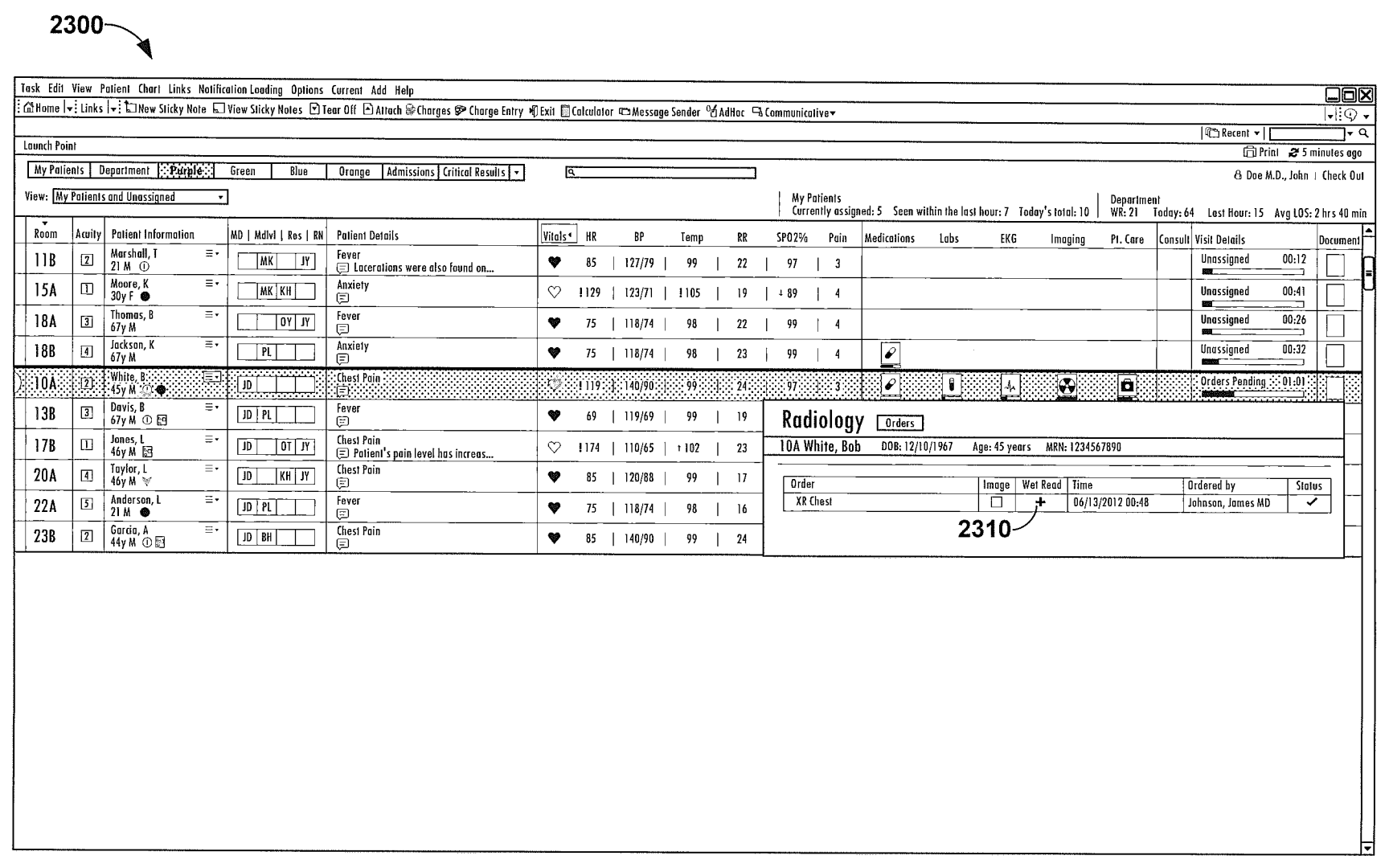
Figure 24:
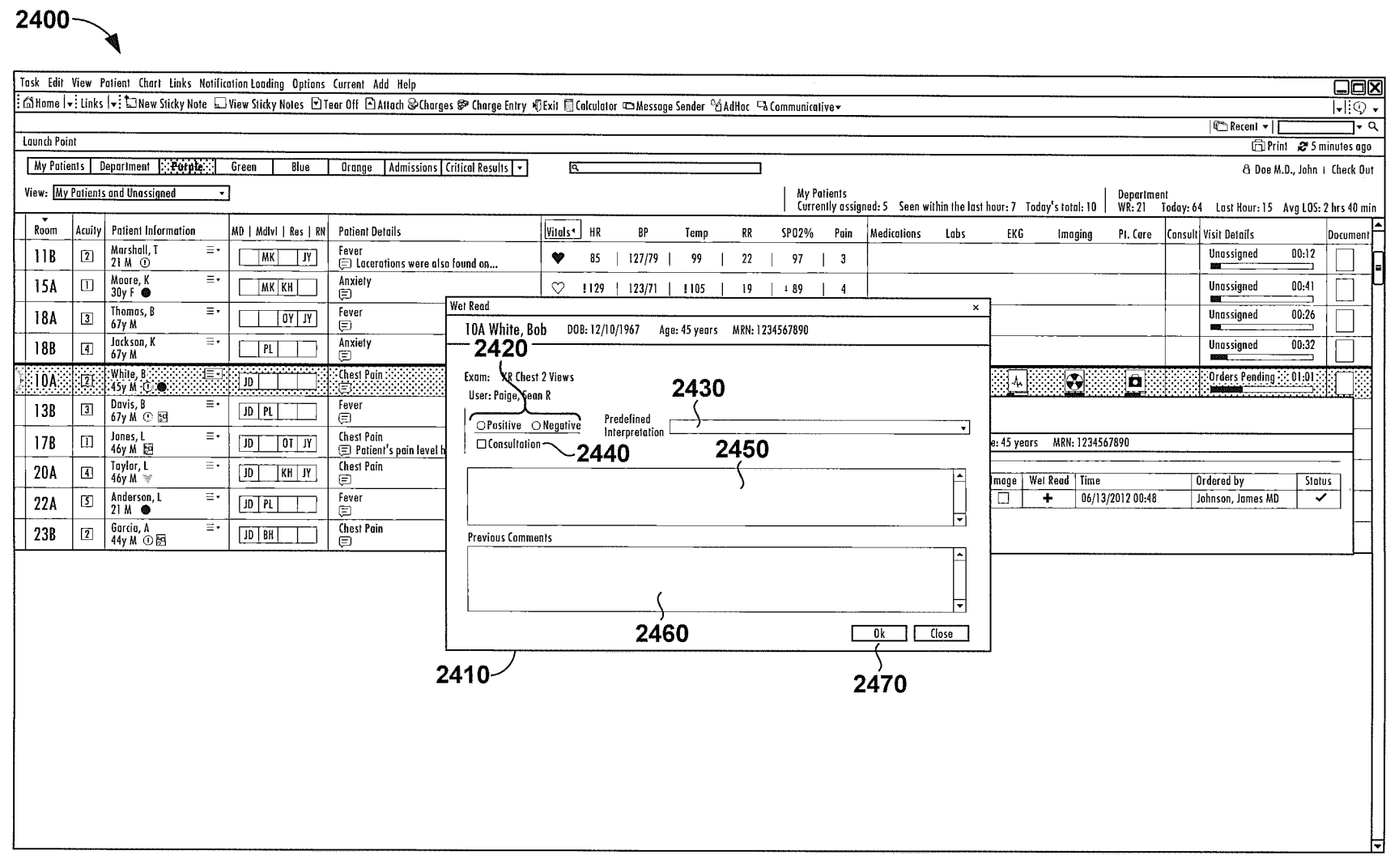

Turning now to FIG. 23, an illustrative screen display 2300 of an embodiment of the present invention is shown. Within the images summary, the clinician may also document a wet read of the image by selecting the wet read icon 2310. Referring now to FIG. 24, an illustrative screen display 2400 of an embodiment of the present invention is shown. After selecting the wet read icon as described with respect to FIG. 23, a wet read window 2410 may be opened. The wet read window 2410 may allow the clinician to indicate a positive or negative result 2420, select a predefined interpretation 2430, select whether a consultation 2440 is needed, provide comments 2450, review previous comments 2460, and save the wet read by selecting an "ok" button 2470.

Figure 25:
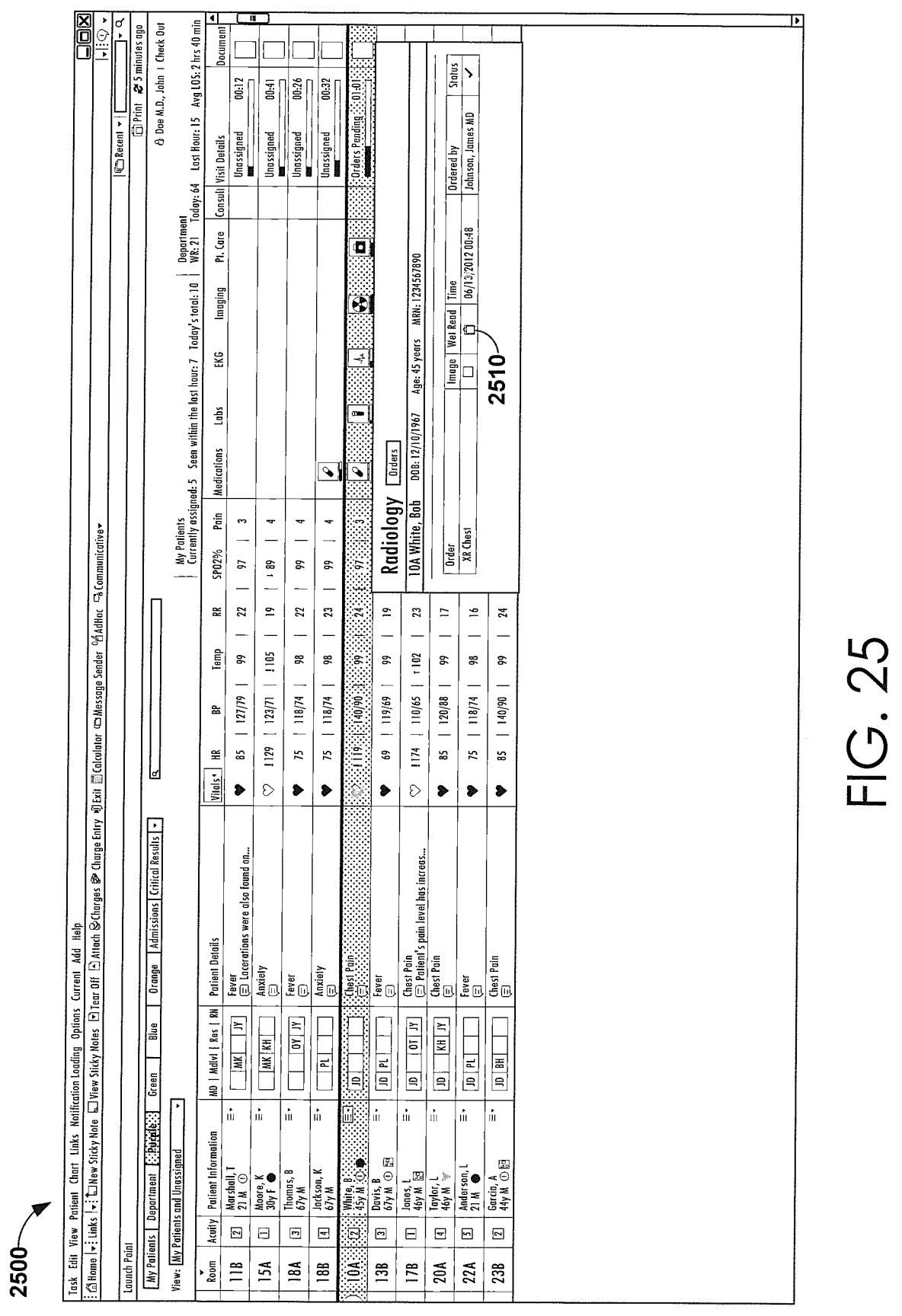

In FIG. 25, an illustrative screen display 2500 of an embodiment of the present invention is shown. Once the wet read has been provided as described with respect to FIG. 24, the wet read icon 2510 may change to let the clinician know that wet read has been documented for that particular image.

Figure 26:
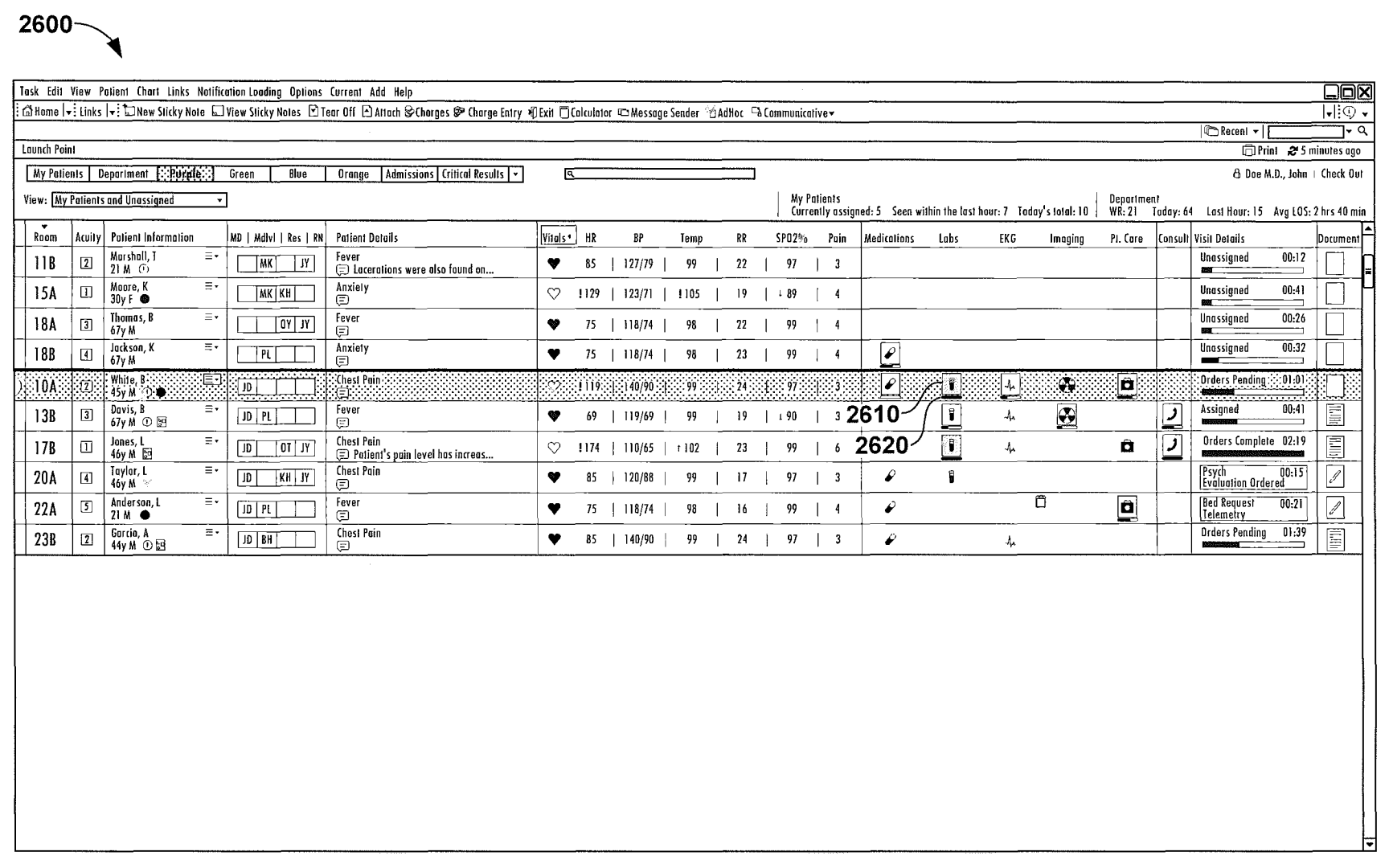

Turning now to FIG. 26, an illustrative screen display 2600 of an embodiment of the present invention is shown. As illustrated by the lab icon 2610, the status bar 2620 may indicate that all lab orders are completed. The color of the lab icon may indicate whether a critical value has been received (e.g., red lab icon).

Figure 27:
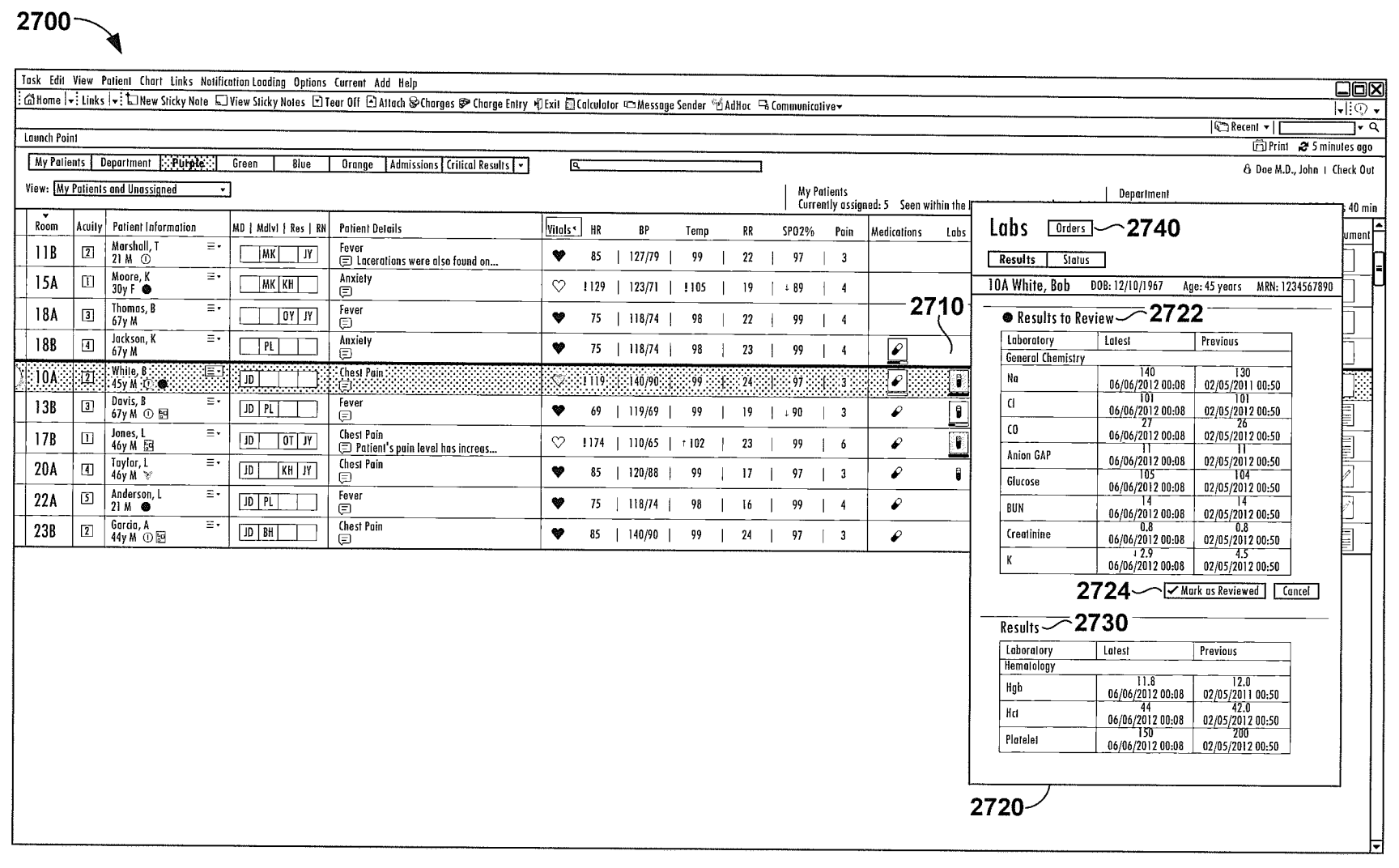

Referring now to FIG. 27, an illustrative screen display 2700 of an embodiment of the present invention is shown. In one example, by hovering over the lab icon 2710, the lab summary 2720 is provided. Results that need to be reviewed 2722 may appear more prominently than results that do not necessarily require review 2730. Once reviewed, the clinician can select a mark as reviewed button 2724. Any additional orders that may be desired may be placed by selecting the orders button 2740, which may open the quick orders display area described herein.

Figure 28:
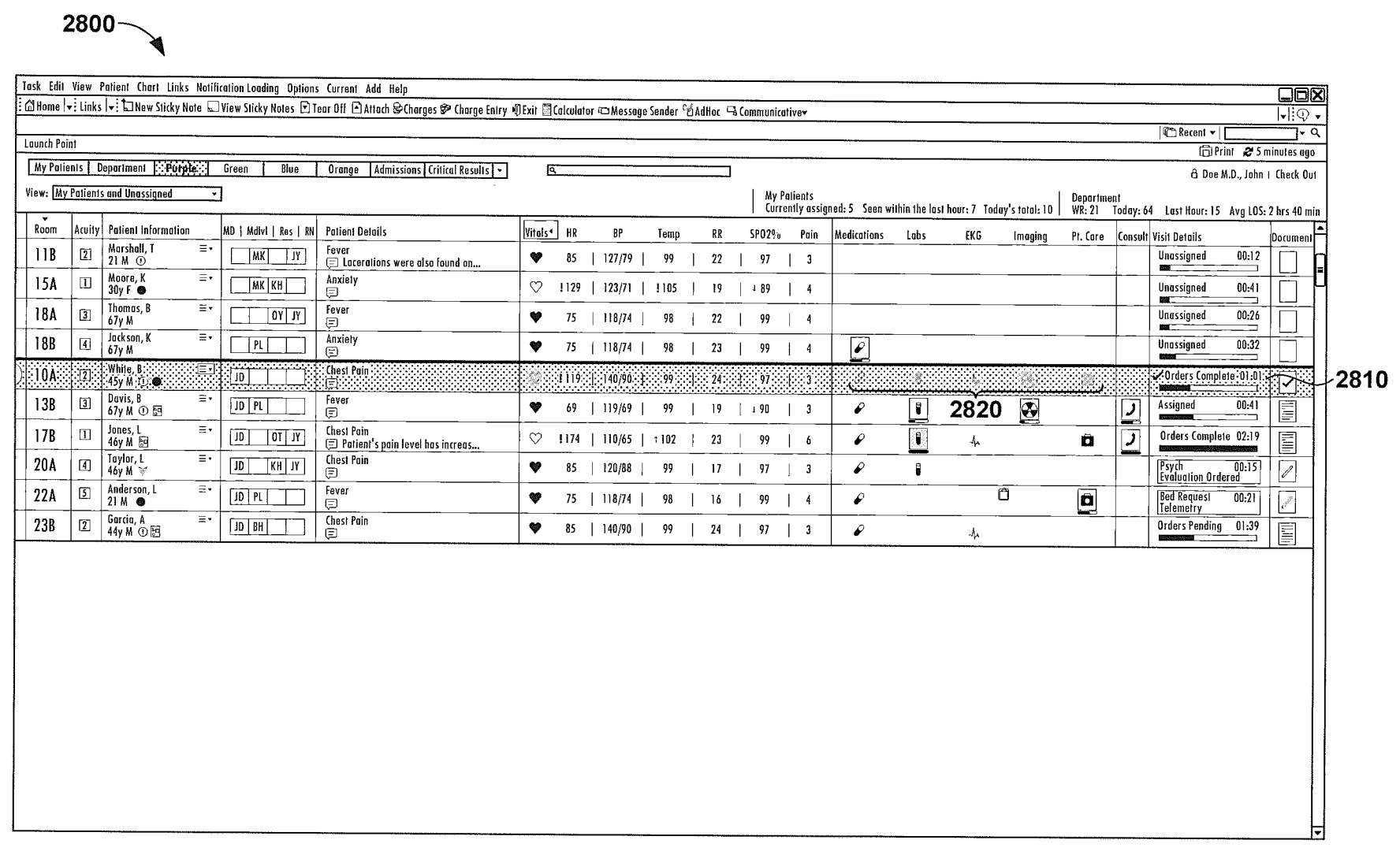

In FIG. 28, an illustrative screen display 2800 of an embodiment of the present invention is shown. After all orders are complete, the clinician may be alerted by the length of stay display area 2810. The throughput display area may provide a similar indication. Each of the orders icons (e.g., medications, labs, EKG, imaging, and patient care) may also be dithered out indicating that orders associated with each of the orders icons are complete.

Figure 29:
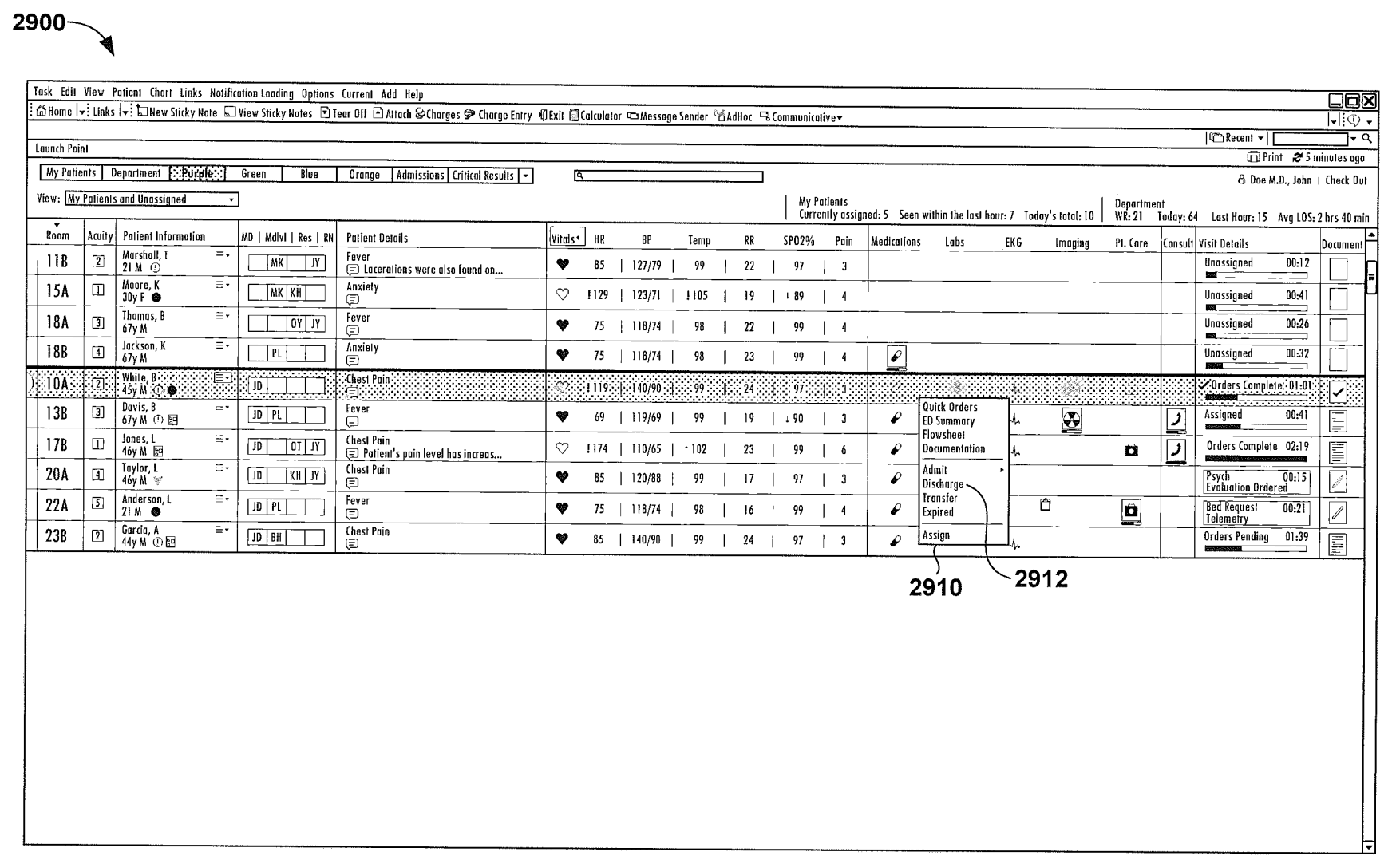

Turning now to FIG. 29, an illustrative screen display 2900 of an embodiment of the present invention is shown. After the orders are complete, for example, the clinician may determine the patient is ready to be discharged. The clinician may right click on the row associated with that patient and options 2910 may be presented to the clinician. The clinician may select discharge 2912 (or another appropriate option).

Figure 30:
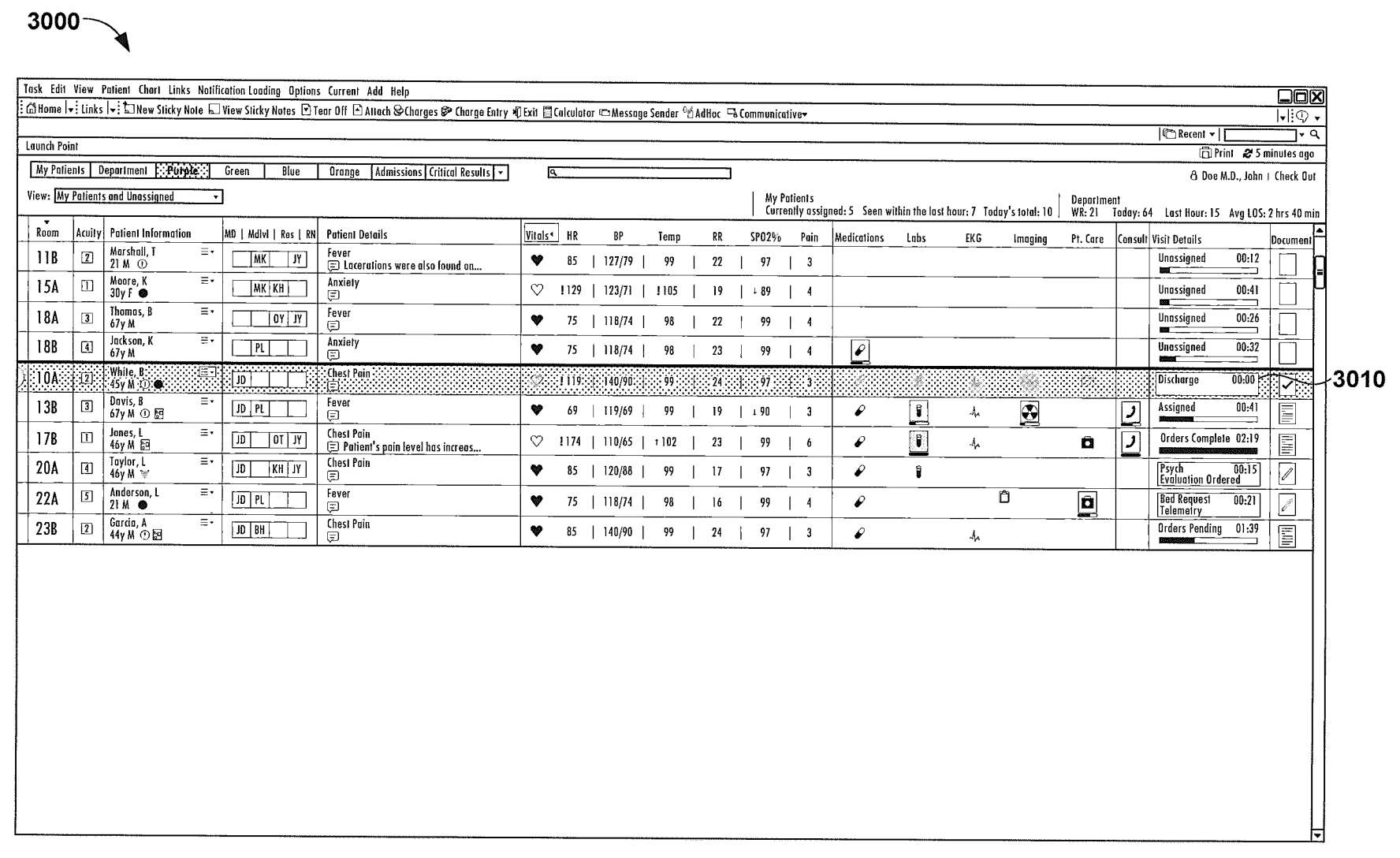

Referring now to FIG. 30, an illustrative screen display 3000 of an embodiment of the present invention is shown. As illustrated, the patient's status in the length of stay display area 3010 may be updated to discharge. This status may also be updated in the throughput display area. Once the order to discharge the patient has been placed, the timer in the length of stay display area may be reset so the clinician and/or facility can track how long the patient waits to physically be discharged after the discharge order has been placed.

Figure 32:
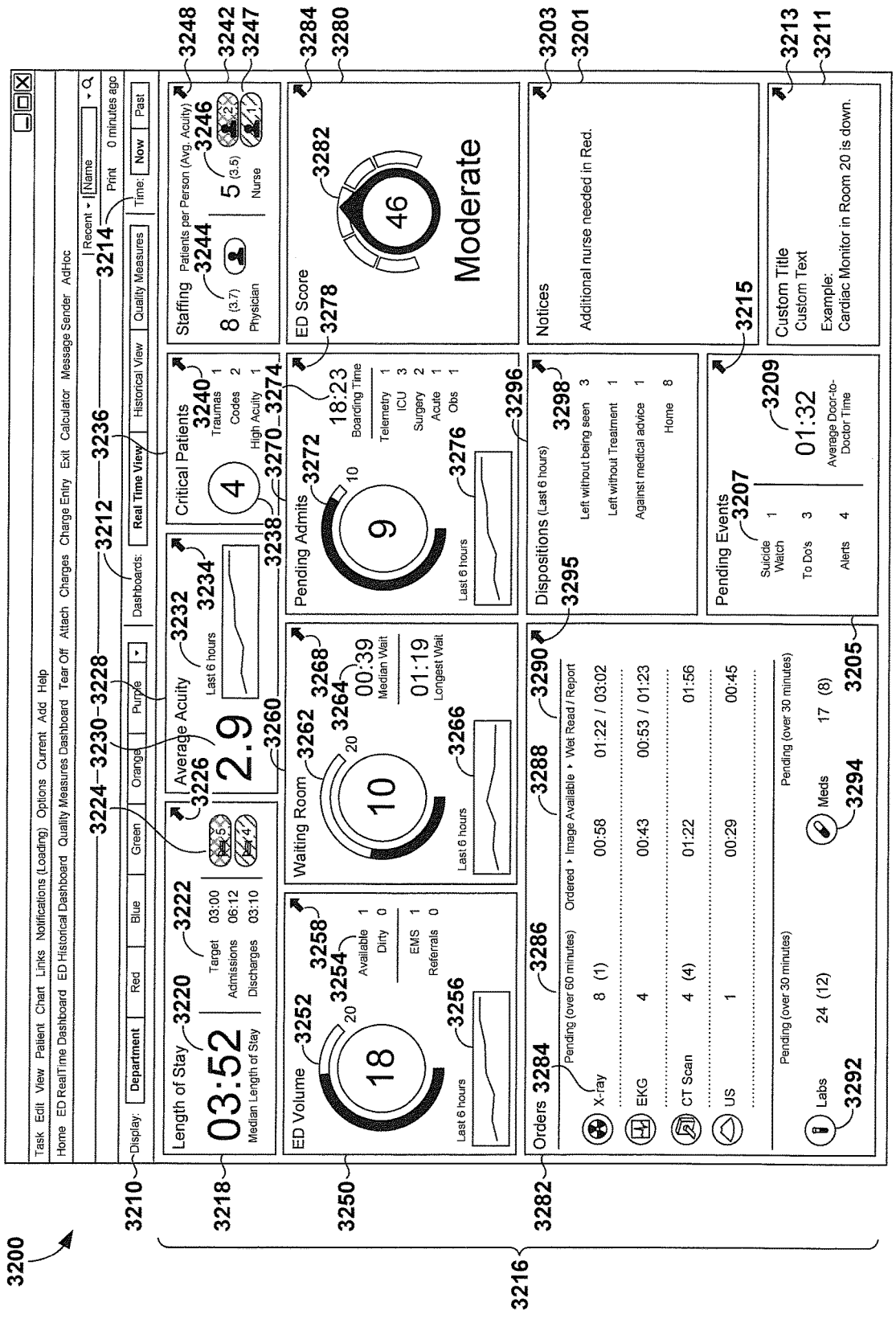
Figure 34:
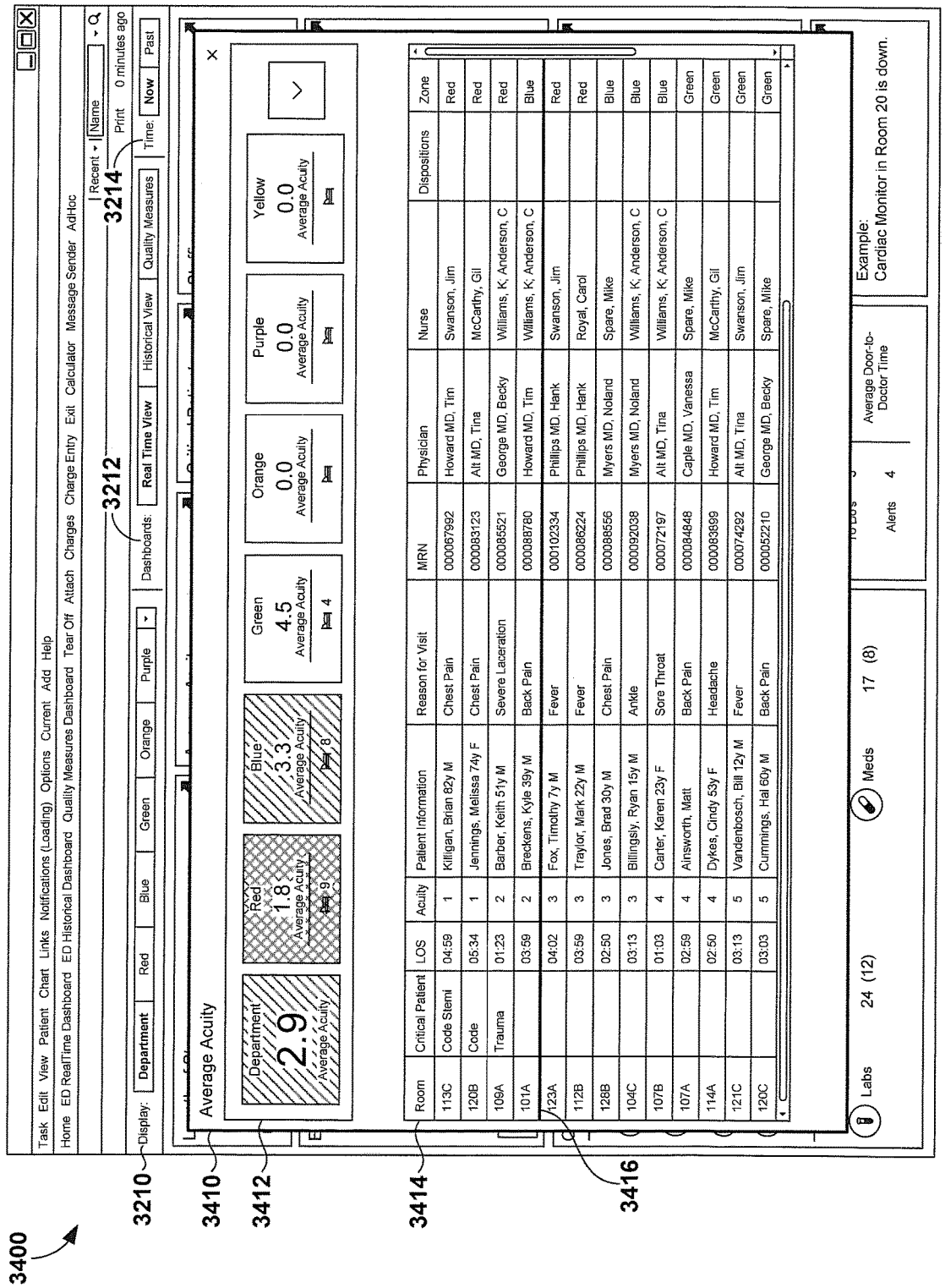
Figure 35:
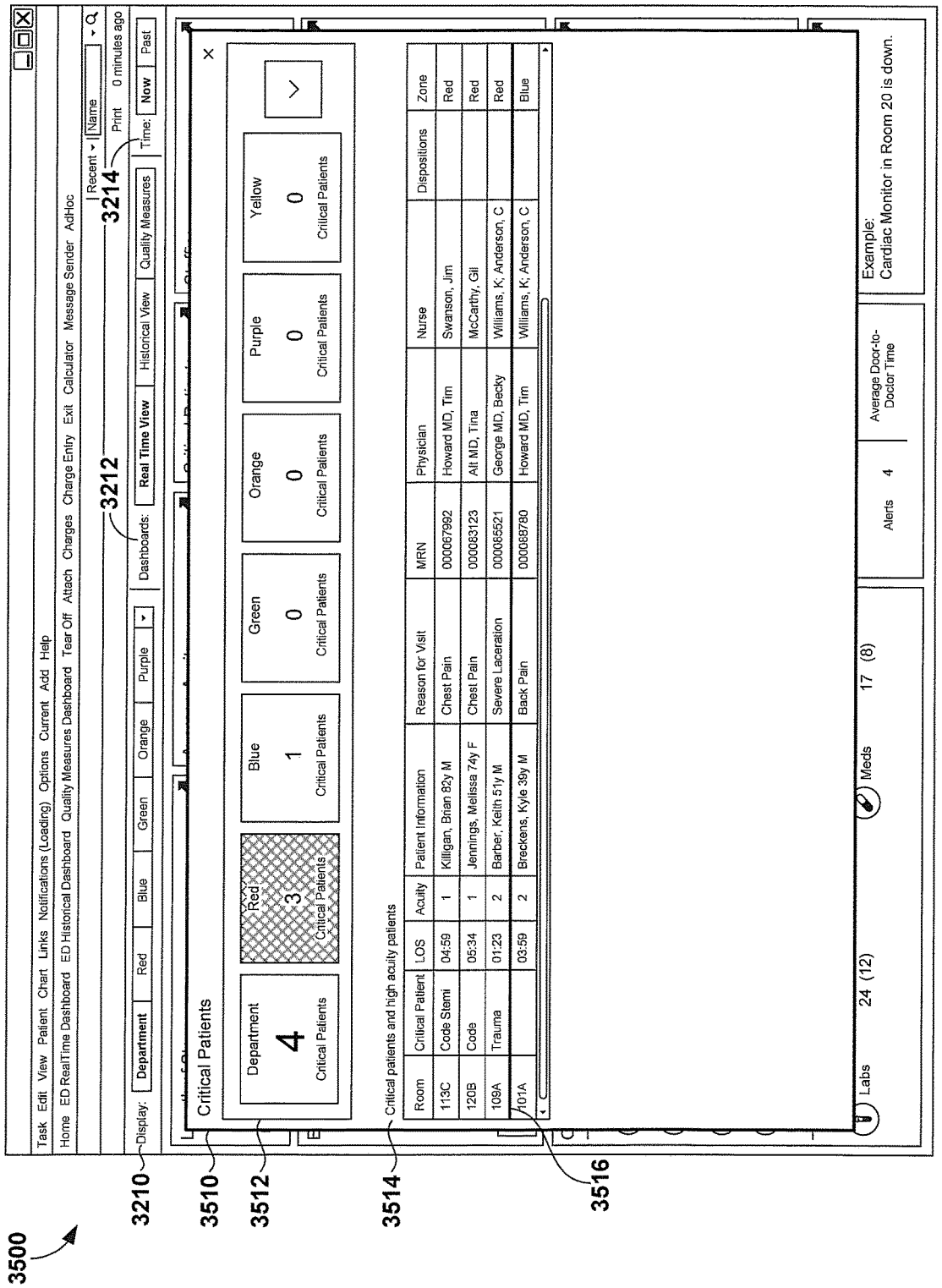
Figure 36:
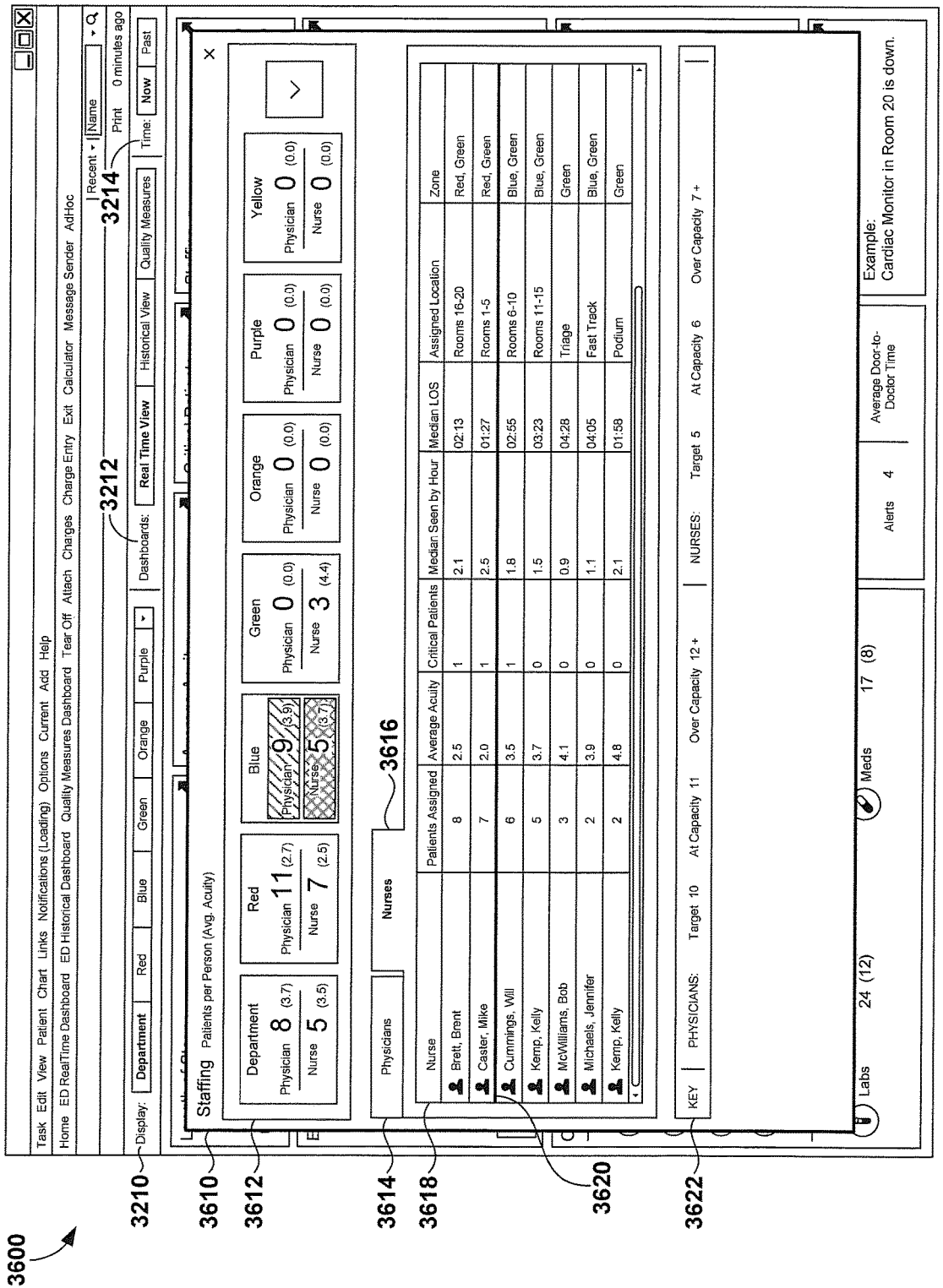
Figure 37:
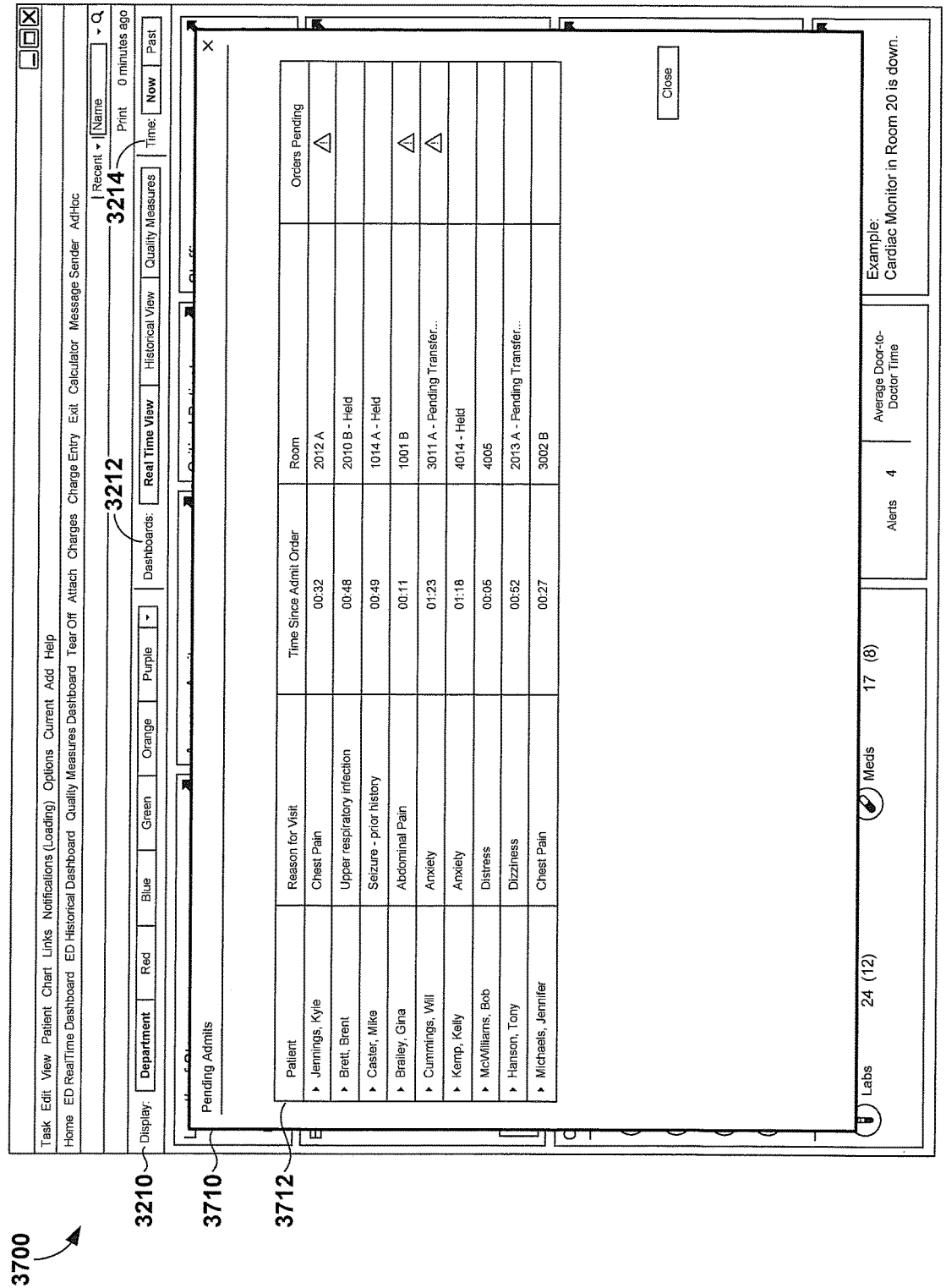

Turning now to FIG. 32, the illustrative screen display 3200 includes an exemplary interactive ED dashboard display that may be displayed at a user computing device, such as the display devices 210 of FIG. 2. In some instances, the user computing device might be a large monitor located at a central location in the ED, such that the ED dashboard display is easily viewed by clinicians in the ED. As mentioned, the ED dashboard display may reflect an overall performance of the ED with respect to various performance metrics. The dashboard may include various user interface indicators that correspond to real-time performance metrics for the ED. For example, user interface indicators may reflect real-time performance metrics for the ED with respect to patient length of stay, patient acuity, critical patients, staffing assignments, as well as any number of other areas of ED performance. These examples, as well as others, will be discussed in more detail below. A clinician may view the dashboard and quickly determine whether ED operations are running smoothly and identify problem areas to be addressed. As discussed below, a clinician may identify a problem area based on the indicators presented in the ED dashboard, and then may select a particular indicator to view patient details and determine the specific actions that should be taken with respect to specific patients in order to remedy the problem.

The exemplary screen display 3200 may include a department display area 3210. The department display area 3210 may include selectable department segment indicators. For example, if a department includes multiple department segments (or "areas" or "zones"), indicators corresponding to those segments may be provided. In the exemplary screen display 3200, the department display area 3210 includes the following segments: Department (corresponding to the entire ED), Red, Blue, Green, Orange, and Purple. These indicators may be selectable. For example, in response to a user input indicating a selection of one of these indicators, the ED dashboard may be customized to reflect the performance of the selected segment. In one instance, upon receiving a selection of "Red," the dashboard indicators, which will be discussed in more detail below, may reflect a performance of the Red segment of the ED (e.g., a performance based on patient data for patients in the Red segment), as opposed to the performance of the entire ED (e.g., a performance based on patient data for patients in the entire ED). In the screen display 3200, the selectable indicator for "Department" is selected (as indicated by the bold font), so the data included in the dashboard reflects the performance of the entire ED, rather than one particular segment within the ED.

The exemplary screen display 3200 may further include a dashboard view area 3212. The dashboard view area may include selectable dashboard view indicators. In this example 3200, the views include: Real Time View, Historical View, and Quality Measures. In response to a selection of the Real Time View indicator, the ED dashboard may display real-time data and performance metrics. This selection may allow a clinician to see what is happening in the ED at that particular time. In response to a selection of the Historical View indicator, the ED dashboard may display historical performance data for the department. The Historical View indicator may include a feature that enables a user to select the particular time period for which the user desires to view performance data. For example, an option to view data from the past week, month, year, or any other customizable time period may be provided. In response to a selection of the Quality Measures indicator, the ED dashboard may display various quality measures. For example, target performance metrics corresponding to a desired performance of the ED may be presented. Critical performance metrics might also be presented. Target performance metrics and critical performance metrics are discussed in more detail below.

A timeframe selection area 3214 might also be included in the screen display 3200. The timeframe selection area 3214 may include selectable timeframe indicators. For example, a user might select "Now" to view real-time data, while a user might select "Past" to view data from the past.

The exemplary screen display 3200 may further include a dashboard indicator display area 3216. Within this area 3216, multiple selectable user interface indicators may be presented on the ED dashboard display. Each indicator may correspond to a performance metric for the ED. A performance metric may be a measurement of the ED's performance with respect to a particular task or activity. Specifically, the performance metrics may be calculated based on patient data for patients in the ED. The performance metrics may be real-time measurements, such that the performance metric reflects the ED's performance at the present moment in time. Historical performance metrics, which may reflect the ED's past performance (e.g., at a past moment in time or over a predefined length of time in the past) may also be provided. When a particular performance metric reaches a critical threshold, thus indicating that the ED performance is especially concerning and/or that conditions in the ED are likely to give rise to a poor performance, alerts may be activated to call attention to the critical problem area.

A length of stay indicator 3218, for example, may correspond to a performance metric for a patient's length of stay within the ED. Specifically, the length of stay indicator 3218 may provide a real-time measurement 3220 of the length of stay associated with patients in the ED. The real-time measurement may be calculated based on patient data for patients in the ED, such as patient data stored at the data store 270 of FIG. 2. Here, the real-time measurement 3220 indicates that a median length of stay for patients in the ED is 3 hours and 52 minutes. Other real-time measurements might be provided, such as an average length of stay. The real-time measurement 3220 may be visually configured to indicate whether or not the measurement is deemed satisfactory with respect to predetermined performance goals for the ED. For example, if a median length of stay of 3 hours and 52 minutes is considered to be a poor performance by the ED, then the real-time measurement 3220 may be yellow to show that this is a potential problem area. The color green may correspond to a positive performance, and the color red may correspond to a critical problem area that needs to be addressed as soon as possible. This color scheme is provided only as an example, and it will be appreciated that any color scheme is included within the scope hereof.

The length of stay indicator 3218 may also include a length of stay details area 322. Among the details shown in the area 3222 may be a target indicator, which may correspond to a target performance threshold for the ED. In the example here, the target length of stay for the ED is 3 hours. This target may be customized for a particular department and/or department segment. A critical performance threshold may also be specified. The critical performance threshold may correspond to a performance that is deemed to be unacceptable for the ED and/or a performance that may interfere with the quality of ED operations, as may be determined based on historical data, for example. If the target length of stay is 3 hours, then a 4-hour length of stay may be deemed unacceptable, and 4 hours may be the critical threshold. The critical threshold may be customized for a particular department and/or department segment. If the ED performance satisfies the critical performance threshold (in this example, satisfying the critical performance threshold would include exceeding the 4-hour length of stay), this may indicate that the ED needs to take corrective action. For example, additional clinicians may be called in to assist. Additionally, satisfying the critical performance threshold may trigger alerts within the ED dashboard.

The length of stay indicator may further include length of stay data for particular patient segments. For example, the length of stay for pending admissions may be specified. Similarly, the length of stay for pending discharges might be called out separately. The length of stay for any desired patient segment may be provided.

Graphical indicators in the graphical indicator area 3224 may provide additional information regarding the ED performance. For example, in the area 3224, the graphical indicator characterized by cross-hatching and including the number 5 may indicate that 5 patients have exceeded the critical length of stay threshold (in embodiments, the graphical indicator may be red to indicate the critical threshold has been exceeded). The graphical indicator characterized by hatching and including the number 4 may indicate that 4 patients have exceeded the target threshold and/or are about to exceed the critical threshold (in embodiments, the graphical indicator may be yellow to indicate the target threshold has been exceeded and/or the critical threshold is about to be exceeded). Accordingly, graphical indicators in the area 3224 may be visually configured in any number of ways to represent relevant performance data. For example, as mentioned above, a color of the graphical indicator may provide an indication of the quality of ED performance with respect to a particular metric.

A selectable indicator 3226 may be selected in order to view the patient data that is relevant to the real-time length of stay performance metric. For example, in response to receiving a user input indicating a selection of the selectable indicator 3226, the patient data used to calculate the median length of stay may be displayed. Such patient data may be presented by the patient data component 252 of FIG. 2, for example.

Figure 33:
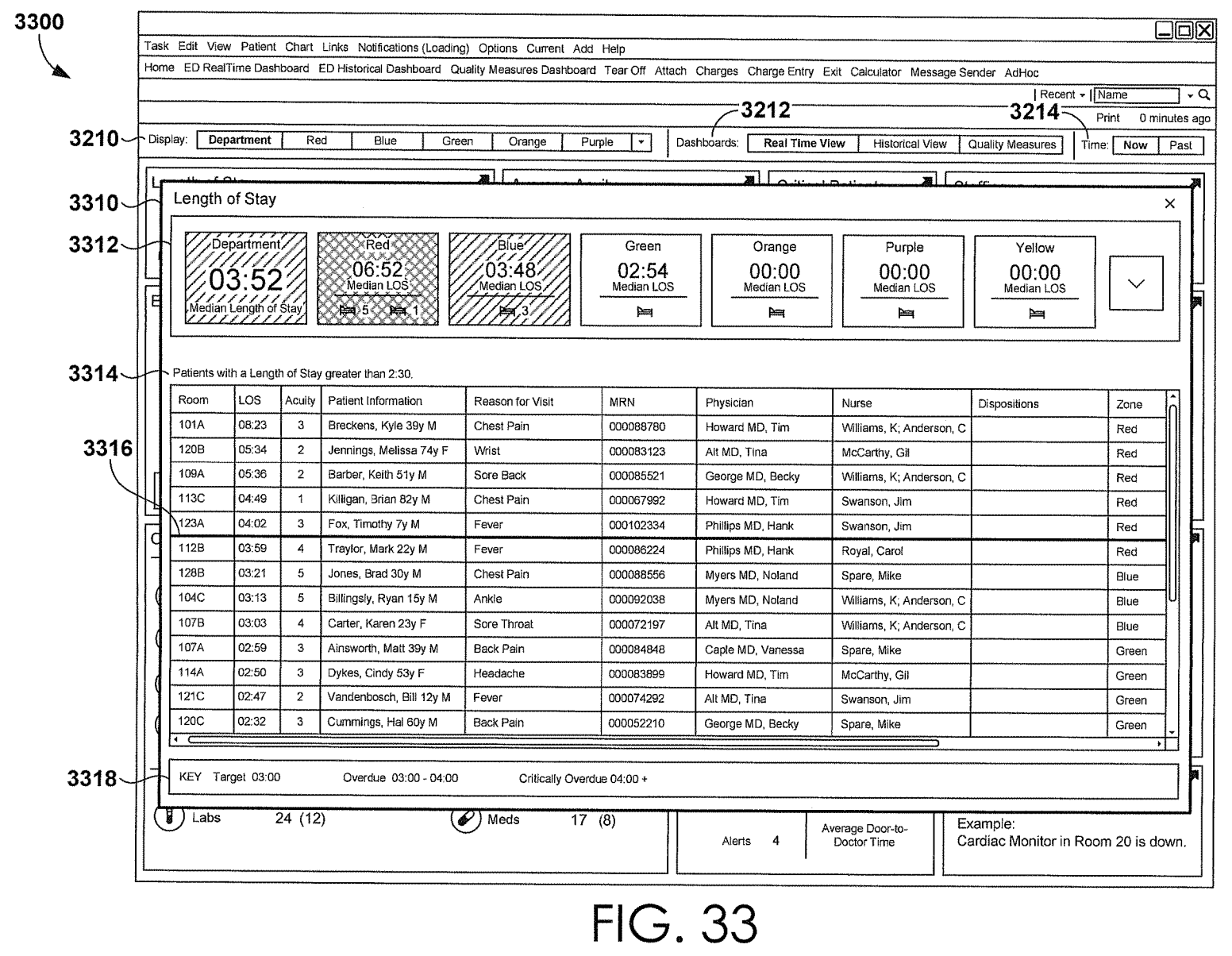

The presentation of such patient data is illustrated in the exemplary screen display 3300 of FIG. 33, where a patient data window 3310 is shown. As illustrated, the patient data window 3310 may be a pop-up window that is displayed in front of the indicators of the ED dashboard. The patient data window 3310 may include segmented length of stay indicators 3312, where the length of stay metric is broken down by department segment. In this example, the median length of stay for the entire department is 3 hours and 52 minutes, while the median length of stay for the Red area is 6 hours and 52 minutes and the median length of stay for the Blue area is 3 hours and 48 minutes. The segmented length of stay indicators may be visually configured to indicate the quality of ED performance that is reflected by the length of stay metric. For example, the cross-hatching of the Red area indicator may indicate that the performance metric for this area has exceeded a critical performance threshold. The hatching of the Blue area indicator may indicate that the performance metric for this area has exceeded a target performance threshold and/or is about to exceed the critical performance threshold. These segmented length of stay indicators 3312 may assist a clinician in identifying areas within the department that are in need of assistance. For example, a clinician may notice that the Orange, Purple, and Yellow areas have a very low median length of stay, and as such, may move personnel from one of these areas to the Red or Blue area to render assistance.

The patient data window 3310 may also include a patient list 3314. The patient list 3314 may include the patient data that is associated with the length of stay performance metric. For example, if patient data for a particular patient was used to calculate the length of stay performance metric, then that particular patient may be included in the patient list 3314. In the present example, the patient list 3314 includes patients with a length of stay over 2 hours and 30 minutes. The patient list 3314 may be filtered in this way to enable a clinician to quickly identify the patients nearing the target length of stay threshold. The patient list may further include a critical threshold indicator 3316. Patients listed above this indicator 3316 may have a length of stay that satisfies the critical performance threshold. Here, a key 3318 indicates that a length of stay over 4 hours is critically overdue. As such, patients with a length of stay over 4 hours are listed above the critical threshold indicator 3316. Patients listed below this indicator 3316 have not yet met that critical threshold of 4 hours. The patient list 3314 may also be visually configured to indicate how data for a particular patient compares to the thresholds. For example, patients having a length of stay that exceeds the critical threshold may be listed in the color red, while patients having a length of stay that exceeds the target threshold and/or is about to exceed the critical threshold may be listed in the color yellow. Thus, a clinician may quickly identify and prioritize patients in need of attention. This color scheme is provided only as an example, and it will be appreciated that any color scheme is included within the scope hereof.

The patient data may be sorted in any number of ways. As illustrated in the exemplary patient list 3314, the patient data may be sorted first according to a length of stay for the patient, such that patients having the longest lengths of stay are listed first, and then according to an acuity rating, such that patients associated with the most severe conditions are listed higher on the patient list 3314 than are those with less severe conditions. It will be understood that the patient data may be sorted according to any number of criteria. Additionally, a segmented length of stay indicator for a particular department segment may be selected in order to filter the patient data included in the patient list 3314 such that patient data only for that selected segment is displayed.

The patient data provided for the list of patients 3314 may include any data that is available for the patient. Such data may include, without limitation, patient room number, length of stay, acuity, patient name, patient age, patient sex, reason for visit, identification number, treating physician, treating nurse, dispositions, and department zone (or "area" or "segment"). This data may be provided for each individual patient on the list 3314. This data may be received from a data store, such as the data store 270 of FIG. 2. The patient data presented may further include the patient data discussed with respect to FIGS. 3-30.

Returning now to FIG. 32, an acuity indicator 3228 may be included in the ED dashboard. As mentioned, an acuity rating may correspond to the severity of a patient's condition. A rating of 1 may correspond to the most severe condition, while a rating of 5 may correspond to the least severe condition. The indicator 3228 may correspond to a performance metric based on acuity ratings for patients within the ED. For example, a real-time measurement 3230 may indicate that the average acuity for patients within the ED is 2.9. The real-time measurement 3230 may be color coded to visually indicate how this acuity rating compares to an optimal acuity rating. For example, it may be determined that the ED operates optimally when the average patient acuity is within a certain range corresponding to a target acuity threshold. A target acuity threshold might be set between 4 and 5, for example. It may further be determined that the ED performs poorly when the average patient acuity satisfies a critical acuity threshold. For example, a critical acuity threshold might be set at 3, such that an average patient acuity of 1-3 satisfies the critical acuity threshold. The real-time measurement 3230 may be colored red, for example, if the average patient acuity satisfies such critical threshold, or yellow when the average acuity is approaching such critical threshold. It may be helpful for clinicians in the ED to know when the acuity is approaching and/or exceeding a certain threshold so that additional resources may be recruited. This color scheme is provided only as an example, and it will be appreciated that any color scheme is included within the scope hereof.

The acuity indicator 3228 may also include a graphical sparkline 3232. This sparkline 3232 may show patient acuity trends within the ED over a particular period of time. In this example, it can be seen that the patient acuity rating has been steadily increasing over time. The sparkline may be color coded to indicate periods of time during which a target and/or critical threshold was satisfied. A clinician may view this information to learn whether patients in the ED at the present time are associated with a more or less severe medical condition, as compared to patients in the ED at a time in the recent past. Thus, indicators included in the ED dashboard may provide a combination of real-time and historical performance data.

A selectable indicator 3234 may be selected in order to view the patient data that forms the basis for the performance metric relating to patient acuity. For example, in response to receiving a user input indicating a selection of the selectable indicator 3234, the patient data relevant to the patient acuity performance metric may be displayed, as shown in exemplary screen display 3400 of FIG. 34.

In particular, the exemplary screen display 3400 includes a patient data window 3410. The patient data window 3410 may include segmented acuity indicators, where an average patient acuity rating is broken down by department segment. In this example, the average acuity rating across patients within the entire ED is 2.9, while the average acuity ratings for patients in the Red and Blue segments are 1.8 and 3.3, respectively. These segmented acuity indicators may be visually configured to illustrate how the rating compares to various acuity thresholds. For example, the hatching of the Department acuity indicator and the Blue acuity indicator may mean that the ratings for these segments are approaching a critical acuity threshold. The cross hatching of the Red acuity indicator may indicate that the rating for this segment has satisfied the critical acuity threshold. This visual configuration may quickly alert a user to the fact that the Red segment may be in need of additional manpower. As explained with respect to the segmented length of stay indicators 3312 of FIG. 33, the segmented acuity indicators 3412 may be selectable, such that a selection of a particular segment indicator causes the patient list 3414 to be filtered such that it only includes patient data only for patients associated with the selected segment.

The patient list 3414 may include the patient data that is associated with the acuity metric. For example, if patient data for a particular patient was used to calculate the acuity performance metric, then that particular patient may be included in the patient list 3414. For each individual patient listed, patient data including at least the patient name and individual acuity rating may be provided. In the present example, the patient list 3414 is sorted according to a patient acuity rating, such that patients associated with the most severe conditions are listed first, and then according to a critical condition, such that patients that have been tagged with a critical condition are listed higher than patients that are not tagged as critical. Patient data may be sorted according to any number of criteria.

The patient list 3414 may further include a critical threshold indicator 3416. Patients listed above this indicator may have an acuity rating that satisfies the critical acuity threshold. Here, for example, the patients listed above the threshold indicator 3416 have an acuity rating that is less than 3. The threshold indicator 3416 may serve to visually separate the patients that are in need of more attention from the patients that are in need of less attention.

Returning to FIG. 32, a critical patient indicator 3236 may be included in the ED dashboard. The critical patient indicator may indicate a subset of patients within the ED that are associated with a critical status. For example, a numerical count 3238 of critical patients may be provided. This may be a real-time indicator, such that the indicated subset of patients includes patients associated with a critical status at the present time. The critical patient indicator 3236 may outline critical patient characteristics that indicate what has caused the patient to be associated with a critical status. For example, a patient associated with a certain event, such as a trauma or a code, may be tagged with a "critical" status. Similarly, a patient with a particularly severe acuity rating may be tagged as "critical." The critical patient indicator 3236 may include a number of patients associated with these and other critical categories. For example, the critical patient indicator 3236 shows that 1 critical patient falls in the "trauma" category, 2 critical patients fall in the "codes" category, and 1 critical patient falls in the "high acuity" category. The critical patient indicator 3236 may be visually configured, such as color coded, to illustrate how the real-time metric compares to critical patient thresholds. It may be useful for clinicians in the ED to know that the number of critical patients is approaching a particular threshold so that additional resources may be recruited.

The critical patient indicator 3236 may include a selectable indicator 3240, which may be selected in order to view the patient data underlying the statistics presented in the critical patient indicator 3236. For example, in response to receiving a user input indicating a selection of the selectable indicator 3240, the patient data relevant to the information presented in the critical patient indicator 3236 may be displayed, as shown in the exemplary screen display 3500 of FIG. 35. The exemplary screen display 3500 may include a patient data window 3510. The patient data window 3510 may include segmented critical patient indicators 3512, where the number of critical patients is broken out by department segment. In this example, there are a total of 4 critical patients in the ED, and of those 4 patients, 3 are in the Red segment and 1 is in the Blue segment. The segmented critical patient indicators may be visually configured to illustrate how the number of critical patients compares to a critical patient threshold. For example, a critical patient threshold may be determined for each segment within the ED, as well as for the entire ED, where the threshold corresponds to a maximum number of critical patients that may be treated without adversely impacting the overall performance of the ED or ED segment. The cross-hatching in the critical patient indicator for the Red segment may indicate that the count of 3 critical patients exceeds the critical patient threshold for the Red segment. As previously explained with respect to other segmented indicators, the segmented indicators 3512 may be selectable in order to filter the patient data presented in the patient list 3514.

The patient list 3514 may include a list of patients included in the critical patient count. Here, the 4 patients in the ED that are associated with a critical status are listed, where the data presented includes, among other items, a patient name and a critical status. The patients may be sorted according to a critical status assigned to the patient and/or according to an acuity rating for the patient. A critical patient threshold indicator 3516 may separate patients that are deemed to be in the most critical conditions from patients that are deemed to be in less critical conditions.

Returning to FIG. 32, a staffing indicator 3242 may be included in the ED dashboard. The staffing indicator 3242 may indicate staffing assignments for the patients in the ED. Staffing assignment information may include an average number of patients assigned to each clinician, as well as an average patient acuity for the patients assigned to each clinician. The staffing indicator 3242 may include a physician component 3244 that indicates staffing assignments associated with physicians and a nurse component 3246 that indicates staffing assignments associated with nurses. Here, the physician component 3244 of the staffing indicator 3242 shows that an average of 8 patients are assigned to each physician, and that on average, each physician is assigned to patients having an average acuity rating of 3.7. The nurse component 3246 of the staffing indicator 3242 shows that an average of 5 patients are assigned to each nurse, and that on average, each nurse is assigned to patients having an average acuity rating of 3.5. The staffing indicator 3242 may reflect real-time staffing assignments. The staffing indicator 3242 may be visually configured to illustrate how the current staffing assignment metrics compare to staffing assignment thresholds. For example, if a metric exceeds a critical staffing assignment threshold, it may be colored red, and if a metric exceeds a target threshold and/or is approaching a critical threshold, it may be colored yellow. This color scheme is provided only as an example, and it will be appreciated that any color scheme is included within the scope hereof.

In addition to indicating when the overall metrics for staffing assignments are approaching and/or exceeding performance thresholds, the staffing indicator 3242 may include graphical indicators, such as graphical indicators 3247, that may be visually configured to indicate when the staffing assignments for a particular individual may be problematic. For example, a graphical indicator that is yellow in color may indicate that the number of patients assigned to a particular clinician and/or an average acuity of patients assigned to a particular clinician is approaching a critical threshold, while a graphical indicator that is red in color may indicate that the number of patients assigned to a particular clinician and/or an average acuity of patients assigned to a particular clinician satisfies a critical threshold. This color scheme is provided only as an example, and it will be appreciated that any color scheme is included within the scope hereof. These thresholds may correspond to a number of patients assigned to a clinician. In some instances, the thresholds might take both the number of patients and the acuity rating for those patients into account, such that a true workload for a particular clinician is considered. Thus, the staffing assignments for a particular clinician might satisfy the target and/or critical threshold if the clinician has been assigned many patients and/or if the clinician has been assigned relatively few patients, but those patients are associated with severe acuity ratings. In this example, the hatching and cross-hatching of the graphical indicators 3247 may indicate that staffing assignments for particular clinicians are approaching and/or satisfying critical staffing thresholds. For example, the hatching might indicate that the staffing assignment for 1 nurse is approaching a critical staffing threshold, while the cross-hatching might indicate that the staffing assignments for 2 nurses have satisfied a critical staffing threshold. This information may be relied upon in reallocating staffing assignments among the clinicians.

The selectable indicator 3248 may be selected to view patient data associated with the staffing assignments summarized in the staffing indicator 3242. Such patient data is included in the exemplary screen display 3600 of FIG. 36. A staffing assignment data window 3610 may include segmented staffing assignment indicators 3612, which may provide information regarding staffing assignments within various segments of the ED. The segmented staffing assignment indicators 3612 may be visually configured to indicate how the staffing assignments compare to staffing assignment thresholds. For example, with respect to the segmented staffing assignment indicator for the Red segment, the hatching may indicate that the physician staffing assignments are approaching a critical staffing assignment threshold, and the cross-hatching may indicate that the nurse staffing assignments have satisfied a critical staffing threshold. As mentioned, this may be based on a combination of the number of patients assigned to each clinician and an average patient acuity for the patients assigned to each clinician. The threshold may further be based on historical data for each clinician. For example, it may be determined based on historical data that a particular clinician struggled with a workload including a certain number of patients and/or patients having an average acuity of a certain level. The critical assignment threshold for that clinician may be determined based on that historical data. Additionally or alternatively, critical thresholds may be determined based on an experience level for a particular clinician, as well as any number of other factors. For example, it may be determined that a patient having a severe acuity rating should not be assigned to a new nurse. Such assignment may satisfy a critical staffing assignment threshold for the new nurse. Accordingly, a workload calculation for each clinician may account for an experience level of the clinician, historical performance by the clinician, a number of patients assigned to the clinician, and a patient acuity rating for the patients assigned to the clinician.

The segmented staffing assignment indicators 3612 may be selectable, and upon selection of an indicator for a particular segment, the data included in the staffing assignment list 3618 may be filtered such that only data for the selected segment is provided.

Two tabs may be provided in the staffing assignment data window 3610, including a tab for physicians 3614 and a tab for nurses 3616. The tab for physicians 3614 may be selected in order to display physician staffing assignment data. The tab for nurses 3616 may be selected in order to display nurse staffing assignment data. In the exemplary screen display 3600, the tab for nurses 3616 has been selected, so the staffing assignment list 3618 includes data for nurse staffing assignments. The information presented may include, for a particular clinician, a clinician name, a number of patients assigned to the clinician, an average acuity rating for the patients assigned to the clinician, a number of critical patients assigned to the clinician, a median number of patients seen by the clinician per hour, a median length of stay associated with the patients assigned to the clinician, a location associated with the patients assigned to the clinician, and a zone (or "segment") associated with the patients assigned to the clinician.

The staffing assignment data window 3610 may further include a critical staffing assignment threshold indicator 3620. This indicator 3620 may separate clinicians having staffing assignments that satisfy a critical staffing assignment threshold from clinicians having staffing assignments that do not satisfy such threshold. Here, two nurses are above the critical staffing assignment threshold indicator 3620, indicating that these clinicians may need to have their patient assignments adjusted. As mentioned, the determination that these two nurses have staffing assignments that satisfy a critical threshold may be based on historical data for those particular nurses. The staffing assignment data window 3610 may be visually configured, such as by color coding, to indicate clinicians that are approaching a critical threshold. For example, clinicians that are approaching the critical threshold may be associated with a yellow color, while clinicians that have already exceeded the critical threshold may be associated with a red color. This color scheme is provided only as an example, and it will be appreciated that any color scheme is included within the scope hereof.

Finally, the staffing assignment data window 3610 may include a key 3622 that includes a target threshold, an "at capacity" threshold, and an "over capacity" (or "critical") threshold. These thresholds may be specified for physicians, nurses, and/or any other clinician. Here, it can be seen that an "over capacity" or "critical" threshold for nurse staffing assignments has been set to 7 patients. Thus, the nurses that have been assigned 7 or more patients are presented above the critical staffing assignment threshold indicator 3620.

Returning to FIG. 32, the ED dashboard may include an ED volume indicator 3250. The ED volume indicator 3250 may include information regarding a patient volume and/or a resource volume within the ED. For example, a graphical indicator 3252 shows a patient volume of 18, which is approaching a maximum patient volume of 20. The graphical indicator 3252 may be visually configured to indicate that the real-time volume measurement is approaching a maximum threshold. For example, the graphical indicator 3252 may be yellow in color. The volume indicator 3250 may further provide available resource details 3254 within the ED. Here, for example, 1 bed is available and 0 beds are dirty. The available resource details 3254 may further include a number of patients that are expected to arrive via emergency medical services ("EMS") (e.g., by ambulance) as well as a number of patients that are expected to arrive as a result of referrals. These details may be helpful, as they may provide context for the real-time ED volume measurement. For example, if the present patient volume is approaching a critical limit, and it is known that multiple patients are expected to arrive as a result of EMS and/or referrals, then a critical situation within the ED may be anticipated and potentially avoided.

The ED volume indicator 3250 may further include a graphical sparkline 3256, which may provide a visual indication of a historical volume trend within the ED. In this example, the ED volume has steadily increased over the past 6 hours. In this way, both real-time and historical data may be presented. The ED volume indicator 3250 may also include a selectable indicator 3258. Selection of the indicator 3258 may cause patient data associated with the ED volume statistics to be displayed.

The ED dashboard display may further include a waiting room indicator 3260 that indicates a wait time associated with the waiting room for the ED. A graphical indicator 3262 may indicate a current waiting room volume, as compared to a maximum volume. Here, 10 patients are currently waiting, and the waiting room can accommodate a maximum capacity of 20 patients. The waiting room indicator 3260 may further include statistics 3264 pertaining to wait times. For example, a median wait time and a longest wait time may be presented. These measurements may be visually configured to illustrate how the measurement compares to a target and/or critical threshold. For example, if 1 hour and 19 minutes exceeds a critical wait threshold, then the measurement may be colored red. If 39 minutes approaches the critical wait threshold, then the measurement may be colored yellow. This color scheme is provided only as an example, and it will be appreciated that any color scheme is included within the scope hereof. The waiting room indicator 3260 may also include a graphical sparkline 3266, which may provide a visual indication of a historical wait time trend within the ED waiting room. In this example, the wait time peaked approximately 3 hours ago, but has since decreased and leveled off. Finally, the waiting room indicator 3260 may include a selectable indicator 3268. Selection of the indicator 3268 may cause patient data associated with the waiting room statistics to be displayed.

Continuing on with respect to FIG. 32, a pending admission indicator 3270 may be included in the ED dashboard display. The pending admission indicator 3270 may include a number of patients pending admission, such as admission to a particular inpatient care unit. For example, a decision may be made that a patient is to be admitted to a particular unit. The patient may remain in the ED (e.g., the patient may be "boarded" in the ED) until the patient is actually admitted and/or transferred to the appropriate unit. Here, a graphical indicator 3272 indicates that 9 patients are pending admission, and that a critical pending admission threshold is set at 10 patients. Thus, the graphical indicator 3272 may be visually configured to illustrate that the number of pending admissions is approaching the critical threshold. The graphical indicator 3272 may be colored yellow or red, for example. This color scheme is provided only as an example, and it will be appreciated that any color scheme is included within the scope hereof.

The pending admission indicator 3270 may also include a pending admission details area 3274. These details may include a total boarding time. The total boarding time may be calculated by summing the boarding time associated with all patients pending admission. This performance metric may be useful, as it indicates an amount of time (and a corresponding amount of resources) that has been devoted merely to holding individuals. The details 3274 may further outline the units to which patients are pending admission. In this example, 1 patient is going to the telemetry unit, 3 patients are going to the ICU, 2 patients are going to surgery, 1 patient is going to acute care, and 1 patient is going to the obstetrics unit.

A graphical sparkline 3276 may be included in the pending admission indicator 3270. The sparkline 3276 may provide a visual indication of a historical trend with respect to pending admissions in the ED. In this example, the number of pending admissions has been increasing over the past 6 hours.

The pending admission indicator 3270 may further include a selectable indicator 3278. Upon receiving a user input indicating a selection of the selectable indicator 3278, patient data corresponding to the pending admissions performance metrics included in the pending admission indicator 3270 may be displayed. Such patient data is presented in the exemplary display screen 3700 of FIG. 37. In particular, the exemplary display screen 3700 may include a patient data window 3710. The patient data window may provide a patient list 3712, which includes patient data for patients pending admission. The patient data included in the patient list 3712 may include, for each patient pending admission, a patient name, reason for visit, time since admit order (e.g., an individual patient wait time), room number, and indication of pending orders. If a patient is being held and/or is pending transfer, that may also be indicated in the patient data.

Returning to FIG. 32, the ED dashboard display may include an overall ED score indicator 3280. The ED score, for example, may reflect the overall performance of the ED, or it may reflect the ED performance with respect to a particular task or activity. In one instance, the ED score may be a patient flow through the hospital. Such score may be based on third party scoring mechanisms. The ED score indicator 3280 may include a graphical indicator that visually represents the quality of ED performance indicated by the ED score. For example, the graphical indicator may be color coded, such that a green color indicates a normal performance, a yellow color indicates a moderate performance (e.g., a performance that is approaching various critical thresholds), and a red color indicates a critical performance (e.g., a performance that is satisfying various critical thresholds). This color scheme is provided only as an example, and it will be appreciated that any color scheme is included within the scope hereof.

The ED dashboard may further include an orders indicator 3282 that includes real-time information regarding orders in the ED. The orders described in the orders indicator 3282 may include various types of procedures, tests, laboratory tests, and medications. For example, a list of ordered diagnostic procedures 3284 may include X-ray, EKG, CT scan, and ultrasound procedures. For each diagnostic procedure, a number of pending orders may be provided in a pending orders column 3286. Here, for example, the pending orders column 3286 indicates that 8 X-ray orders are pending. A number in parentheses next to the number of pending orders may indicate the number of orders that have been pending for an amount of time that exceeds a predetermined threshold. Here, the orders indicator 3282 provides that 1 X-ray order has been pending for over 60 minutes. The indicator may be visually configured to draw attention to the pending order that has exceeded the threshold. For example, the number 1 in parentheses may be colored red. The orders indicator 3282 may further include a column 3288 that provides the average amount of time that elapses between the time that a particular procedure is ordered and the time that a result, such as an image, from the procedure becomes available. For example, the column 3288 indicates that on average, 58 minutes elapse from the time that an X-ray was ordered to the time that an X-ray image from the procedure becomes available. Finally, a column 3290 may provide the average amount of time that elapses between the time that the procedure result becomes available and the time that a preliminary read and/or final report based on the result is completed. For example, the column 3290 indicates that on average, 1 hour and 22 minutes elapse between the time that an X-ray image is available and the time that a preliminary read (e.g., "wet read") is performed. Column 3290 further indicates that on average, 3 hours and 2 minutes elapse between the time that the X-ray image is available and the time that a report based on the image is completed. These various statistics may be color coded to indicate how the statistic compares to a target and/or critical threshold. For example, if a time of 3 hours and 2 minutes exceeds a target and/or critical threshold amount of time for preparing a report based on a diagnostic image, then 3 hours and 2 minutes may be presented in the color red. This color scheme is provided only as an example, and it will be appreciated that any color scheme is included within the scope hereof. It will be understood that the diagnostic procedures included in the list 3284 are exemplary only, and that other diagnostic procedures may be included here.

The orders indicator 3282 may further include a pending laboratory orders area 3292. This may provide a number of pending laboratory orders, as well as a number of pending orders that have exceeded a pending time threshold. Here, for example, 24 laboratory orders are pending and 12 of those orders have been pending for over 30 minutes. These values may be visually configured to draw attention to the pending orders that have exceeded the threshold. For example, the number 12 in parentheses may be colored red. Similarly, a pending medication orders area 3294 may provide a number of pending medications orders, as well as a number of pending orders that have exceeded a pending time threshold. For example, here, 17 medication orders are pending and 8 of those orders have been pending for over 30 minutes. These values may be visually configured to draw attention to the pending orders that have exceeded the threshold. For example, the number 8 in parentheses may be colored red. This color scheme is provided only as an example, and it will be appreciated that any color scheme is included within the scope hereof.

Finally, the orders indicator 3282 may include a selectable indicator 3293. In response to receiving a user input indicating a selection of the selectable indicator 3293, patient data relevant to the pending orders summarized in the orders indicator 3282 may be presented.

The ED dashboard may further include a dispositions indicator 3296. This indicator may provide a summary of patient dispositions in the ED. For example, the summary may include a number of patients that left without being seen, a number of patients that left without treatment, a number of patients that left against medical advice, and a number of patients that were discharged and went home. This summary may be provided for any timeframe, such as the past 6 hours. The dispositions indicator 3296 may provide a sense of the customer service that is being provided by the ED. For example, if many patients are leaving without being seen, that may indicate that the patients are tired of waiting. This inference may be supported by the length of stay performance metric. A selectable indicator 3298 may be selected, and in response, information regarding the patients included in the dispositions summary may be provided.

A pending events indicator 3205 may be presented in the ED dashboard display. This indicator may call out specific patients and/or events. For example, if a particular patient is on suicide watch, this may be specified in a details area 3207 of the pending events indicator 3205. The details area 3207 may also provide a count of entries included on a to-do list, as well as a count of alerts that have been issued. These items may be selected in order to view additional information, such as the specific to-do list entries and the actions required to address the issued alerts. The pending events indicator 3205 may also include a performance metric 3209 that is not included in the other indicators, but is nonetheless relevant to ED performance. For example, a door-to-doctor time may be provided. A selectable indicator 3215 may be selected to view details pertaining to the pending events.

A notices indicator 3201 may include notices and/or announcements for the ED. A clinician may enter a particular notice and/or announcement to be displayed to the ED. For example, a charge nurse might create a message and/or set an alert status. Thus, the notices indicator 3201 may be customized. A selectable indicator 3203 may be selected to view details regarding the notice and/or announcement.

An additional customizable indicator 3211 may be provided. The title and the text included in the indicator 3211 may be customized. For example, the customizable indicator 3211 may be used to provide alerts regarding equipment outages and/or maintenance. For example, the free text might read, "Cardiac monitor in room 20 is down." A selectable indicator 3213 may be selected to view details.

As discussed above with respect to various ED dashboard indicators, the indicators may be visually configured to indicate when ED performance metrics are approaching and/or satisfying target and/or critical thresholds. In addition to such visual configurations, alerts may be presented at the ED dashboard when a performance metric is approaching and/or satisfying such threshold. The alert may comprise a visual, audible, and/or any other sensory indication in order to call attention the particular performance metric. Such alert may be provided by the alerting component 254 of FIG. 2, for example.

As demonstrated by the preceding discussion, the ED dashboard display provides numerous advantages. In particular, the ED dashboard enables a clinician to review ED performance metrics at a high level, and then review information for particular patients associated with those performance metrics. For example, if a clinician sees on the dashboard that one patient has been pending discharge for a period of time that is approaching a critical limit, the clinician may navigate the dashboard to determine the patient's name, location, and other relevant information, and then ensure that someone attends to the patient before the critical limit is reached.

Additionally, the ED dashboard may include a number of predictive features. For example, based on historical data for the ED, critical conditions within the ED may be recognized and/or predicted, such that the conditions may be remedied and/or prevented. For example, historical data may indicate that in one instance, when there was a certain number of patients associated with a certain average acuity assigned to a certain number of nurses, the performance metrics for the ED were approaching and/or satisfying critical performance thresholds. It may further be determined that if one additional nurse had been on duty at that time, the critical performance conditions within the ED could have been avoided. Thus, upon recognizing similar circumstances, an alert may be issued that one additional nurse should be scheduled.

Furthermore, a presentation of the ED dashboard display may be customized for a particular device and/or a particular user. If, for example, a clinician is viewing the ED dashboard on a smart phone, where the display screen is limited in size, the number of ED dashboard indicators that may be presented on the display screen is limited. As such, the indicators may be assigned priorities, such that when a user device at which the ED dashboard is being presented has a display screen of a particular size, a predetermined set of indicators are presented. In some instances, the indicators selected for presentation are based on a clinician role associated with the user. For example, one set of indicators may be most relevant to a nurse, while a different set of indicators may be most relevant to a physician. Thus, the priority assigned to various indicators may be specific to a clinician role. The role of a particular user may be determined based on login information, user-specified role (e.g., a user may provide an input at the user device, where the input specifies a role for the user), a location of a device at which the user is viewing the dashboard (e.g., a device at a nursing station may be customized for a nurse role), or any other means of identifying a user and an associated user role. A particular user may also customize display settings. Such customization preferences may be stored in association with user login information. The priorities assigned to the user interface indicators, the user login information, and the user preferences may be stored at the data store 270 of FIG. 2.

Figure 31:
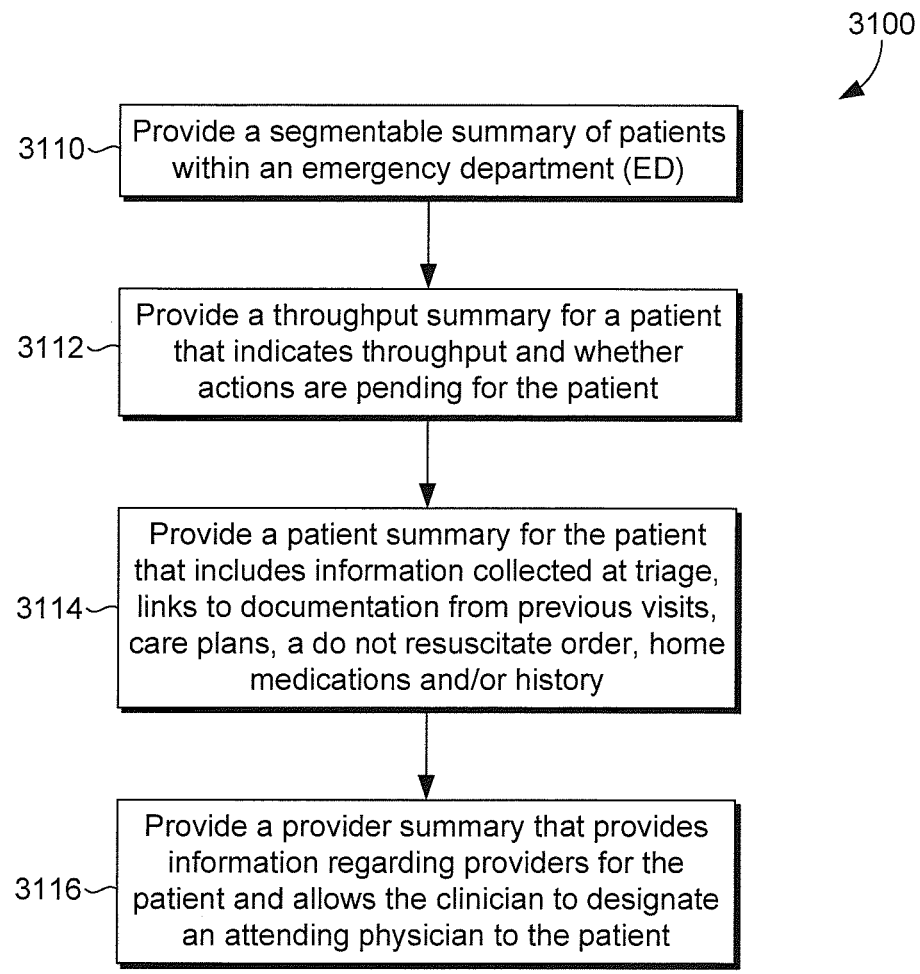
FIG. 31 is a flow diagram of an exemplary method for providing an emergency department centralized interactive display, in accordance with an exemplary embodiment of the present invention.

Turning now to FIG. 31, a flow diagram is illustrated showing an exemplary method 3100 of providing an ED centralized interactive display. As indicated at step 3110, a segmentable summary of patients within an ED may be provided. The segmentable summary may allow a clinician to view a specific area within the ED. The segmentable summary may further allow a clinician to view a summary of patients assigned to the clinician. Unassigned patients may be included in the summary and may be sorted by acuity and length of stay. This may allow a clinician to identify patients that may need a clinician assignment.

A throughput summary for a patient may be provided at step 3112. The throughput summary may indicate throughput and whether actions are pending for the patient. The throughput may indicate whether the patient is pending arrival, waiting for a clinician, an exam has been completed, orders are pending, orders are completed, the patient is ready for discharge, and/or the patient is pending admission.

At step 3114, a patient summary for the patient may be provided, and the patient summary may include information collected at triage, links to documentation from previous visits, care plans, a do not resuscitate order, home medications, and/or history. The patient summary may further include a chief complaint provided by the patient, as well as any accompanying notes or comments.

At step 3116, a provider summary may be provided that provides information regarding providers for the patient and allows the clinician to designate an attending physician to the patient. Designating the clinician as the attending physician may enable the patient to be provided in the summary of patients and may specify initials of the clinician in the segmentable summary of patients. This may allow a clinician to readily identify providers for a particular patient. The provider summary may include placeholders for specific clinician positions to maintain uniformity for the ED centralized interactive display.

In one embodiment, a vitals summary is provided that indicates the most recent vitals measurements, alerts the clinician if any vital readings are stale, alerts the clinician if any vital readings are critical and have not been reviewed, or alerts the clinician if no vital readings are available.

In one embodiment, a medications summary is provided that indicates medications that have been ordered or administered to the patient and allows the clinician to place new orders directly from an orders hover window associated with the medications summary and without having to go into a chart associated with the patient. Graphic indicators may provide, prior to activation or selection (e.g., opening) the medications summary, a progress of medication orders being placed, a ratio of complete versus incomplete medication orders, an indication of medication orders that need review, and/or a glow indication representing an overdue status.

In one embodiment, a laboratory summary is provided. The laboratory summary may indicate that results are completed. The laboratory summary may indicate that the results are overdue. The laboratory summary may indicate that the results have been reviewed. The laboratory summary may allow the clinician to review the results directly from a results hover window associated with the laboratory summary without having to go into the chart associated with the patient. Graphic indicators may provide, prior to activation or selection (e.g., opening) the laboratory summary, a progress of laboratory orders being placed, a ratio of complete versus incomplete laboratory orders, an indication of laboratory orders that need review, and/or a glow indication representing an overdue status.

In one embodiment, an EKG summary is provided. The EKG summary may provide details of an EKG order. The EKG summary may provide a status of the EKG. The EKG summary may provide a link to the EKG results. The link may allow the clinician to open the EKG results directly from the ED centralized interactive display without having to open another application. Graphic indicators may provide, prior to activation or selection (e.g., opening) the EKG summary, a progress of EKG orders being placed, a ratio of complete versus incomplete EKG orders, an indication of EKG orders that need review, and/or a glow indication representing an overdue status.

In one embodiment, an images summary is provided. The images summary may provide a status of an order for an image. The images summary may further provide order details. A link to the image may be provided by the images summary that allows the clinician to open the image from the ED centralized interactive display without having to open another application. The images summary may further indicate a status of documentation for the image. The status may alert the clinician that documentation has been provided or that documentation is still needed. A link to provide documentation after the image is read may also be provided allowing the clinician to open a documentation window and provide documentation from the ED centralized interactive display without having to open another application. Graphic indicators may provide, prior to activation or selection (e.g., opening) the images summary, a progress of image orders being placed, a ratio of complete versus incomplete image orders, an indication of image orders that need review, and/or a glow indication representing an overdue status.

In one embodiment, a consult summary is provided that indicates whether a consult has been requested. The consult summary may further allow the clinician to perform the consult, such as by providing a button that initiates contact with the patient via a mobile device, via a computing device providing the ED centralized interactive display, or via the ED centralized interactive display itself. Graphic indicators may provide, prior to activation or selection (e.g., opening) the consult summary, a progress of consult orders being placed, a ratio of complete versus incomplete consult orders, an indication of consult orders that need review, and/or a glow indication representing an overdue status.

In one embodiment, a length of stay summary is provided that indicates a status associated with a length of stay. For example, the status may indicate a clinician has not been assigned to the patient yet. The status may indicate that orders are pending or complete for the patient. The status may indicate the order that is pending or that a particular order was not entered properly. The status may further indicate the patient is ready for discharge. The length of stay summary may include a timer to alert the clinician if a threshold has been exceeded for the patient. The timer may count up to indicate the current wait time or down to indicate how long the clinician has before a threshold is exceeded.

In one embodiment, a documentation summary is provided that indicates a status associated with documentation for the patient. The status may indicated that the clinician has already provided documentation, that no documentation has been provided, or that documentation is in progress (i.e., further documentation is needed). The documentation summary may further enable the clinician to update, edit, or document an event or encounter without having to open the patient's EMR. The documentation may be saved directly to the patient's EMR.

In one embodiment, a comments summary is provided that allows a clinician to provide comments that are provided for any clinician that is able to view the interactive display for that patient. Each clinician may also be able to open the comments summary to provide additional comments. This may allow direct communication between all clinicians caring for the patient. For example, a clinician may want to alert other clinicians treating the patient that the patient is in a particular unit receiving treatment (i.e., radiology). This may allow other clinicians treating the patient to determine when the patient is available or ready for another treatment.

In one embodiment, an acuity summary for the patient is provided that indicates an acuity for the patient. The acuity may be color coded based on severity. The acuity may further have a numerical indicator providing the clinician additional information regarding the severity. The color coding and the numerical identifier may serve as a visual triage indicator allowing the clinician to quickly identify the patient in the most urgent need of attention.

In one embodiment, in any of summaries that is open or selected, tabs are provided for each of the other summaries that allow the clinician to select another summary to open by selecting the desired tab. This feature may allow the clinician to quickly change the summary without closing the currently open summary and selecting a new summary from the interactive display. Similarly, the clinician can, from within each tab, place and review orders for the selected tab, without having to go into the chart associated with the patient.

Figure 38:
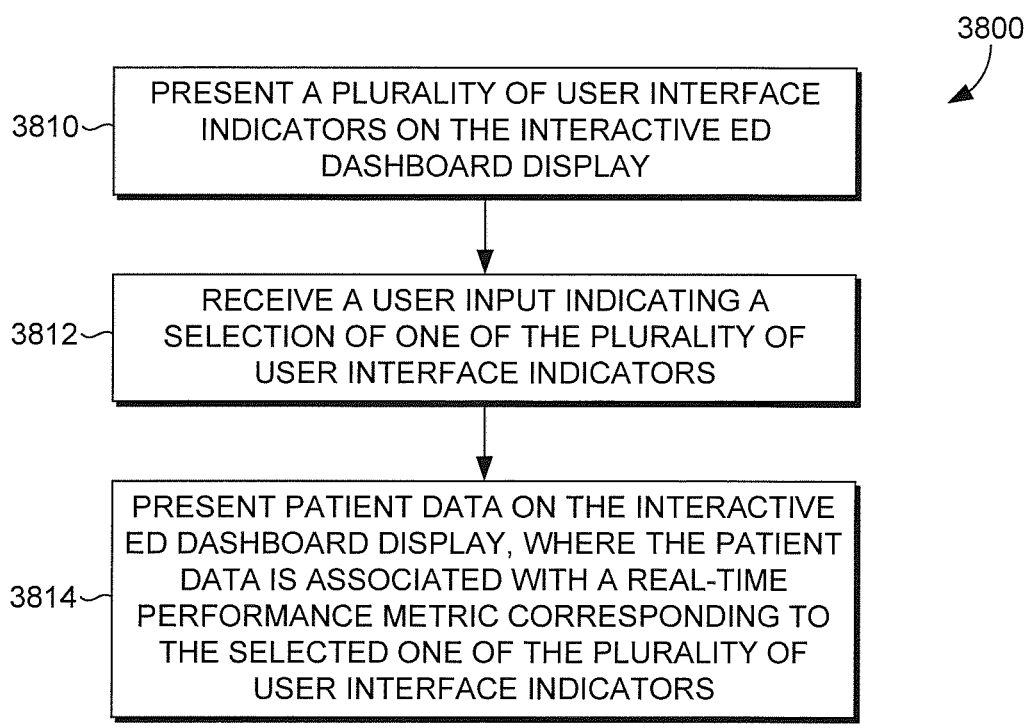
FIG. 38 is a flow diagram of an exemplary method for presenting an interactive emergency department dashboard display, in accordance with an exemplary embodiment of the present invention.

Turning now to FIG. 38, a flow diagram for presenting an interactive ED dashboard display for an ED is presented. The ED dashboard display may be presented at a user computing device, such as the display devices 210 of FIG. 2. At step 3810, a plurality of user interface indicators may be presented on the interactive ED dashboard display at the user computing device. Each of the plurality of user interface indicators may correspond to a real-time performance metric for the ED, where the real-time performance metric is based on patient data for a plurality of patients in the ED.

Presenting the plurality of user interface indicators may include, for example, presenting a real-time length of stay indicator that indicates a length of stay associated with the plurality of patients in the ED, presenting a real-time acuity indicator that indicates an acuity associated with the plurality of patients in the ED, presenting a real-time critical patient indicator that indicates a first subset of the plurality of patients in the ED that is associated with a critical status, presenting a real-time staffing indicator that indicates staffing assignments for the plurality of patients in the ED, presenting a real-time volume indicator that indicates a patient volume and a resource volume associated with the ED, presenting a real-time waiting room indicator that indicates a wait time associated with a waiting room for the ED, presenting a real-time pending admission indicator that indicates a second subset of the plurality of patients in the ED that is pending admission, and presenting a real-time order indicator that indicates orders associated with the plurality of patients in the ED.

At step 3812, a user input may be received, where the user input indicates a selection of one of the plurality of user interface indicators. The user input may be received at the user computing device. In response to the user input, at step 3814, patient data may be presented on the interactive ED dashboard display at the user computing device, where the patient data is associated with the real-time performance metric corresponding to the selected one of the plurality of user interface indicators. Obtaining the patient data that is associated with the real-time performance metric may include receiving, from a patient data store, such as the data store 270 of FIG. 2, the patient data for the plurality of patients in the ED. Then, based on the received user input, the patient data for the plurality of patients may be filtered to provide the patient data that is associated with the real-time performance metric. Such filtering may be performed by the patient data component 252 of FIG. 2, for example.

In one example, the selected one of the plurality of user interface indicators may be the real-time length of stay indicator, and the patient data that is presented in response to this selection may include, for each of the plurality of patients in the ED, a patient name and an individual patient length of stay. The real-time performance metric corresponding to the length of stay indicator may include a median length of stay for the plurality of patients in the ED.

In another example, the selected one of the plurality of user interface indicators may be the real-time acuity indicator, and the patient data that is presented in response to this selection may include, for each of the plurality of patients in the ED, a patient name and an individual patient acuity. The real-time performance metric corresponding to the real-time acuity indicator may include an average acuity for the plurality of patients in the ED.

In yet another example, the selected one of the plurality of user interface indicators may be the real-time critical patient indicator, and the patient data that is presented in response to this selection may include, for each of the first subset of the plurality of patients in the ED that is associated with the critical status, a patient name and an individual patient critical status. The real-time performance metric corresponding to the real-time critical patient indicator may include a number of patients in the first subset of the plurality of patients in the ED that is associated with the critical status.

In a further example, the selected one of the plurality of user interface indicators is the real-time staffing indicator, and the patient data that is presented in response to this selection may include a number of patients assigned to a clinician in the ED and an average acuity associated with the patients assigned to the clinician in the ED.

In an additional example, the selected one of the plurality of user interface indicators is the real-time pending admission indicator and the patient data that is presented may include, for each of the second subset of the plurality of patients in the ED that is pending admission, a patient name and an individual patient wait time. The real-time performance metric corresponding to the real-time pending admission indicator may include a number of patients in the second subset of the plurality of patients in the ED that is pending admission. The number of patients in the second subset of the plurality of patients may be segmented according to a particular area within the ED to which each patient of the second subset of the plurality of patients is awaiting admission.

In some instances, the method 3800 may further include determining that at least one real-time performance metric satisfies a critical performance threshold. In response to this determination, an alert may be presented at the ED dashboard display. The alert may be a visual, audible, and/or any other sensory indicator.

It will be understood by those of ordinary skill in the art that the order of steps shown in methods 3100 and 3800 of FIGS. 30 and 38 is not meant to limit the scope of the present invention in any way and, in fact, the steps may occur in a variety of different sequences within embodiments hereof. Any and all such variations, and any combination thereof, are contemplated to be within the scope of embodiments of the present invention.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computer system for providing an interactive emergency department (ED) dashboard comprising:
   one or more processors; and
   one or more computer storage media storing computer-executable instructions that, when used by the one or more processors, are configured to implement a method comprising:
   receiving real-time performance metrics corresponding to a plurality of indicators of the interactive ED dashboard, the plurality of indicators comprising a critical patient indicator and a staffing indicator;
   determining at least one of the real-time performance metrics of the critical patient indicator satisfies a first threshold for distinguishing urgencies of a particular action that should be taken with respect to a particular patient;
   determining at least one of the real-time performance metrics of the staffing indicator satisfies a second threshold that is based on clinician experience level, clinician historical performance, and a number of patients assigned;

assigning priorities to the plurality of indicators based on whether a particular real-time performance metric satisfied the first threshold or the second threshold; and based on a screen size of a computing device associated with a viewing session of the interactive ED dashboard and on the priorities, providing for presentation, at the computing device via the interactive ED dashboard, the plurality of indicators, wherein the presentation indicates:

a patient having a real-time performance metric that satisfies the first threshold or the second threshold; or a patient having a real-time performance metric that does not satisfy the first threshold or the second threshold.

2. The computer system of claim 1, wherein the real-time performance metrics are based on patient data for a plurality of patients of at least one emergency department.

3. The computer system of claim 2, further comprising computer-executable instructions for:

receiving a selection of at least one of the plurality of indicators; and providing for presentation a subset of the patient data that is associated with the at least one of the plurality of indicators.

4. The computer system of claim 3, wherein the subset of the patient data comprises a documentation summary that indicates a status associated with documentation for a patient at the at least one emergency department.

5. The computer system of claim 1, further comprising computer-executable instructions for:

determining at least one of the real-time performance metrics of an acuity indicator satisfies a third threshold for indicating when a severity of a condition of a patient has increased, the acuity indicator corresponding to the severity of the condition of the patient; and providing for presentation at least one of the real-time performance metrics of the acuity indicator that satisfies the third threshold.

6. The computer system of claim 1, further comprising computer-executable instructions for:

determining at least one of the real-time performance metrics of a length of stay indicator satisfies a target performance threshold for an emergency department, wherein the length of stay indicator provides a measurement of a length of stay of a patient in the emergency department, the length of stay including pending admissions to the emergency department; and providing for presentation at least one of the real-time performance metrics of the length of stay indicator that satisfies the target performance threshold.

7. The computer system of claim 6, further comprising computer-executable instructions for:

indicating the patient that has at least one of the real-time performance metrics of the length of stay indicator that satisfies the target performance threshold; and indicating a corrective action should be taken.

8. A method for providing an interactive emergency department (ED) dashboard, the method comprising:

receiving real-time performance metrics corresponding to a plurality of indicators of the interactive ED dashboard, the plurality of indicators comprising a critical patient indicator, a staffing indicator, and a volume indicator that indicates a volume of patients at an emergency department;

determining at least one of the real-time performance metrics of the critical patient indicator satisfies a first threshold for distinguishing urgencies of particular actions that should be taken with respect to particular patients;

determining at least one of the real-time performance metrics of the volume indicator satisfies a second threshold that is based on a maximum or critical patient volume;

determining at least one of the real-time performance metrics of the staffing indicator satisfies a third threshold that is based on clinician experience level, clinician historical performance, and a number of patients assigned;

assigning priorities to the plurality of indicators based on whether a particular real-time performance metric satisfied the first threshold, the second threshold, or the third threshold; and based on a screen size of a computing device associated with a viewing session of the interactive ED dashboard and on the priorities, providing for presentation, at the computing device via the interactive ED dashboard, the plurality of indicators, wherein the presentation indicates:

a patient having a real-time performance metric that satisfies the first threshold, the second threshold, or the third threshold; or a patient having a real-time performance metric that does not satisfy the first threshold, the second threshold, or the third threshold.

9. The method of claim 8, wherein the presentation indicates a patient having a real-time performance metric that does not satisfy the second threshold, and wherein a selectable indicator is presented, selection upon which causes volume statistics comprising historical volume trends within the emergency department to be displayed.

10. The method of claim 8, wherein the presentation indicates a patient having a real-time performance metric that satisfies the second threshold, and wherein in response to the patient having the real-time performance metric that satisfies the second threshold, triggering an alert.

11. The method of claim 8, further comprising upon receiving a selection of the volume indicator, presenting a volume of patients that are expected to arrive to the emergency department via EMS and a volume of patients that are expected to arrive as a result of referral, and wherein the expected arrivals are within a predetermined time.

12. The method of claim 8, further comprising upon receiving a selection of the volume indicator, presenting a volume of available beds.

13. The method of claim 8, wherein the plurality of indicators further comprise a pending admission indicator that provides visual indications of historical trends of pending admissions at the emergency department.

14. The method of claim 8, further comprising upon receiving a selection of the volume indicator, presenting a volume of patients who have left the emergency department without being seen.

15. The method of claim 8, wherein the first threshold is determined based on historical data of patients, and wherein the method further comprises:

recognizing and predicting a condition to be remedied or prevented based on the historical data of patients at the emergency department; and after receiving an input, customizing a presentation of the critical patient indicator, the customizing comprising identifying the condition.

16. One or more non-transitory computer storage media having computer-executable instructions embodied thereon, that when executed by at least one processor, cause a computer system to perform a method for providing an interactive emergency department (ED) dashboard, the method comprising:

receiving real-time performance metrics corresponding to a plurality of indicators of the interactive ED dashboard, the plurality of indicators comprising a staffing indicator and a volume indicator that indicates a volume of patients at an emergency department;

determining at least one of the real-time performance metrics of the staffing indicator satisfies a first threshold that is based on clinician experience level, clinician historical performance, and a number of patients assigned;

determining at least one of the real-time performance metrics of the volume indicator satisfies a second threshold that is based on a maximum or critical patient volume;

assigning priorities to the plurality of indicators based on whether a particular real-time performance metric satisfied the first threshold or the second threshold; and based on a screen size of a computing device associated with a viewing session of the interactive ED dashboard and on the priorities, providing for presentation, at the computing device via the interactive ED dashboard, the plurality of indicators, wherein the presentation indicates:

a patient having a real-time performance metric that satisfies the first threshold or the second threshold; or a patient having a real-time performance metric that does not satisfy the first threshold or the second threshold.

17. The non-transitory computer storage media of claim 16, further comprising computer-executable instructions configured to cause the computer system to perform: upon receiving a selection of the staffing indicator, presenting staffing assignment information including an average number of patients assigned to each clinician and staffing assignments associated with particular physicians and particular nurses.

18. The non-transitory computer storage media of claim 16, further comprising computer-executable instructions configured to cause the computer system to perform: presenting an alert in response to determining the at least one of the real-time performance metrics of the staffing indicator satisfies the first threshold or in response to determining the at least one of the real-time performance metrics of the volume indicator satisfies the second threshold.

19. The non-transitory computer storage media of claim 16, wherein the computer-executable instructions for providing for presentation further comprises computer-executable instructions configured to generate on a screen of the computing device having the screen size, a patient data window comprising the plurality of indicators.

20. The non-transitory computer storage media of claim 19, wherein the patient data window is configured to provide, the plurality of indicators based on their respective emergency department segments.

* * * * *